(12) United States Patent
Chang et al.

(10) Patent No.: US 11,951,167 B2
(45) Date of Patent: Apr. 9, 2024

(54) TARGETED LIPOSOMES

(71) Applicant: GEORGETOWN UNIVERSITY, Washington, DC (US)

(72) Inventors: Esther H. Chang, Potomac, MD (US); SangSoo Kim, Gaithersburg, MD (US); Antonina Rait, Rockville, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 497 days.

(21) Appl. No.: 17/168,614

(22) Filed: Feb. 5, 2021

(65) Prior Publication Data

US 2021/0205456 A1 Jul. 8, 2021

Related U.S. Application Data

(62) Division of application No. 14/030,563, filed on Sep. 18, 2013, now abandoned.
(Continued)

(51) Int. Cl.
*A61K 45/06* (2006.01)
*A61K 9/00* (2006.01)
*A61K 9/127* (2006.01)

(52) U.S. Cl.
CPC ............ *A61K 45/06* (2013.01); *A61K 9/0019* (2013.01); *A61K 9/1271* (2013.01); *A61K 9/1272* (2013.01)

(58) Field of Classification Search
CPC .... A61K 45/06; A61K 9/0019; A61K 9/1271; A61K 9/1272
See application file for complete search history.

(56) References Cited

U.S. PATENT DOCUMENTS

| 5,776,487 A | 7/1998 | Wilson et al. |
| 6,027,892 A | 2/2000 | Chang et al. |

(Continued)

FOREIGN PATENT DOCUMENTS

| CA | 2577036 | * | 2/2006 |
| CA | 2671524 | * | 6/2008 |

(Continued)

OTHER PUBLICATIONS

Campbell et al. "Lipofection reagents prepared by a simple ethanol injection technique", Biotechniques, vol. 18 (1995) pp. 1027-1032.
(Continued)

*Primary Examiner* — Gollamudi S Kishore
(74) *Attorney, Agent, or Firm* — MEDLER FERRO WOODHOUSE & MILLS PLLC

(57) ABSTRACT

The present invention is in the field of drug delivery, and specifically, cationic liposome-based drug delivery. In embodiments, this invention provides methods of making ligand-targeted (e.g., antibody- or antibody fragment-targeted) liposomes useful for the delivery of liposomes to tumors, including brain tumors. In embodiments, the liposomes deliver temozolomide across the blood-brain barrier for treatment of primary or metastatic brain tumors. Additional cancers that can be treated with the liposomes include neuroendocrine tumors, melanoma, prostate, head and neck, ovarian, lung, liver, kidney, breast, urogenital, gastric, colorectal, cervical, vaginal, angiosarcoma, liposarcoma, rhabdomyosarcoma, choriocarcinoma, pancreatic, retinoblastoma and other types of cancer. In another embodiment the liposomes deliver melphalan for the treatment of multiple myeloma, other tumors of the blood or other solid tumors. In still other embodiments the liposomes can deliver other drugs such as pemetrexed or irinotecan for treatment of
(Continued)

cancer or drugs including atropine for treatment of organophosphate poisoning.

30 Claims, 39 Drawing Sheets

Related U.S. Application Data

(60) Provisional application No. 61/767,453, filed on Feb. 21, 2013, provisional application No. 61/702,796, filed on Sep. 19, 2012.

(56) References Cited

U.S. PATENT DOCUMENTS

| | | | |
|---|---|---|---|
| 6,156,337 | A | 12/2000 | Barenholz et al. |
| 6,596,305 | B1 | 7/2003 | Edgerly-Plug |
| 6,749,863 | B1 | 6/2004 | Chang et al. |
| 6,803,360 | B1 | 10/2004 | Chang et al. |
| 7,479,276 | B1 | 1/2009 | Xu et al. |
| 7,780,822 | B2 | 8/2010 | Beckmann et al. |
| 7,780,882 | B2 | 8/2010 | Chang et al. |
| 8,617,514 | B2 | 12/2013 | Chang et al. |
| 2002/0054902 | A1* | 5/2002 | Pardridge ............... C12N 15/88 435/458 |
| 2003/0044407 | A1 | 3/2003 | Chang et al. |
| 2003/0072794 | A1 | 4/2003 | Boulikas |
| 2003/0129222 | A1 | 7/2003 | Lopez-Berestein et al. |
| 2003/0228285 | A1 | 12/2003 | Hung et al. |
| 2004/0018985 | A1 | 1/2004 | Sakon et al. |
| 2004/0241088 | A1 | 12/2004 | Chang et al. |
| 2004/0258747 | A1 | 12/2004 | Ponzoni et al. |
| 2005/0002998 | A1 | 1/2005 | Chang et al. |
| 2005/0063950 | A1 | 3/2005 | Chang et al. |
| 2005/0277611 | A1 | 12/2005 | Ahmad et al. |
| 2007/0065432 | A1 | 3/2007 | Xu et al. |
| 2007/0065449 | A1 | 3/2007 | Verschraegen et al. |
| 2007/0065499 | A1 | 3/2007 | Chang et al. |
| 2007/0231378 | A1 | 10/2007 | Chang et al. |
| 2008/0193511 | A1* | 8/2008 | Massing ............... A61K 9/5123 422/243 |
| 2008/0213223 | A1 | 9/2008 | Chang et al. |
| 2008/0311182 | A1* | 12/2008 | Ferrari ............... A61K 31/704 514/769 |
| 2009/0053299 | A1 | 2/2009 | Chang et al. |
| 2009/0191261 | A1 | 7/2009 | Xu et al. |
| 2010/0047329 | A1 | 2/2010 | Watarai et al. |
| 2010/0061992 | A1* | 3/2010 | Anderson ............... A61P 3/02 424/139.1 |
| 2010/0329981 | A1 | 12/2010 | Chang et al. |
| 2011/0117141 | A1 | 5/2011 | Huang et al. |
| 2012/0183602 | A1 | 7/2012 | Chen et al. |
| 2012/0201872 | A1 | 9/2012 | Huang et al. |
| 2014/0120157 | A1 | 5/2014 | Chang et al. |

FOREIGN PATENT DOCUMENTS

| | | |
|---|---|---|
| JP | 2008-514609 | 5/2008 |
| JP | 2009-512712 | 3/2009 |
| JP | 2012-144512 | 8/2012 |
| WO | WO 99/25320 | 5/1999 |
| WO | 00/50008 | 8/2000 |
| WO | 02/078608 | * 10/2002 |
| WO | 03/030818 | 4/2003 |
| WO | WO 2007/088952 | 8/2007 |
| WO | WO 2009/009054 | 1/2009 |

OTHER PUBLICATIONS

Berrocal et al., "Extended-Schedule Dose-Dense Temozolomide in Refractory Gliomas", Journal of Neuro-Oncology, vol. 96 (2010), pp. 417-422.

Blakeley, "Drug delivery to brain tumors", Current Neurology & Neuroscience Reports, vol. 8 (2008), pp. 235-241.

Bocangel et al., "P53-Mediated Down-Regulation of the Human DNA Repair Gene O6- Methylguanine-DNA Methyltransferase (MGMT) via Interaction With Sp1 Transcription Factor", Anticancer Research (2009).

Cerrato et al., "Introduction of Mutant P53 into a Wild-Type P53-Expressing Glioma Cell Line Confers Sensitivity to Ad-P35-Induced Apoptosis", Neuro-Oncology, vol. 3 (2001), pp. 113-122.

Chamberlain, "Temozolomide: Therapeutic Limitations in the Treatment of Adult High-Grade Gliomas", Expert Review of Neurotherapeutics, vol. 10 (2010), pp. 1537-1544.

Chang et al., "Targeted Iron Oxide Nanocomplex as a Theranostic Agent for Cancer", Nanomedicine—Basic and Clinical Applications in Diagnostic Therapy, Else Kroner-Fresenius Symp. Basel, Karger, (2011), pp. 145-153.

Chang et al., "Treatment for Exposure to Nerve Agent", U.S. Appl. No. 14/208, 187, filed Mar. 13, 2014.

Chang et al., "Tumor-Targeted Nanodelivery Systems to Improve Early MRI Detection of Cancer", U.S. Appl. No. 14/098,957, filed Dec. 06, 2013.

Cheng, "Receptor ligand-facilitated gene transfer: enhancement of liposome-mediated gene transfer and expression by transferrin", Human Gene Therapy, vol. 7 (1996), pp. 275-282.

Chirasani et al., "Transferrin-Receptor-Mediated Iron Accumulation Controls Proliferation and Glutamate Release in Glioma Cells", Journal of Molecular Medicine-Jmm, vol. 87 (2009), pp. 153-167.

Chrastina et al., "Overcoming in Vivo Barriers to Targeted Nanodelivery", Wiley Interdisciplinary Reviews—Nanomedicine and Nanobiotechnology, vol. 3 (2011), pp. 421-437.

Clark and Hersh, "Cationic lipid-mediated gene transfer: Current concepts", Current Opinion in Molecular Therapeutics, vol. 1 (1999), pp. 158-176.

Dagata et al., "Physical characterization methods for iron-oxide contrast agents encapsulated within a targeted liposome-based delivery system", Nanotechnology, vol. 19, Issue 30 (2008), p. 305101.

Davis et al., "Evidence of RNAi in Humans from Systematically Administered SiRNA via Targeted Nanoparticles", Nature, vol. 464 (2010), pp. 1067-U140.

Dean et al., "Tumour Stem Cells and Drug Resistance", Nat. Rev. Cancer, vol. 5 (2005), pp. 275-284.

Elliott et al., "Breast carcinoma and the role of iron metabolism: a cytochemical, tissue culture, and ultrastructural study", Annals of the New York Academy of Sciences, vol. 698 (1993), pp. 159-166.

Farkas et al., "Combined scanning probe and light scattered characterization of multi-stage self-assembly of targeted liposome-based delivery systems", Measurement Science and Technology, vol. 22 (2011), 12 pgs.

Freedman et al., "Nanodelivery of MRI contrast agent enhances sensitivity of detection of lung cancer metastases", Academic Radiology, vol. 16 (2009), pp. 627-637.

Haggerty et al., "Hyperphosphorylated Tau in an Alpha-Synuclein-Overexpressing Transgenic Model of Parkinson's Disease", European Journal of Neuroscience, vol. 33 (2011), pp. 1598-1610.

Harris et al., "Wild-Type P53 Suppresses Transcription of the Human O6-Methylguanine-DNA Methyltransferase Gene", Cancer Research, vol. 56 (1996), pp. 2029-2032.

Hegi, "MGMT Gene Silencing and Benefit From Temozolomide in Glioblastoma", New England Journal of Medicine, vol. 352 (2005), pp. 997-1003.

Hogrefe et al., "Chemically modified short interfering hybrids (siHYBRIDS): nanoimmunoliposome delivery in vitro and in vivo for RNAi of HER-2", Nucleosides, Nucleotides & Nucleic Acids, vol. 25 (2006), pp. 889-907.

Huang et al., "Solid Lipid Nanoparticles of Temozolomide: Potential Reduction of Cardial and Nephric Toxicity", International Journal of Pharmaceuticals, vol. 355 (2008), pp. 314-320.

Hurt et al., "Reversal of p53 epigenetic silencing in multiple myeloma permits apoptosis by a p53 activator", Cancer Biology and Therapy, vol. 5 (2006), pp. 1154-1160.

Hwang et al., "Tumor-targeting nanodelivery enhances the anticancer activity of novel quinazolinone analog", Molecular Cancer Therapeutics, vol. 7, Issue 3 (2008), pp. 1-10.

(56) References Cited

OTHER PUBLICATIONS

Jeffries et al., "Transferrin receptor on endothelium of brain capillaries", Nature, vol. 312 (1984), pp. 162-163.
Jiang et al., "A Novel Approach to Overcome Temozolomide Resistance in Glioma and Melanoma: Inactivation of MGMT by Gene Therapy", Biochemical and Biophysical Research Communications, vol. 406 (2011), pp. 311-314.
Kanzawa et al., "Role of Autophagy in Temozolomide-Induced Cytotoxicity for Malignant Glioma Cells", Cell Death and Differentiation, vol. 11 (2004), pp. 448-457.
Keer, et al., "Elevated transferring receptor content in human prostate cancer cell lines assessed in vitro and in vivo", Journal of Urology, vol. 143 (1990), pp. 381-385.
Kim et al., "Importance of PKC Delta Signaling in Fractioned-Radiation-Induced Expansion of Glioma Initiating Cells and Resistance to Cancer Treatment", Journal of Cell Science, vol. 124 (2011), pp. 3084-3094.
Lian and Ho, "Trends and developments in liposome drug delivery systems", Journal of Pharmaceutical Sciences, vol. 90 (2001), pp. 667-680.
Liu et al., "Efficacy of Adenovirally Expressed Soluble TRAIL in Human Glioma Organotypic Slice Culture and Glioma Xenografts", Cell Death and Disease, vol. 2 (2011).
Ludwig et al., "Current MM treatment strategies with novel agents: a European perspective", Oncologist, vol. 10, Issue 1 (2010), pp. 6-25.
Meije et al., "Emergence of Cytomegalovirus Disease in Patients Receiving Temozolomide: Report of Two Cases and Literature Review", Clinical Infectious Diseases, vol. 50 (2010), pgs. E73-E76.
Miyamoto et al., "Transferrin receptor in oral tumors", International Journal of Oral & Maxillofacial Surgery, vol. 23 (1994), pp. 430-433.
Mrugala et al., "Temozolomide: Expanding Its Role in Brain Cancer", Drugs of Today, vol. 46 (2010), pp. 833-846.
Newlands et al., "Antitumor Imidazotetrazines .26 Phase-I Trial of Temozolomide (Ccrg-81045, M- And-B 39831, Nsc-362856)", British Journal of Cancer, vol. 65 (1992), pp. 287-291.
Pardal et al., "Applying the Principles of Stem-Cell Biology to Cancer", Nat. Rev. Cancer, vol. 3 (2003), pp. 895-902.
Park et al., "Cancer Stem Cell-Directed Therapies: Recent Data from the Laboratory and Clinic", Molecular Therapy, vol. 17 (2009), pp. 219-230.
Patil et al., "Temozolomide Delivery to Tumor Cells by a Multifunctional Nano Vehicle Based on Poly(Beta-L-Malic Acid)", Pharmaceutical Research, vol. 27 (2010), pp. 2317-2329.
Pirollo et al., "A tumor-targeted nanodelivery system to improve early MRI detection of cancer", Molecular Imaging, vol. 5 (2006), pp. 41-52.
Pirollo et al., "Immunoliposomes: a targeted delivery tool for cancer treatment", Vector Targeting for Therapeutic Gene Delivery, Wiley Press (2002), pp. 33-62.
Pirollo et al., "Materializing the Potential of siRNA via a Tumor-Targeting Nanodelivery System", Cancer Research, vol. 67, Issue 7 (2007), pp. 2932-2937.
Pirollo et al., "Non-viral gene delivery for p53", Current Opinion in Molecular Therapeutics, vol. 2 (2000), pp. 168-175.
Pirollo et al., "Transgene presence in patients' tumors following tumor-targeted nanodelivery", Cancer Research, vol. 70 (2011), pp. LB-172.
Pirollo et al., "Tumor-targeting nanocomplex delivery of novel tumor suppressor RB94 chemosensitizes bladder carcinoma cells in vitro and in vivo", Clinical Cancer Research, vol. 14 (2008), pp. 2190-2198.
Pirollo et al., "Tumor-targeting nanoimmunoliposome complex for short interfering RNA delivery", Human Gene Therapy, vol. 17 (2006), pp. 117-124.
Ponka and Lok, "The transferring receptor: role in health and disease", International Journal of Biochemistry & Cell Biology, vol. 31 (1999), pp. 1111-1137.
Purow et al., "Expression of Notch-1 and Its Ligands, Delta-Like-1 and Jagged-1, Is Critical for Glioma Cell Survival and Proliferation", Cancer Research, vol. 65 (2005), pp. 2325-2363.
Rait et al., "HER-2-targeted antisense oligonucleotide results in sensitization of head and neck cancer cells to chemotherapeutic agents", Annals of the New York Academy of Sciences, vol. 1002 (2003), pp. 78-89.
Rait et al., "Inhibitory effects of the combination of HER-2 antisense oligonucleotide and chemotherapeutic agents used for the treatment of human breast cancer", Cancer Gene Ther., vol. 8 (2001), pp. 728-739.
Rait et al., "Systemic delivery of nanocomplexed SPIO to human cancer cells in both primary and metastatic tumor", Submitted to NanoLetters.
Rait et al., "Tumor-targeting, systemically delivered ASHER-2 chemosensitizes human breast cancer xenografts irrespective of HER-2 levels", Molecular Medicine, vol. 8 (2002), pp. 475-486.
Reya et al., "Stem Cells, Cancer, and Cancer Stem Cells", Nature, vol. 414 (2001), pp. 105-111.
Rossi and Zetter, "Selective stimulation of prostatic carcinoma cell proliferation by transferrin", Proceedings of the National Academy of Sciences of the United States of America, vol. 89 (1992), pp. 6197-6201.
Ruf et al., "Dynamic laser light scattering to determine size distributions of vesicles", Meth Enz, vol. 172 (1989), pp. 364-390.
Sang et al., "Proto-Oncogene Abnormalities and Their Relationship to Tumorigenicity in Some Human Glioblastomas", Journal of Neurosurgery, vol. 71 (1989), pp. 83-90.
Singh et al., "Identification of Human Brain Tumour Initiating Cells", Nature, vol. 432 (2004), pp. 396-401.
Son et al., "SSEA-1 Is an Enrichment Marker for Tumor-Initiating Cells in Human Glioblastoma", Cell Stem Cell, vol. 4 (2009), pp. 440-452.
Srivenugopal et al., "Enforced Expression of Wild-Type P53 Curtails the Transcription of the O6-Methylguanine-DNA Methyltransferase Gene in Human Tumor Cells and Enhances Their Sensitivity to Alkylating Agents", Clinical Cancer Research, vol. 7 (2001), pp. 1398-1409.
Staquicini et al., "Systemic Combinatorial Peptide Selection Yields a Non-Canonical Iron-Mimicry Mechanism for Targeting Tumors in a Mouse Model of Human Glioblastoma", Journal of Clinical Investigation, vol. 121 (2011), pp. 161-173.
Stupp et al., "Effects of Radiotherapy With Concomitant and Adjuvant Temozolomide Versus Radiotherapy Alone on Survival in Glioblastoma in a Radomised Phase III Study: 5-Year Analysis of the EORTC-NCIC Trial", Lancet Oncology, vol. 10 (2009), pp. 459-466.
Tentori and Graziani, "Recent Approaches to Improve the Antitumor Efficacy of Temozolomide", Current Medicinal Chemistry, vol. 16 (2009), pp. 245-257.
Thorstensen and Romslo, "The transferring receptor: its diagnostic value and its potential as therapeutic target", Scandinavian Journal of Clinical & Laboratory Investigation—Supplement, vol. 215 (1993), pp. 113-120.
Torres et al., "A Combined Preclinical Therapy of Cannabinoids and Temozolomide Against Glioma", Molecular Cancer Therapeutics, vol. 10 (2011), pp. 90-103.
Tran et al., "Survival Comparison Between Glioblastoma Multiforme and Other Incurable Cancers", Journal of Clinical Neuroscience, vol. 17 (2010), pp. 417-421.
Van Meir et al., "Analysis of the P53 Gene and Its Expression in Human Glioblastoma Cells", Cancer Research, vol. 54 (1994), pp. 649-652.
Villano et al., "Temozolomide in Malignant Gliomas: Current Use and Future Targets", Cancer Chemotherapy and Pharmacology, vol. 64 (2009), pp. 647-655.
Visvader and Lindeman, "Cancer Stem Cells in Solid Tumours: Accumulating Evidence and Unresolved Questions", Nat. Rev. Cancer, vol. 8 (2008), pp. 755-768.
Whitney et al., "Transferrin receptor expression in nonsmall cell lung cancer: histopathologic and clinical correlates", Cancer, vol. 76 (1995), pp. 20-25.

(56) References Cited

OTHER PUBLICATIONS

Xu et al., "Self-assembly of a virus-mimicking nanostructure system for efficient tumor-targeted gene delivery", Human Gene Therapy, vol. 13 (2002), pp. 469-481.

Xu et al., "Systemic p53 gene therapy of cancer with immunolipoplexes targeted by anti-transferrin receptor scFv", Molecular Medicine, vol. 7 (2001), pp. 723-724.

Xu et al., "Systemic tumor-targeted gene delivery by anti-transferrin receptor scFv-immunoliposomes", Molecular Cancer Therapeutics, vol. 1 (2002), pp. 227-346.

Xu et al., "Transferrin-liposome-mediated systemic p53 gene therapy in combination with radiation results in regression of human head and neck cancer xenografts", Human Gene Therapy, vol. 10 (1999), pp. 2941-2952.

Xu et al., "Tumor-targeted p53 gene therapy enhances the efficacy of conventional chemo/radiotherapy", Journal of Controlled Release, vol. 6 (2001), pp. 115-128.

Yang et al., "Nanomiiunoliposome Delivery of Suerparamagnetic Iron Oxide Markedly Enhances Targeting/Uptake in Human Cancer Cells In Vitro and In Vivo", Nanomedicine, vol. 4, Issue 4 (2008), pp. 318-329.

Yi et al., "Abnormal DNA Methylation of CD133 in Colorectal and Glioblastoma Tumors", Cancer Research, vol. 68 (2008), pp. 8094-8103.

You et al., "Epigenetic Regulation of Cancer Stem Cell Marker CD133 by Transforming Growth Factor-Beta", Hepatology, vol. 51 (2010), pp. 1635-1644.

Yu et al., "A sterically stabilized immunolipoplex for systemic administration of a therapeutic gene", Gene Therapy, vol. 11 (2004), pp. 1434-1440.

Yu et al., "Enhanced transfection efficiency of a systematically delivered tumor-targeting immunolipoplex by inclusion of a pH-sensitive histidylated oligolysine peptide", Nucleic Acids Research, vol. 32 (2004), pp. E48.

\* cited by examiner

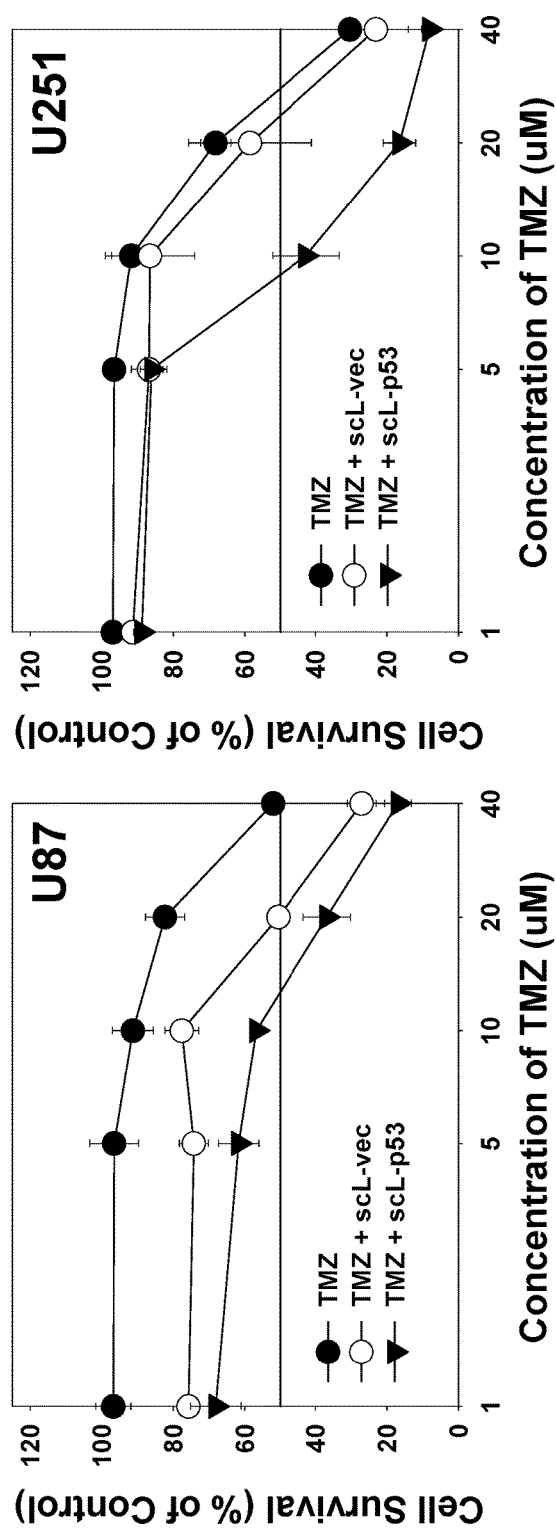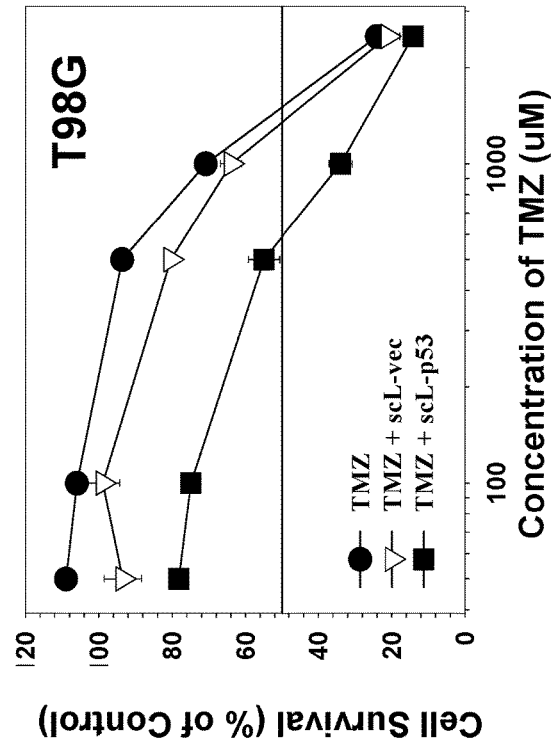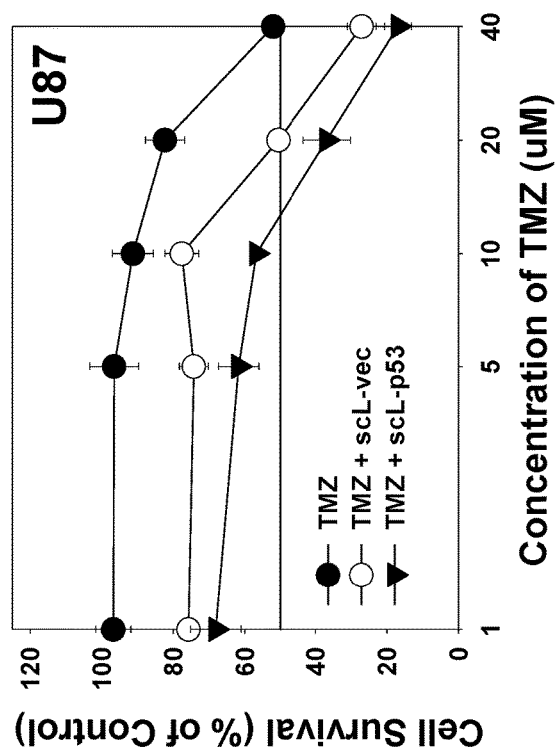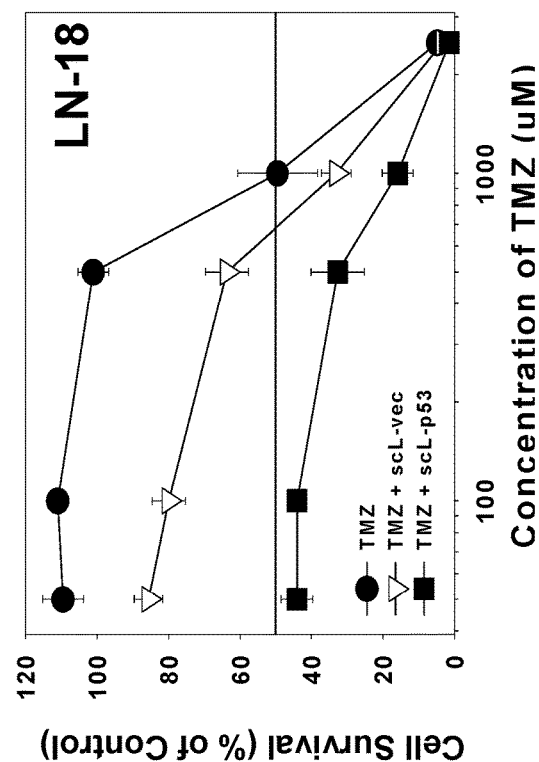
FIG. 23

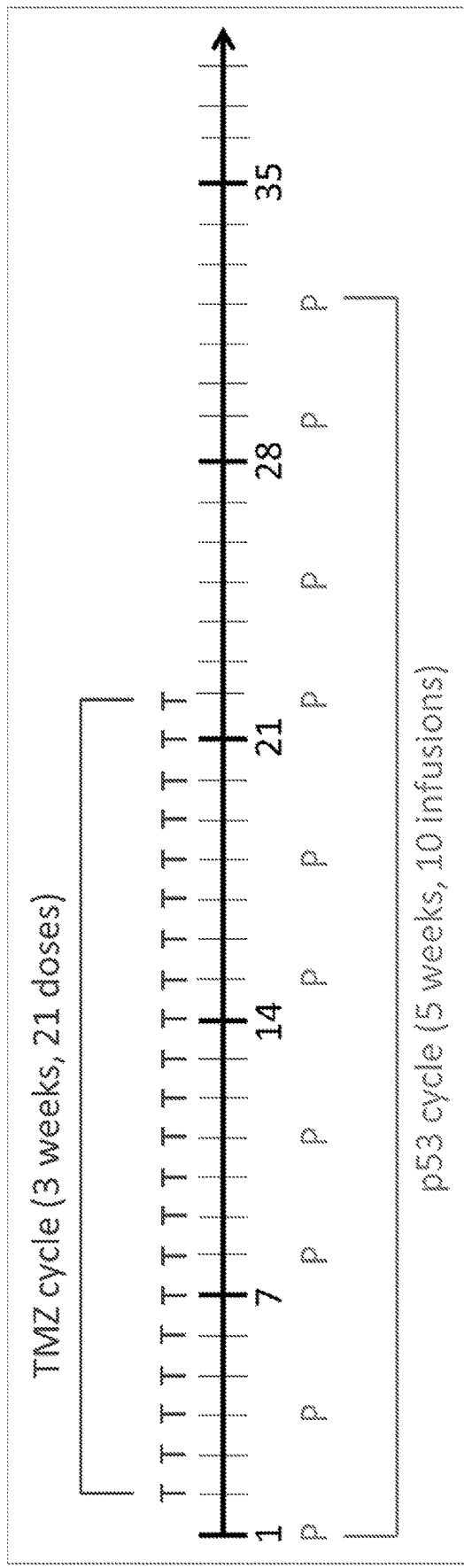

$^1$scL-p53 = Dose = 1.2 to 3.6 mg per infusion. scL-p53 to be given on Day 1. scL-p53 infusions should take place on Monday-Thursday or Tuesday-Friday of each week. In case of holiday or other logistic issues, schedule will allow for Tuesday-Thursday or Monday-Friday infusions of scL-p53. scL-p53 injections will end on Day 32 or after 10 infusions.

$^2$TMZ = Temozolomide treatment will begin on Day 2. Temozolomide will be administered orally at 100-250mg/m$^2$ everyday (including weekends) from Day 1 to Day 21.

FIG. 32

TARGETED LIPOSOMES

CROSS-REFERENCE TO RELATED APPLICATIONS

The present application is a divisional of U.S. application Ser. No. 14/030,563, filed Sep. 18, 2013, which claims the benefit of U.S. Provisional Patent Application Nos. 61/702,796, filed Sep. 19, 2012, and 61/767,453, filed Feb. 21, 2013, the disclosures of each of which are incorporated by reference herein in their entireties.

BACKGROUND OF THE INVENTION

Field of the Invention

The present invention is in the field of drug delivery, and specifically, cationic liposome-based drug delivery. In embodiments, this invention provides methods of making ligand-targeted (e.g., antibody- or antibody fragment-targeted) liposomes useful for the delivery of liposomes to tumors, including brain tumors. In embodiments, the liposomes deliver temozolomide across the blood-brain barrier for treatment of primary or metastatic brain tumors. Additional cancers that can be treated with the liposomes include, but are not limited to, neuroendocrine tumors, melanoma, prostate, head and neck, ovarian, lung, liver, breast, kidney, urogenital, gastric, colorectal, vaginal, cervical, liposarcoma, angiosarcoma, rhabdomyosarcoma, choriocarcinoma, pancreatic, retinoblastoma, multiple myeloma and other types of cancer. In another embodiment the liposomes deliver melphalan for the treatment of multiple myeloma, other tumors of the blood or other solid tumors. In still other embodiments the liposomes can deliver other drugs such as atropine, pemetrexed or irinotecan across the blood-brain barrier.

Background of the Invention

Primary brain tumors, and particularly gliomas, are one of the most difficult cancers to treat. In addition to primary tumors, metastatic brain cancer from a variety of primary sources [predominately lung (60%), breast (20%) and melanoma (10%)], is diagnosed in over 150,000 patients a year (Newton H and Malkin M (2010) Neurologic Complications of Systemic Cancer and Antineoplastic Therapy. Informa Healthcare). Thus, there is a critical need for improved therapies for brain cancers, which is confirmed by the fact that the NCI has made brain cancers one of its top 5 funding priorities. The lack of improvement in the prognosis of patients with brain cancer over the last few years, despite recent advances in drug discovery and development of targeted therapies, is due in large part to the inability of the therapeutics to cross the blood-brain barrier (BBB) (Blakeley, J. (2008): Drug delivery to brain tumors. Current Neurology & Neuroscience Reports, 8:235-241).

The current standard of therapy for glioblastoma multiforme (GBM) is surgical resection, followed by radiotherapy and chemotherapy with Temozolomide (TMZ). TMZ, a second-generation alkylating (methylating) agent causes cytotoxic DNA lesions, is also approved for treatment of anaplastic astrocytoma (AA) and is in clinical trials for treatment of brain metastases from other non-CNS solid tumors. The mechanism of action and pharmacological properties have been recently reviewed (Tentori L and Graziani G (2009) Recent Approaches to Improve the Antitumor Efficacy of Temozolomide. Current Medicinal Chemistry 16: pp 245-257; and Mrugala M M, Adair J and Kiem H P (2010) Temozolomide: Expanding Its Role in Brain Cancer. Drugs of Today 46: pp 833-846). TMZ is relatively well tolerated (Jiang G, Wei Z P, Pei D S, Xin Y, Liu Y Q and Zheng J N (2011) A Novel Approach to Overcome Temozolomide Resistance in Glioma and Melanoma: Inactivation of MGMT by Gene Therapy. Biochemical and Biophysical Research Communications 406: pp 311-314), however myelosuppression, neutropenia and thrombocytopenia are among its side effects and therapeutic dosages are limited by these. Extended TMZ dosing regimens were also found to provoke lymphocytopenia and opportunistic infections (Tentori L and Graziani G (2009) Recent Approaches to Improve the Antitumor Efficacy of Temozolomide. Current Medicinal Chemistry 16: pp 245-257). The extensive tissue distribution that results from the non-tumor specific uptake of the orally administered TMZ is a major cause of these side effects. Thus, tumor-targeting delivery of TMZ could help reduce these adverse events.

TMZ has shown survival benefit in a subset of GBM patients, however this median increase is only 2.5 months compared to radiation alone (Chamberlain M C (2010) Temozolomide: Therapeutic Limitations in the Treatment of Adult High-Grade Gliomas. Expert Review of Neurotherapeutics 10: pp 1537-1544). Recent studies have also indicated that 60-75% of GBM patients and 50% of AA patients do not benefit from TMZ (Chamberlain M C (2010) Temozolomide: Therapeutic Limitations in the Treatment of Adult High-Grade Gliomas. Expert Review of Neurotherapeutics 10: pp 1537-1544). The failure of chemotherapy can be attributed to a number of factors including, short half-life in circulation, efflux of drugs from the tumor by p-glycoprotein, resistance of the tumors to the drug and failure to cross the blood-brain barrier. The primary mechanism of resistance to TMZ is overexpression of $O^6$-methylguanine-DNA-methyl transferase (MGMT), which repairs the TMZ-induced DNA lesion by removing the $O^6$-guanine adducts (Mrugala M M, Adair J and Kiem H P (2010) Temozolomide: Expanding Its Role in Brain Cancer. Drugs of Today 46: pp 833-846). Thus, a means to down modulate MGMT activity, for example via the tumor specific delivery of the p53 tumor suppressor gene, would enhance the therapeutic effect of TMZ.

There is, therefore, an urgent need to develop new therapies for treatment of brain and other cancers. The present invention fulfills these needs by providing a cationic-liposome-based drug delivery system for delivery of temozolomide.

BRIEF SUMMARY OF THE INVENTION

In embodiments, methods of preparing a targeted temozolomide cationic liposome complex are provided. Such methods suitably comprise preparing a lipid solution comprising one or more cationic lipids in ethanol, preparing a solution of temozolomide, mixing the lipid solution with the solution of temozolomide, injecting the mixture of lipid and temozolomide into an aqueous solution, thereby forming a temozolomide cationic liposome, and mixing the temozolomide cationic liposome with a ligand to form the targeted temozolomide cationic liposome, wherein the ligand is directly complexed with, but not chemically conjugated to, the cationic liposome.

Suitably, the ligand is an antibody (targeted for example, but not limited to, to the Transferrin receptor, Folate receptor, HER-2 receptor, the vesicular glutamate transporter type 1 [VGluT1] receptor), an antibody fragment or a protein such as Transferrin or Folate, including a single chain Fv antibody fragment, such as an anti-transferrin receptor single chain Fv (TfRscFv).

Suitably the solution of temozolomide is prepared in dimethyl sulfoxide (DMSO). Suitably the solution of temozolomide is prepared at a concentration of about 1 mM to about 200 mM, or about 50 mM to about 200 mM.

In embodiments the lipid solution comprises 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol.

Suitably the molar ratio of lipid:Temozolomide, lipid:melphalan lipid:atropine or lipid:irinotecan is about 0.1:1 to about 5:1, more suitably about 0.5:1 to about 2:1 or about 1:1. Suitably the concentration of the liposome is about 1 mM to about 2 mM, or about 2 mM to about 10 mM In embodiments, the weight ratio of ligand:lipid is in the range of about 1:10 to about 1:50, suitably about 1:20 to about 1:40 (w:w). Suitably, the weight ratio of ligand:lipid is about 0.01:1 to about 0.05:1, more suitably about 0.03:1 to about 0.04:1. In embodiments the weight ratio of TfRscFv:lipid is about 0.033:1.

Suitably, a method of preparing a targeted temozolomide cationic liposome complex is provided. In embodiments, the methods comprise preparing a lipid solution comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol in ethanol, preparing a solution of Temozolomide in DMSO, water or other appropriate solvent such as a buffer solution such as a Phosphate buffer or a HEPES buffer or a TRIS buffer, mixing the lipid solution with the solution of temozolomide, injecting the mixture of lipid and temozolomide into an aqueous solution, thereby forming a temozolomide cationic liposome, mixing the temozolomide cationic liposome with an anti-transferrin receptor single chain Fv (TfRscFv) to form the targeted temozolomide cationic liposome complex, wherein the TfRscFv is directly complexed with, but not chemically conjugated to, the cationic liposome.

In another embodiment, a method of preparing a targeted melphalan cationic liposome complex is provided. In embodiments, the methods comprise preparing a lipid solution comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol in ethanol, preparing a solution of melphalan in DMSO, water or other appropriate solvent such as a buffer solution such as a Phosphate buffer or a HEPES buffer or a TRIS buffer, mixing the lipid solution with the solution of melphalan, injecting the mixture of lipid and melphalan into an aqueous solution, thereby forming a melphalan cationic liposome, mixing the melphalan cationic liposome with a ligand, including for example, an anti-transferrin receptor single chain Fv (TfRscFv), to form the targeted melphalan cationic liposome complex, wherein the ligand (e.g., TfRscFv) is directly complexed with, but not chemically conjugated to, the cationic liposome.

In another embodiment, a method of preparing a targeted atropine cationic liposome complex is provided. In embodiments, the methods comprise preparing a lipid solution comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol in ethanol, preparing a solution of atropine in ethanol, DMSO, water or other appropriate solvent such as a buffer solution such as a Phosphate buffer or a HEPES buffer or a TRIS buffer, mixing the lipid solution with the solution of atropine, injecting the mixture of lipid and atropine into an aqueous solution, thereby forming a atropin cationic liposome, mixing the atropine cationic liposome with a ligand, including for example, an anti-transferrin receptor single chain Fv (TfRscFv), to form the targeted atropine cationic liposome complex, wherein the ligand (e.g., TfRscFv) is directly complexed with, but not chemically conjugated to, the cationic liposome.

In another embodiment, a method of preparing a targeted irinitecan cationic liposome complex is provided. In embodiments, the methods comprise preparing a lipid solution comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol in ethanol, preparing a solution of irinotecan in ethanol, DMSO, water or other appropriate solvent such as a buffer solution such as a Phosphate buffer or a HEPES buffer or a TRIS buffer, mixing the lipid solution with the solution of irinotecan, injecting the mixture of lipid and irinotecan into an aqueous solution, thereby forming an irinotecan cationic liposome, mixing the irinotecan cationic liposome with a ligand, including for example, an anti-transferrin receptor single chain Fv (TfRscFv), to form the targeted atropine cationic liposome complex, wherein the ligand (e.g., TfRscFv) is directly complexed with, but not chemically conjugated to, the cationic liposome.

In further embodiments, methods of treating cancer in a patient, comprising administering to the patient a targeted temozolomide cationic liposome complex are provided. Suitably the targeted temozolomide cationic liposome complex comprises a cationic liposome comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol, temozolomide and a ligand complexed with, but not chemically conjugated to, the cationic liposome.

In further embodiments, methods of treating cancer in a patient, comprising administering to the patient a targeted melphalan cationic liposome complex are provided. Suitably, the targeted melphalan cationic liposome complex comprises a cationic liposome comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol, melphalan and a ligand complexed with, but not chemically conjugated to, the cationic liposome.

In further embodiments, methods of treating cancer in a patient, comprising administering to the patient a targeted atropine cationic liposome complex are provided. Suitably, the targeted atropine cationic liposome complex comprises a cationic liposome comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol, atropine and a ligand complexed with, but not chemically conjugated to, the cationic liposome.

In further embodiments, methods of treating cancer in a patient, comprising administering to the patient a targeted irinotecan cationic liposome complex are provided. Suitably, the targeted atropine cationic liposome complex comprises a cationic liposome comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol, irinotecan and a ligand complexed with, but not chemically conjugated to, the cationic liposome.

In embodiments, the administration is intravenous (IV), intratumoral (IT), intralesional (IL), aerosal, percutaneous, oral, endoscopic, topical, intramuscular (IM), intradermal (ID), intraocular (IO), intraperitoneal (IP), sublingual (SL), transdermal (TD), intranasal (IN), intracereberal (IC), intra-organ (e.g. intrahepatic), slow release implant, or subcutaneous administration, or via administration using an osmotic or mechanical pump Suitably the cancer being treated is a brain cancer, for example a glioma, glioblastoma or an astrocytoma.

In other embodiments, the cancer being treated is, but is not limited to, a primary or metastatic brain tumor, neuroendocrine tumors, melanoma, prostate, head and neck, ovarian, lung, kidney, liver, breast, vaginal, urogenital, gastric, colorectal, cervical, liposarcoma, angiosarcoma, rhabdomyosarcoma, choriocarcinoma, pancreatic, retinoblastoma, multiple myeloma and other types of cancer.

In another embodiment the liposomes deliver melphalan for the treatment of multiple myeloma.

In still other embodiments the liposomes can deliver other drugs such as atropine, pemetrexed or irinotecan and/or derivatives thereof.

In embodiments, the methods further comprise administering an additional therapy to the patient in combination with the targeted temozolomide, melphalan, atropine, premetrexed or irinotecan cationic liposome complex. Suitably the additional therapy comprises administration of a chemotherapeutic agent, a small molecule, radiation therapy or a nucleic acid-based therapy. In embodiments, the nucleic acid-based therapy comprises administration of a cationic liposome complex comprising a plasmid DNA expressing wild-type p53, or an oligonucleotide such as an siRNA, an miRNA or an shRNA. In embodiments the additional therapy comprises administration of any molecule that down-regulates, modifies or otherwise negates the effect of MGMT in the cancer cell. In additional embodiments the additional therapy comprises administration of any molecule that interferes with the production of acetylcholine, or binding of acetylcholine to its receptor.

In embodiments, methods of treating brain cancer in a patient, comprising administering to the patient a targeted temozolomide cationic liposome complex are provided. Suitably the targeted temozolomide cationic liposome complex comprises a cationic liposome comprising 1,2-dioleoyl-3-trimethylammonium propane (DOTAP) and 1,2-dioleoyl-sn-glycero-3-phosphoethanolamine (DOPE or a mixture of dimethyldioctadecylammonium bromide (DDAB) and DOPE, with or without cholesterol, temozolomide and an anti-transferrin receptor single chain Fv (TfRscFv) complexed with, but not chemically conjugated to, the cationic liposome.

Methods of treating cancer in a patient, are also provided, suitably comprising administering to the patient a targeted temozolomide cationic liposome complex or targeted inirotecan cationic liposome complex prepared by the methods described herein.

In still other embodiments, methods of treating multiple myeloma in a patient, comprising administering to the patient a targeted cationic liposome complex, are provided. Suitably the targeted melphalan cationic liposome complex comprises a cationic liposome comprising 1,2-dioleoyl-3-trimethylammonium propane (DOTAP) and 1,2-dioleoyl-sn-glycero-3-phosphoethanolamine (DOPE or a mixture of dimethyldioctadecylammonium bromide (DDAB) and DOPE, with or without cholesterol), melphalan and an anti-transferrin receptor single chain Fv (TfRscFv) directly complexed with, but not chemically conjugated to, the cationic liposome.

In still other embodiments, methods of treating any cancer in a patient, comprising administering to the patient a targeted cationic liposome complex are provided. Suitably the targeted melphalan cationic liposome complex comprises a cationic liposome comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol, melphalan and an anti-transferrin receptor single chain Fv (TfRscFv) directly complexed with, but not chemically conjugated to, the cationic liposome.

Methods of treating cancer in a patient, are also provided, suitably comprising administering to the patient a targeted melphalan cationic liposome complex prepared by the methods described herein.

Methods are also provided of treating a brain cancer in a patient, comprising administering to the patient a cationic liposome complex comprising a cationic liposome comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol, a plasmid DNA expressing wild-type p53 and an anti-transferrin receptor single chain Fv (TfRscFv) directly complexed with, but not chemically conjugated to, the cationic liposome; and temozolomide.

In still other embodiments, methods of treating any cancer in a patient, comprising administering to the patient a targeted cationic liposome complex are provided. Suitably the targeted irinotecan cationic liposome complex comprises a cationic liposome comprising 1,2-dioleoyl-3-trimethylammonium propane (DOTAP) and 1,2-dioleoyl-sn-glycero-3-phosphoethanolamine (DOPE) or a mixture of dimethyldioctadecylammonium bromide (DDAB) and DOPE, with or without cholesterol, irinotecan and an anti-transferrin receptor single chain Fv (TfRscFv) directly complexed with, but not chemically conjugated to, the cationic liposome.

Methods of treating cancer in a patient, are also provided, suitably comprising administering to the patient a targeted irinotecan cationic liposome complex prepared by the methods described herein.

Further embodiments, features, and advantages of the embodiments, as well as the structure and operation of the various embodiments, are described in detail below with reference to accompanying drawings.

BRIEF DESCRIPTION OF THE DRAWINGS/FIGURES

FIG. 23 shows XTT assay after the addition of the TMZ to the cells and $IC_{50}$ values.

FIG. 32 shows a proposed dosing schedule for scL-p53.

DETAILED DESCRIPTION OF THE INVENTION

Figure 1:
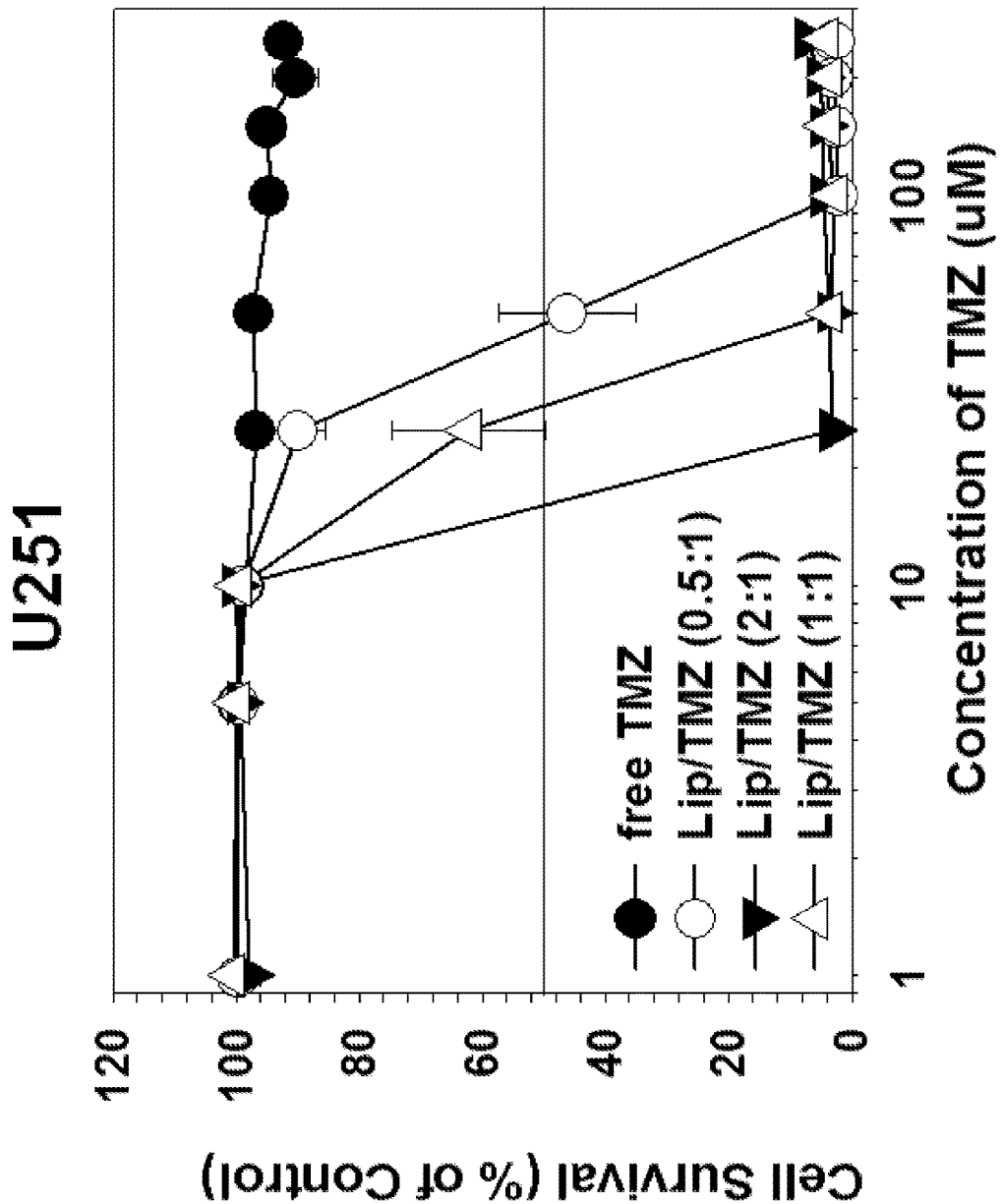
FIG. 1 shows U251 cell survival versus concentration of Temozolomide (TMZ) for free TMZ and three cationic liposomes comprising TMZ, as described herein.

It should be appreciated that the particular implementations shown and described herein are examples and are not intended to otherwise limit the scope of the application in any way.

The published patents, patent applications, websites, company names, and scientific literature referred to herein are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of ordinary skill in the art.

In embodiments, methods of preparing targeted temozolomide cationic liposome complexes are provided. Suitably, the methods comprise preparing a lipid solution comprising one or more cationic lipids in ethanol. A solution of temozolomide is prepared. The lipid solution is mixed with the solution of temozolomide. The mixture of cationic lipid and temozolomide is injected into an aqueous solution, thereby forming a temozolomide cationic liposome. The temozolomide cationic liposome is then mixed with a ligand to form the targeted temozolomide cationic liposome complex. Suitably, the ligand is directly complexed with, but not chemically conjugated to, the cationic liposome.

In embodiments, methods of preparing targeted melphalan cationic liposome complexes are provided. Suitably, the methods comprise preparing a lipid solution comprising one or more cationic lipids in ethanol. A solution of melphalan is prepared, suitably in absolute ethanol containing enough hydrochloric acid to facilitate dissolving the melphalan. The lipid solution is mixed with the solution of melphalan. The mixture of cationic lipid and melphalan is injected into an aqueous solution, thereby forming a melphalan cationic liposome. The melphalan cationic liposome is then mixed with a ligand to form the targeted melphalan cationic liposome complex. Suitably, the ligand is directly complexed with, but not chemically conjugated to, the cationic liposome.

In embodiments, methods of preparing targeted atropine, irinotecan or premetrexed cationic liposome complexes are provided. Suitably, the methods comprise preparing a lipid solution comprising one or more cationic lipids in ethanol. A solution of atropine, irinotecan or premetrexed is prepared in an appropriate solvent such as absolute ethanol, DMSO, water or a buffer solution such as a Phosphate buffer or a HEPES buffer or a TRIS buffer. The lipid solution is mixed with the solution of atropine, irinotecan or premetrexed. The mixture of cationic lipid and atropine, irinotecan or premetrexed is injected into an aqueous solution, thereby forming a cationic atropine, irinotecan or premetrexed liposome. The atropine, irinotecan or premetrexed cationic liposome is then mixed with a ligand to form the targeted atropine, irinotecan or premetrexed cationic liposome complex. Suitably, the ligand is directly complexed with, but not chemically conjugated to, the cationic liposome.

The terms "complex," "nanocomplex," "liposome complex" and "cationic liposome complex" and "cationic immunoliposome complex" are used interchangeably throughout to refer to the cationic liposomes of the present invention.

Described throughout are various active agents that can be encapsulated in the liposome complexes described. It is to be understood that derivates of such active agents (e.g., hydrochloride salts as well as other derivates) are also encompassed by the disclosure.

As described herein, temozolomide is a second-generation alkylating (methylating) agent causes cytotoxic DNA lesions, and is also approved for treatment of anaplastic astrocytoma (AA). The structure of temozolomide shown below, has an empirical formula: $C_6H_6N_6O_2$.

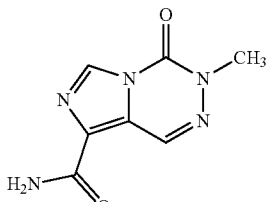

Temozolomide,
MW = 194.15

In embodiments, a salt of temozolomide, e.g., an HCl salt, can also be used in the methods described herein.

Suitably, the solution of temozolomide (TMZ) is prepared in dimethyl sulfoxide (DMSO) or other appropriate solvent. The solution of TMZ can be prepared at any desired concentration. In embodiments, the concentration of TMZ in the solution is about 0.1 mM to about 500 mM, more suitably about 1 mM to about 200 mM, about 50 mM to about 200 mM, about 50 mM to about 100 mM, or about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, or about 200 mM.

Melphalan is an antineoplastic agent belonging to the class of nitrogen mustard alkylating agents. An alkylating agent adds an alkyl group ($C_nH_{2n+1}$) to DNA. It attaches the alkyl group to the guanine base of DNA, at the number 7 nitrogen atom of the imidazole ring. The structure of melphalan shown below, has an empirical formula: $C_{13}H_{18}Cl_2N_2O_2$.

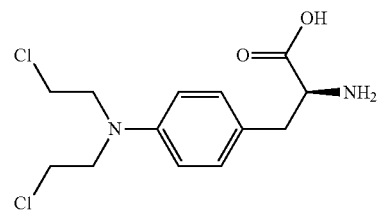

Mephalan,
MW = 305.20

Suitably, the solution of melphalan is prepared in absolute ethanol containing enough hydrochloric acid to facilitate dissolving the melphalan or other appropriate solvent. The solution of melphalan can be prepared at any desired concentration. In embodiments, the concentration of melphalan in the solution is about 0.1 mM to about 500 mM, more suitably about 1 mM to about 200 mM, about 50 mM to about 200 mM, about 50 mM to about 100 mM, or about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, or about 200 mM.

Irinotecan is the hydrochloride salt of a semisynthetic derivative of camptothecin, a cytotoxic, quinoline-based alkaloid extracted from the Asian tree *Camptotheca acuminata*. Irinotecan, a prodrug, is converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death. Because ongoing DNA synthesis is necessary for irinotecan to exert its cytotoxic effects, it is classified as an S-phase-specific agent. Empirical Formula (Hill Notation) $C_{33}H_{38}N_4O_6$

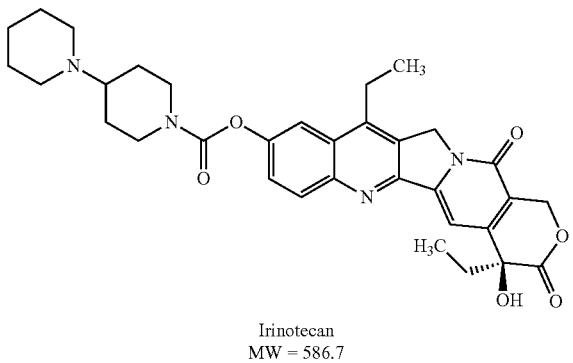 [SMILES: CCc1c2c(nc3ccc(OC(=O)N4CCC(N5CCCCC5)CC4)cc13)-c1cc3c(c(=O)n1C2)COC(=O)[C@]3(O)CC]

Irinotecan
MW = 586.7

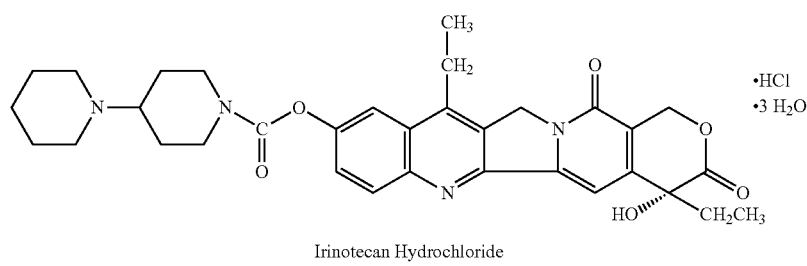 [SMILES: CCc1c2c(nc3ccc(OC(=O)N4CCC(N5CCCCC5)CC4)cc13)-c1cc3c(c(=O)n1C2)COC(=O)[C@@]3(O)CC]

Irinotecan Hydrochloride

The terms "ironotecan" and "irinotecan hydrochloride" are used interchangeably throughout.

Suitably, the solution of irinotecan is prepared in DMSO or other appropriate solvent. The solution of irinotecan can be prepared at any desired concentration. In embodiments, the concentration of irinotecan in the solution is about 0.1 mM to about 500 mM, more suitably about 1 mM to about 200 mM, about 50 mM to about 200 mM, about 50 mM to about 100 mM, or about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, or about 200 mM.

Suitably, the solution of atropine or premetrexed is prepared in an appropriate solvent such as absolute ethanol, DMSO, water or a buffer solution such as a Phosphate buffer or a HEPES buffer or a TRIS buffer. The solution of atropine, or premetrexed can be prepared at any desired concentration. In embodiments, the concentration of atropine, or premetrexed in the solution is about 0.1 mM to about 500 mM, more suitably about 1 mM to about 200 mM, about 50 mM to about 200 mM, about 50 mM to about 100 mM, or about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, or about 200 mM.

A wide variety of lipids are useful in the methods described herein. Published PCT application WO 99/25320 describes the preparation of several cationic liposomes. Examples of suitable lipids include phosphatidylcholine (PC), phosphatidylserine (PS), as well as mixtures of dioleoyltrimethylammonium propane (DOTAP) and dioleoylphosphatidylethanolamine (DOPE) and/or cholesterol (chol); a mixture of dimethyldioctadecylammonium bromide (DDAB) and DOPE with or without cholesterol. The ratio of the lipids can be varied to optimize the efficiency of loading of the TMZ, melphalan, atropine, pemetrexed or irinotecan and uptake in the specific target cell type. The liposome can comprise a mixture of one or more cationic lipids and one or more neutral or helper lipids. A desirable ratio of cationic lipid(s) to neutral or helper lipid(s) is about 1:(0.5-3), preferably 1:(1-2) (molar ratio). Exemplary lipids for use in preparing the cationic liposomes described herein are well known in the art and include, for example, 1,2-dioleoyl-3-trimethylammonium propane (DOTAP) and 1,2-dioleoyl-sn-glycero-3-phosphoethanolamine (DOPE).

Examples of ratios of various lipids useful in the practice of methods described herein include, but are not limited, to:

| LipA | DOTAP/DOPE | 1:1 molar ratio |
|---|---|---|
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

(DOTAP=1,2-dioleoyl-3-trimethyl ammonium propane, DDAB=dimethyldioctadecylammonium bromide; DOPE=dioleoylphosphatidylethanolamine; chol=cholesterol).

As described herein, the lipids are suitably prepared in ethanol (e.g., absolute ethanol) prior to preparing the complexes described herein.

Following solubilization in ethanol of the lipid components of the complexes, the appropriate amount of TMZ, melphalan atropine, irinotecan or premetrexed, dissolved in DMSO, ethanol, hydrochloric acid or other suitable solvent such as a buffer solution such as a Phosphate buffer or a HEPES buffer or a TRIS buffer, is added to the lipid mixture. Suitably, the lipid mixture is maintained at a temperature of about 50-60° C., prior to and during the addition of the TMZ, melphalan, atropine, irinotecan or premetrexed.

To prepare the liposomes, the solution of lipids and TMZ, melphalan, atropine, irinotecan or premetrexed is injected into an aqueous solution to form the liposomes. As used herein "injected" means to force or drive the solution of lipids and TMZ, melphalan, atropine, irinotecan or premetrexed into an aqueous solution. Suitably, the aqueous solution is water, though additional buffers and salts can be present in the aqueous solution. In embodiments, the aqueous solution is endotoxin free LAL reagent water (suitably having an endotoxin content of <0.005 EU/ml) (BioWhittaker). Suitably the injection is carried out utilizing a syringe or similar device to produce the liposomes. In embodiments, the aqueous solution is stirred rapidly during addition of the lipid/TMZ, melphalan, atropine, irinotecan or premetrexed solution so as to facilitate liposome formation.

It has been unexpectedly found that no extrusion or sonication is required to form the liposomes having the desired size and Zeta Potential characteristics, according to the methods described herein. In embodiments, evaporation, sonication, milling and/or extrusion of the liposomes is specifically excluded from the disclosed methods. In further embodiments, the methods of preparing targeted cationic liposomes described throughout suitably consist of or consist essentially of the recited elements. In such embodiments, addition of steps such as evaporation, sonication and/or extrusion, are considered a material alteration to such methods and thus are specifically excluded from such methods that consist essentially of the recited elements.

Preparation of liposomes by mixing the lipids (in Chloroform) together, evaporating to dryness and reconstituting with water containing the drug in solution (a common procedure for liposome encapsulation of drugs), did not produce a homogeneous population. Measurement by light scattering gave poor results, with the quality report indicating that the cumulant fit error was high, thus the data quality was too poor for cumulant analysis, and the sample too polydisperse for cumulant analysis. The Z-Average (d-nm) for this preparation was 743.9 nm (number average).

The temozolomide, melphalan, atropine, irinotecan or premetrexed cationic liposomes formed according to the injection methods described herein are then mixed with a ligand to form the targeted temozolomide, melphalan, atropine, irinotecan or premetrexed cationic liposomes. As described throughout, the ligand is directly complexed with, but not chemically conjugated to, the cationic liposome. In other embodiments, the ligand can be chemically conjugated to the cationic liposome.

As used herein the term "ligand" refers to any suitable targeting moiety that can be either chemically conjugated to, or directly associated/complexed with, but not chemically conjugated to, the cationic liposomes. In embodiments where the ligand is directly associated/complexed with, but not chemically conjugated to the cationic liposomes, no linker, spacer or other bridging molecule is used to complex the ligands to the liposomes. Exemplary ligands for use in the practice of the present invention include, but are not limited to, proteins (e.g., transferrin or folate), peptides (e.g., L-37 pA), antibodies, antibody fragments (including Fab' fragments and single chain Fv fragments (scFv)) and sugars (e.g., galactose), as well as other targeting molecules.

In exemplary embodiments, a whole antibody or an antibody fragment can be used as the ligand to make the complexes of this invention. In a suitable embodiment, an antibody fragment is used, including Fab fragments and single chain Fv fragments (scFv) of an antibody. One suitable antibody is an anti-Transferrin receptor (anti-TfR) monoclonal antibody, and a suitable antibody fragment is an scFv based on an anti-TfR monoclonal antibody (TfRscFv). An scFv contains the complete antibody binding site for the epitope of the UR recognized by this MAb as a single polypeptide chain of approximate molecular weight 26,000. An scFv is formed by connecting the component VH and VL variable domains from the heavy and light chains, respectively, with an appropriately designed peptide, which bridges the C-terminus of the first variable region and N-terminus of the second, ordered as either VH-peptide-VL or VL-peptide-VH. Additional ligands, such as those described throughout, can also be used in the practice of the present invention.

In one embodiment, a cysteine moiety is added to the C-terminus of the scFv. Although not wishing to be bound by theory, it is believed that the cysteine, which provides a free sulfhydryl group, may enhance the formation of the complex between the antibody and the liposome in both the chemically conjugated and non-chemically conjugated embodiments. With or without the cysteine, the protein can be expressed in E. coli inclusion bodies and then refolded to produce the antibody fragment in active form.

Suitable ligands, for example, proteins/peptides, antibody or antibody fragments, are those which will bind to the surface of the target cell, and preferably to a receptor that is differentially expressed on the target cell. The ligands are mixed with the cationic liposome at room temperature and at a ligand (e.g., protein, antibody or antibody fragment): lipid ratio (weight:weight) in the range of about 1:10 (0.1:1) to about 1:50, suitably about 1:20 to about 1:40 (w:w). Suitably, the weight ratio of ligand:lipid is about 0.1:10 to about 0.5:10, about 0.3:10 to about 0.4:10, or about 0.33:10, including any ratio within these ranges. The ligand (e.g., the protein/peptide, antibody or antibody fragment) and the liposome are allowed to incubate at room temperature for a short period of time, typically for about 10-15 minutes.

The size of the liposome complex is typically within the range of about 5-1000 nm as measured by dynamic light scattering using a Malvern ZETASIZER® 3000 or a Malvern ZETASIZER® NANO-ZS. See U.S. Published Patent Application No. 2003/0044407 and U.S. patent application Ser. No. 11/520,796, the disclosures of which are incorporated by reference herein in their entireties. The size of the liposomes is demonstrated by a single peak, representing a homogenous size population. More suitably, the size of the liposome complex prior to the addition of the ligand is in the range of about 5 nm to about 500 nm, about 5 nm to about 300 nm, about 5 nm to about 200 nm, about 5 nm to about 100 nm, about 10 nm to about 70 nm, or about 20 nm to about 60 nm. The size of the liposome complex following addition of the ligand is suitably in the range of about 5 nm to about 800 nm, about 10 nm to about 500 nm, about 20 nm to about 400 nm, about 20 nm to about 200 nm, or about 30 nm to about 200 nm.

Suitably the liposomes described herein have a positive Zeta Potential. Suitably the Zeta Potential of the liposomes prior to the addition of the ligand are about 1 mV to about 200 mV, about 1 mV to about 100 mV, about 10 mV to about 100 mV, about 20 mV to about 60 mV, or about 30 mV to about 50 mV. Suitable the Zeta Potential of the liposomes following the addition of the ligand are about 1 mV to about 200 mV, about 1 mV to about 100 mV, about 10 mV to about 80 mV, about 10 mV to about 60 mV, or about 25 mV to about 50 mV.

In embodiments, liposomes used to form the complex as described herein are sterically stabilized liposomes. Sterically stabilized liposomes are liposomes into which a hydrophilic polymer, such as PEG, poly(2-ethylacrylic acid), or poly(n-isopropylacrylamide (PNIPAM) has been integrated. Such modified liposomes can be particularly useful, as they typically are not cleared from the bloodstream by the reticuloendothelial system as quickly as are comparable liposomes that have not been so modified. To make a sterically stabilized liposome complex of the present invention, a cationic liposome comprising temozolomide, melphalan, atropine, irinotecan or premetrexed is prepared as above. To this liposome is added a solution of a PEG polymer in a physiologically acceptable buffer at a ratio of about 0.1:100 (nmol of PEG:nmol of liposome), suitably, about 0.5:50, for example, about 1:40 (nmol of PEG:nmol of liposome). The resultant solution is incubated at room temperature for a time sufficient to allow the polymer to integrate into the liposome complex. The ligand (e.g., protein/peptide, antibody or antibody fragment) then is mixed with the stabilized liposome complex at room temperature and at a ligand (e.g., protein):lipid ratio in the range of about 1:5 to about 1:40 (w:w).

As described herein, the ligand (e.g., protein/peptide, antibody or antibody fragment) is suitably directly associated (complexed) with the liposome via an interaction (e.g., electrostatic, van der Walls, or other non-chemically conjugated interaction) between the ligand and the liposome. In general, a linker or spacer molecule (e.g., a polymer or other molecule) is not used to attach the ligands and the liposome when non-chemically conjugated.

As described herein, in additional embodiments, the ligand (e.g., protein/peptide, antibody or antibody fragment) is chemically conjugated to the cationic liposomes, for example, via a chemical interaction between the cationic liposome which contains a maleimidyl group or other sulfhydryl-reacting group, and a sulfur atom on the ligand (e.g., protein/peptide, antibody or antibody fragment). Such methods of direct chemical conjugation are disclosed in U.S. patent application Ser. No. 09/914,046, filed Oct. 1, 2001, the disclosure of which is incorporated by reference herein in its entirety.

Suitable ratios of lipid:temozolomide for use in the methods and liposomes are described throughout. In exemplary embodiments, the molar ratio of lipid:temozolomide is about 0.1:1 to about 1:100, about 0.05:1 to about 1:50, about 1:1 to about 1:20, about 2:1 to about 10:0.1, about 0.5:1 to about 2:1, or about 1:1.

Suitable ratios of lipid:melphalan for use in the methods and liposomes are described throughout. In exemplary embodiments, the molar ratio of lipid:melphalan is about 0.1:1 to about 1:100, about 0.5:1 to about 1:50, about 1:1 to about 1:20, about 2:1 to about 10:0.1, about 0.5:1 to about 2:1, or about 1:1.

Suitable ratios of lipid:atropine, irinotecan or premetrexed for use in the methods and liposomes are described throughout. In exemplary embodiments, the molar ratio of lipid:atropine, irinotecan or premetrexed is about 0.1:1 to about 1:100, about 0.5:1 to about 1:50, about 1:1 to about 1:20, about 2:1 to about 10:0.1, about 0.5:1 to about 2:1, or about 1:1.

Encapsulation efficiency for the TMZ liposomes is suitably in the range of about 20% to about 100%, about 20% to about 80%, about 20% to about 60%, or about 30% to about 55%, encapsulated TMZ. This is a surprising and unexpected result of the ethanol injection method for encapsulating TMZ in the liposomes.

Encapsulation efficiency for the melphalan liposomes is suitably in the range of about 20% to about 100%, about 20% to about 80%, about 20% to about 60%, or about 20% to about 40%, encapsulated melphalan. This is a surprising an unexpected result of the ethanol injection method for encapsulating melphalan in the liposomes.

Encapsulation efficiency for the atropine, irinotecan or premetrexed liposomes is suitably in the range of about 20% to about 100%, about 20% to about 80%, about 20% to about 60%, or about 20% to about 40%, encapsulated atropine, irinotecan or premetrexed. This is a surprising an unexpected result of the ethanol injection method for encapsulating atropine, irinotecan or premetrexed in the liposomes.

In additional embodiments, the liposomes can also comprise endosomal disrupting peptides, such as the K[K(H)KKK]$_5$-K(H)KKC (HoKC) (HK) (SEQ ID NO: 1) peptide manufactured by Sigma-Genosys (The Woodlands, Tex.), associated with the liposomes. The endosomal disrupting peptide HoKC may help the release of TMZ, melphalan, atropine, pemetrexed or irinotecan from the endosomes into the cytoplasm of the cells. In such embodiments, the liposomes suitably also comprise MPB-DOPE at 5 molar percent of total lipid. Since the HoKC peptide (K[K(H)KKK]$_5$-K(H)KKC) carries a terminal cysteine, MPB-DOPE is included to allow conjugation of the peptide to the liposome. The Lip-HoKC liposomes were prepared using the coupling reaction between the cationic liposomes carrying the maleimide group (Lip-MPB) and the peptide. An aliquot of 0.1 mmol of the peptide with a free thiol group on cysteine was added to 2 mmol of Lip-MPB in 10 mM HEPES, pH 7.4, solution and rotated at room temperature (20-30 r.p.m.) for 2 h.

The liposomal complexes prepared in accordance with the present invention can be formulated as a pharmacologically acceptable formulation for in vivo administration. The complexes can be combined with a pharmacologically compatible vehicle or carrier. The compositions can be formulated, for example, for intravenous administration to a mammal, for example a human patient to be benefited by administration of the TMZ, melphalan, atropine, irinotecan or premetrexed in the complex. The complexes have an inherent size so that they are distributed throughout the body following i.v. administration. Alternatively, the complexes can be delivered via other routes of administration, such as intratumoral (IT), intralesional (IL), sublingual (SL), aerosal, percutaneous, oral, endoscopic, topical, intramuscular (IM), intradermal (ID), intraocular (IO), intraperitoneal (IP), transdermal (TD), intranasal (IN), intracereberal (IC), intraorgan (e.g. intrahepatic), slow release implant, or subcutaneous administration, or via administration using an osmotic or mechanical pump. Preparation of formulations for delivery via such methods, and delivery using such methods, are well known in the art.

The complexes can be optimized for target cell type through the choice and ratio of lipids, the ratio of ligand (e.g., protein/peptide, antibody or antibody fragment) to liposome, the ratio of ligand and liposome to TMZ, melphalan, atropine, irinotecan or premetrexed and the choice of ligand.

The complexes made in accordance with the methods of this invention can be provided in the form of kits for use in the delivery of TMZ, melphalan, atropine, irinotecan or premetrexed. Suitable kits can comprise, in separate, suitable containers, the targeted TMZ, melphalan, atropine, irinotecan or premetrexed cationic liposome complexes (suitably dried, lyophilized powders) and water or a suitable buffer. The components can be mixed under sterile conditions in the appropriate order and administered to a patient within a reasonable period of time, generally from about 30 minutes to about 24 hours, after preparation. Liposomes are suitably prepared in sterile water-for-injection, along with appropriate buffers, osmolarity control agents, etc. The complete complex is suitably formulated as a dried powder (lyophilized) (see, e.g., U.S. Published Patent Application No. 2005/0002998, the disclosure of which is incorporated by reference herein in its entirety).

The cationic liposome complexes of the present invention suitably comprise an anti-transferrin receptor single chain antibody molecule (TfRscFv) on their surface. It has been determined that this targeting molecule enhances delivery across the blood-brain barrier and targeted delivery to brain cancer cells. The targeted liposomes can also be used to treat other cancers in the body and to deliver other drugs.

Also provided are cationic liposome complexes prepared according to the methods described throughout. For example, ligand-targeted (e.g., protein/peptide, antibody- or antibody fragment-targeted) cationic liposome complexes comprising a cationic liposome, a ligand (e.g., protein/peptide, antibody or antibody fragment), and TMZ, melphalan, atropine, pemetrexed or irinotecan, wherein the ligand is directly complexed/associated with, but not chemically conjugated to the cationic liposome, are provided.

The TMZ, melphalan, atropine, irinotecan or premetrexed can be encapsulated within the cationic liposome (i.e., in the hydrophilic, aqueous interior of the liposomes), contained within a hydrocarbon chain region of the cationic liposome, associated with an inner or outer monolayer of the cationic liposome (e.g., the head-group region), or any combination thereof. Suitably, the cationic liposomes of the present invention are unilamellar liposomes (i.e. a single bilayer), though multilamellar liposomes which comprise several concentric bilayers can also be used. Single bilayer cationic liposomes of the present invention comprise an interior aqueous volume in which TMZ, melphalan, atropine, irinotecan or premetrexed can be encapsulated. They also comprise a single bilayer which has a hydrocarbon chain region (i.e., the lipid chain region of the lipids) in which TMZ, melphalan, atropine, irinotecan or premetrexed can be contained. In addition, TMZ, melphalan, atropine, irinotecan or premetrexed can be complexed or associated with either, or both, the inner monolayer and/or the outer monolayer of the liposome membrane (i.e., the head-group region of the lipids). In further embodiments, TMZ, melphalan, atropine, irinotecan or premetrexed can be encapsulated/associated/complexed in any or all of these regions of the cationic liposome complexes of the present invention.

In further embodiments, pharmaceutical compositions comprising the ligand-targeted cationic liposome complexes described throughout are provided. In suitable embodiments, the pharmaceutical compositions further comprise one or more excipients selected from the group consisting of one or more antibacterials (e.g., amphotericin B, chloretracycline, gentamicin, neomycin), one or more preservatives (e.g., benzethonium chloride, EDTA, formaldehyde, 2-phenoxyethanol), one or more buffers (e.g., phosphate buffers, sodium borate, sodium chloride), one or more surfactants (polysorbate 20, 80), one or more protein stabilizers (e.g., albumin, lactose, potassium glutamate), sugars e.g. sucrose or dextrose, and adjuvants (e.g., aluminum hydroxide, aluminum phosphate). Additional excipients are well known in the art and can be readily used in the practice of the present invention.

Also provided are pharmaceutical compositions comprising a first ligand-targeted cationic liposome complex comprising a cationic liposome, a ligand (e.g., protein/peptide, antibody or antibody fragment), and TMZ, melphalan, atropine, irinotecan or premetrexed wherein the ligand is directly complexed/associated with, but not chemically conjugated to the cationic liposome. In further embodiments, the ligand can be chemically conjugated to the cationic liposome. The pharmaceutical compositions also suitably comprise a second different ligand-targeted cationic liposome complex comprising a cationic liposome, a ligand (e.g., protein/peptide, antibody or antibody fragment), and one or more nucleic acid molecules (including plasmid DNA, siRNA, miRNA, shRNA or antisense nucleic acids), wherein the ligand is directly complexed/associated with, but not chemically conjugated to the cationic liposome. (See U.S. Pat. No. 7,780,822 and US Published Patent Application No. 2007/0065449, the disclosures of which are incorporated by reference herein in their entireties). In further embodiments, the compositions can also comprise a ligand-targeted cationic liposome complex comprising a ligand (e.g., protein/peptide, antibody or antibody fragment), and one or more small molecules (see U.S. Published Patent Application No. 2007/0231378, the disclosure of which is incorporated by reference herein in its entirety) or one or more imaging agents (see U.S. Published Patent Application No. 2007/0134154, the disclosure of which is incorporated by reference herein in its entirety), wherein the ligand is directly complexed/associated with, but not chemically conjugated to the cationic liposome. In further embodiments, the ligand can be chemically conjugated to the cationic liposome in such compositions.

Also provided are pharmaceutical compositions comprising a first ligand-targeted cationic liposome complex comprising a cationic liposome, a ligand (e.g., protein/peptide, antibody or antibody fragment), and TMZ, melphalan, atropine, irinotecan or premetrexed wherein the ligand is directly complexed/associated with, but not chemically conjugated to the cationic liposome. In further embodiments, the ligand can be chemically conjugated to the cationic liposome. The pharmaceutical compositions also suitably comprise a second ligand-targeted cationic liposome complex comprising a cationic liposome, a ligand (e.g., protein/peptide, antibody or antibody fragment), and one or more nucleic acid molecules (including plasmid DNA, siRNA, miRNA, shRNA or antisense nucleic acids), one or more small molecules, or one or more imaging agents (including superparamagnetic iron oxide, or gadolinium) wherein the nucleic acid molecules, small molecules, or imaging agents down-regulates, modifies or otherwise negates the effect of MGMT in the cancer cell.

In further embodiments, methods of treating cancer in a patient are provided. Suitably, such methods comprise administering to a patient one or more of the targeted cationic liposome complexes as described herein. Suitably the complexes are prepared according to the methods described throughout.

In embodiments, the methods of treatment comprise administering to a patient a targeted Temozolomide, irinotecan or melphalan cationic liposome complex, wherein the cationic liposome complex comprises a cationic liposome comprising 1,2-dioleoyl-3-trimethylammonium propane (DOTAP) and 1,2-dioleoyl-sn-glycero-3-phosphoethanolamine (DOPE) or comprising dimethyldioctadecylammonium bromide (DDAB) and DOPE, with or without cholesterol, Temozolomide, irinotecan or melphalan, and a ligand complexed with, but not chemically conjugated to, the cationic liposome.

As described throughout, the ligand is suitably an antibody, an antibody fragment or a protein, including a single chain Fv antibody fragment. In exemplary embodiments, the single chain Fv antibody fragment is an anti-transferrin receptor single chain Fv (TfRscFv).

Also provided of methods of treating organophosphate poisoning (i.e., nerve gas poisoning) in a patient, comprising administering to the patient a targeted atropine cationic liposome complex, wherein the targeted atropine cationic liposome complex comprises cationic liposome comprising 1,2-dioleoyl-3-trimethylammonium propane (DOTAP) and 1,2-dioleoyl-sn-glycero-3-phosphoethanolamine (DOPE), atropine and a ligand directly complexed with, but not chemically conjugated to, the cationic liposome. Exemplary ligands are described herein.

Suitably the temozolomide is administered to the patients utilizing the methods described herein at a dose of about 1 mg/m$^2$ to about 1000 mg/m$^2$, more suitably at a dose of about 10 mg/m$^2$ to about 500 mg/m$^2$, or about 50 mg/m$^2$ to about 400 mg/m$^2$, about 80 mg/m$^2$ to about 300 mg/m$^2$, about 50 mg/m$^2$ to about 250 mg/m$^2$, about 50 mg/m$^2$ to about 250 mg/m$^2$, or about 50 mg/m$^2$, about 60 mg/m$^2$, about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, about 250 mg/m$^2$, about 260 mg/m$^2$, about 270 mg/m$^2$, about 280 mg/m$^2$, about 290 mg/m$^2$, or about 300 mg/m$^2$.

Suitably the melphalan is administered to the patients utilizing the methods described herein at a dose of about 1 mg/m$^2$ to about 500 mg/m$^2$, more suitably at a dose of about 1 mg/m$^2$ to about 100 mg/m$^2$, or about 1 mg/m$^2$ to about 50 mg/m$^2$, about 1 mg/m$^2$ to about 30 mg/m$^2$, about 5 mg/m$^2$ to about 20 mg/m$^2$, or about 6 mg/m$^2$ to about 16 mg/m$^2$, or about 1 mg/m$^2$, about 2 mg/m$^2$, about 3 mg/m$^2$, about 4 mg/m$^2$, about 5 mg/m$^2$, about 6 mg/m$^2$, about 7 mg/m$^2$, about 8 mg/m$^2$, about 9 mg/m$^2$, about 10 mg/m$^2$, about 11 mg/m$^2$, about 12 mg/m$^2$, about 13 mg/m$^2$, about 14 mg/m$^2$, about 15 mg/m$^2$, about 16 mg/m$^2$, about 17 mg/m$^2$, about 18 mg/m$^2$, about 19 mg/m$^2$, about 20 mg/m$^2$, about 21 mg/m$^2$, about 22 mg/m$^2$, about 23 mg/m$^2$, about 24 mg/m$^2$, or about 25 mg/m$^2$.

Suitably the, irinotecan or premetrexed is administered to the patients utilizing the methods described herein at a dose of about 1 mg/m$^2$ to about 1000 mg/m$^2$, more suitably at a dose of about 10 mg/m$^2$ to about 500 mg/m$^2$, or about 50 mg/m$^2$ to about 400 mg/m$^2$, about 80 mg/m$^2$ to about 300 mg/m$^2$, about 100 mg/m$^2$ to about 250 mg/m$^2$, or about 50 mg/m$^2$, about 60 mg/m$^2$, about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, about 250 mg/m$^2$, about 260 mg/m$^2$, about 270 mg/m$^2$, about 280 mg/m$^2$, about 290 mg/m$^2$, or about 300 mg/m$^2$.

In embodiments, the atropine is administered to the patients (suitably intramuscularly) utilizing the methods described herein at a dose of about 0.01 mg to about 100 mg, more suitably at a dose of about 0.1 mg to about 50 mg, or about 1 mg to about 40 mg, about 1 mg to about 30 mg, about 1 mg to about 20 mg, about 1 mg to about 10 mg, about 2 mg to about 6 mg, or about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg or about 20 mg.

As described herein, in embodiments, the molar ratio of lipid in the cationic liposome:temozolomide, melphalan, atropine, irinotecan or premetrexed for use in the methods described herein is about 0.1:1 to about 5:1. More suitably, the molar ratio of lipid in the cationic liposome:temozolomide, melphalan, atropine, irinotecan or premetrexed is about 0.1:1 to about 1:100, about 0.5:1 to about 1:50, about 1:1 to about 1:20, about 2:1 to about 10:0.1, about 0.5:1 to about 2:1, or about 1:1.

The weight ratio of ligand:lipid in the cationic liposome for use in the methods described herein is suitably about 0.01:1 to about 0.5:10. Suitably, the weight ratio of ligand:lipid in the cationic liposome is about 0.1:10 to about 0.5:10, about 0.3:10 to about 0.4:10, or about 0.33:10, including any ratio within these ranges.

Suitable methods of administration include, but are not limited to, intravenous (IV), intratumoral (IT), intralesional (IL), aerosal, percutaneous, oral, endoscopic, topical, intramuscular (IM), sublingual (SL), intradermal (ID), intraocular (IO), intraperitoneal (IP), transdermal (TD), intranasal (IN), intracereberal (IC), intraorgan (e.g. intrahepatic), slow release implant, or subcutaneous administration, or via administration using an osmotic or mechanical pump. They can be administered as a bolus or as an infusion. In additional embodiments, the ligand can be chemically conjugated to the cationic liposome using the various methods described herein or otherwise known in the art.

Exemplary cancers that can be treated using the methods described herein include, but are not limited to, cancers of the head and neck, breast, prostate, pancreatic, brain, including glioblastoma and astrocytoma, neuroendocrine, cervical, lung, liver, kidney, liposarcoma, rhabdomyosarcoma, choriocarcinoma, angiosarcoma, melanoma, retinoblastoma, ovarian, vaginal, urogenital, gastric, colorectal cancers, multiple myeloma and cancers of the blood.

As described herein, it has been surprisingly found that the targeted cationic liposomes prepared by the disclosed methods are able to cross the blood-brain barrier. Generally, this barrier is a significant hindrance to treatments designed to treat cancers and other diseases or conditions of the brain or other treatments designed to deliver drugs to the brain. Thus, in embodiments, the methods described in herein are useful in the successful treatment of primary and metastatic brain cancers, including gliomas glioblastomas and astrocytomas, and in general to deliver drugs across the blood-brain barrier In another embodiment the methods described herein can also be used as a treatment for organophosphate poisoning.

As described herein, it has been surprisingly found that the targeted cationic liposomes prepared by the disclosed methods are able to efficiently deliver enough TMZ to target tumor cells that are resistant to standard unencapsulated TMZ to overcome their inherent resistance (which may be due to activated MGMT) resulting in these tumor cells now responding to TMZ.

As described herein, it has been surprisingly found that the targeted cationic liposomes prepared by the disclosed methods are able to induced cell death (apoptosis) in tumor cells that are resistant to the killing effects of TMZ administered without the targeted cationic liposomes.

As described herein, it has been surprisingly found that the targeted cationic liposomes prepared by the disclosed methods are able to induced apoptosis in cancer stem cells (CSC) as well as differentiated cancer cells (non-CSC) in tumors irrespective of their response to TMZ when it is administered without the targeted cationic liposomes.

As described herein, it has been surprisingly found that the level of apoptosis induced by the targeted cationic liposomes prepared by the disclosed methods is at least equal to if not proportionally greater in cancer stem cells (CSC) than in differentiated cancer cells (non-CSC) in tumors.

As described herein, it has been surprisingly found that treatment of tumors in mammals with the targeted cationic liposomes prepared by the disclosed methods not only induce tumor growth inhibition, but also result in tumor regression and that this response can be maintained even after the treatment has ended.

As described herein, it has been surprisingly found that treatment of tumor cells with the targeted cationic liposomes prepared by the disclosed methods not only induce tumor cell growth inhibition, but also result in tumor regression and that this response can be maintained even after the treatment has ended.

In suitable embodiments, the methods further comprise administering an additional different therapy to the patient in combination with the targeted temozolomide cationic liposome complex. Exemplary therapies that can be utilized include, administration of chemotherapeutic agent, small molecule, radiation therapy or a nucleic acid-based therapy. Exemplary chemotherapeutic agents include, but are not limited to, docetaxel, mitoxantrone, doxorubicin and gemcitabine. Exemplary small molecules include, but are not limited to, imatinib mesylate (GLEEVEC™), Erlotinib hydrochloride (TARCEVA™), Sunitinib Malate (SU11248, SUTENT™) and Gefitinib (IRESSA™). Exemplary nucleic acid-acid based therapies (including tumor suppressor genes, antisense oligonucleotides, siRNA, miRNA, or shRNA) include those disclosed in U.S. Published Patent Application No. 2007/0065499 and U.S. Pat. No. 7,780,882, the disclosures of each of which are incorporated by reference herein in their entireties. In suitable embodiments, the nucleic acid-based therapy comprises administration of a cationic liposome complex comprising plasmid DNA encoding the wtp53 gene and targeted via TfRscFv (scL-p53), as described in U.S. Pat. No. 7,780,882.

Also provided are methods treating a brain cancer of a patient, comprising administering to the patient a cationic liposome complex as described in U.S. Pat. No. 7,780,882. Suitably, the complex comprises a cationic liposome comprising 1,2-dioleoyl-3-trimethylammonium propane (DOTAP) and 1,2-dioleoyl-sn-glycero-3-phosphoethanolamine (DOPE), a plasmid DNA expressing wild-type p53 and an anti-transferrin receptor single chain Fv (TfRscFv) directly complexed with, but not chemically conjugated to, the cationic liposome. The methods further comprise administering Temozolomide or scL-TMZ, suitably before, at the same time or after administration of the cationic liposome complex.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Preparation of Cationic Liposomes Comprising Temozolomide

Materials:
DOTAP (1,2-dioleoyl-3-trimethylammonium propane, chloride salt)
  Obtained from Avanti Polar Lipids, Inc. Cat. #890890E, MW 698.55
  Concentration: 25 mg/mL ethanol solution
  Dilute lipid to 20 mg/ml with absolute ethanol before use
DOPE (1,2-dioleoyl-sn-glycero-3-phosphoethanolamine)
  Obtained from Avanti Polar Lipids, Inc. Cat. #850725E, MW 744.04
  Concentration: 25 mg/mL ethanol solution.
  Dilute lipid to 20 mg/ml with absolute ethanol before use
Temozolomide (TMZ, M.W. 194.15), powder
  Obtained from Sigma, Cat. #T2577-100 mg
  Dissolve TMZ in pure DMSO to desired concentration. For example, 19.415 mg/ml=100 mM of TMZ; 28 mg/ml=144.218 mM of TMZ
Ultra-pure, endotoxin free LAL Reagent Water (e.g. BioWhittaker, Cat. #W50-500, endotoxin <0.005 EU/ml)
Injector: Hamilton Gastight Syringe, 1 ml (Hamilton #81230) with a 22 gauge needle, part #81365)

Procedure:
1) Fresh TMZ solution is prepared by dissolving TMZ in DMSO to the desired concentration by vortexing at high speed for 5-10 mins (must be clear). The solution is held at room temperature until used to mix with lipids.
2) Place lipid solutions at 37° C. for 10-15 min. The lipid solutions are then placed in a 65° C. water bath with occasional shaking for 5 min.
3) To prepare the Lip-TMZ: Place a brown glass bottle with stir bar on a hot plate set to 50° C. to 60° C. While stirring at high speed without splashing, add the lipids and TMZ to the bottle in the following order. It should be noted that other component ratios and concentrations as described herein can be prepared using the same protocol as shown below.

For 0.5:1 (Lip:TMZ) molar ratio (2 mM TMZ in formulation)

DOTAP    87.5 µl (of 20 mg/ml) = 2.5 µmol or 1.75 mg
DOPE     93.75 µl (of 20 mg/ml) = 2.5 µmol or 1.875 mg
Add TMZ soln., 100 µl (of 19.41 mg/ml) = 10 µmol,
Continue stir for 3 min. after all 3 are added For 1:1 (Lip:TMZ) molar ratio (2 mM TMZ in formulation)

DOTAP    175 µl (of 20 mg/ml) = 5 µmol or 3.5 mg
DOPE     187.5 µl (of 20 mg/ml) = 5 µmol or 3.75 mg
Add TMZ soln., 100 µl (of 19.41 mg/ml) = 10 µmol,
Continuously stir for 3 min. after all 3 added For 1:1 (Lip:TMZ) molar ratio (8 mM TMZ in formulation)

DOTAP    560 µl (of 25 mg/ml) = 20 µmol or 14 mg
DOPE     600 µl (of 25 mg/ml) = 20 µmol or 15 mg
Add TMZ soln., 277.36 µl (of 28 mg/ml) = 40 µmol,
Continuously stir for 3 min. after all 3 added For 2:1 (Lip:TMZ) molar ratio (2 mM TMZ in formulation)

DOTAP    350 µl (of 20 mg/ml) = 10 µmol or 7 mg
DOPE     375 µl (of 20 mg/ml) = 10 µmol or 7.5 mg
Add TMZ soln., 100 µl (of 19.41 mg/ml) = 10 µmol,
Continuously stir for 3 min. after all 3 added 4) Warm 4 mL LAL water to 65° C. in water bath in brown glass bottle with stir bar. Immediately prior to addition of the Lipid-TMZ solution, move the bottle to a hot plate (50°-60° C.). Stir water at high speed with no splashing for a few seconds to remove bubbles from the stir bar.
5) Keep the water on the hot plate. Continue stirring the water at high speed (without splashing) during lipid addition. After mixing lipids and TMZ as above, immediately and as rapidly as possible, using the Hamilton syringe for injection, inject the mixture into the hot water on the hot plate (50°-60° C.) directly into the center of the vortex. Continue stirring on high speed (without splashing) for 1 min after the addition of the lipid mixture while loosely covered.

6) Move the glass bottle to a room temperature stir plate and continue to stir slowly until the loosely covered solution cools down to 20-25° C. (room temperature).

7) Adjust the volume to 5 ml with room temperature LAL water.

8) Filter the solution using a 0.22 μm pore Milex GV filter if desired.

9) Measure particle size and zeta potential if desired.

Results of these preparation methods demonstrate approximately at least 30-55% loading, of TMZ and liposomes having a particle size of about 20-60 nm and a Zeta Potential of about 30 to 50 mV.

Example 2

Preparation of scL-TMZ Without Chemical Conjugation (By Simple Mixing)

Using the TMZ-comprising cationic liposomes prepared according to the procedure described in Example 1, the ligand targeted TMZ cationic liposome complex as described herein is prepared by simple mixing of the components and without chemical conjugation. The preparation of the complexes was in accordance with the following general procedure:

To the liposome-water (or buffer) the appropriate amount of targeting moiety is added to give the desired ratio and mixed by gentle inversion 5-10 seconds. The targeting moiety can be a ligand including but not limited to transferrin or folate, or other proteins. It can also be an antibody or an antibody fragment that targets a cell surface receptor including, but not limited to, the transferrin or HER-2 receptor (e.g., TfRscFv). This mixture is kept at room temperature for 10-15 minutes (again inverted gently for 5-10 seconds after approximately 5 minutes). To yield the desired final volume the targeting moiety-Lip-TMZ admixture is mixed with any volume (including none) of water (suitably deionized water) or a buffer of any pH including, but not limited to, Tris buffers, HEPES buffers or Phosphate Buffered Saline, required to give a desired volume and inverted gently for 5-10 seconds to mix. This mixture is kept at room temperature for 10-15 minutes (again inverted gently for 5-10 seconds after approximately 5 minutes).

Typically, for use in an in vitro assay, it is desirable that the amount of TMZ in the final complex is in the range of about 1 μM to 300 μM per well; for in vivo use, it is desirable to provide about 1 mg/kg to about 50 mg/kg of TMZ per injection. For use in vivo dextrose or sucrose is added last to a final concentration of about 1-50% (V:V) dextrose or sucrose, suitably 5% dextrose or 10% sucrose, and mixed by gentle inversion for 5-10 seconds. This mixture is kept at room temperature for 10-15 minutes (again inverted gently for 5-10 seconds after approximately 5 minutes).

A specific example at a suitable ratio of 1:30 (antibody fragment:liposome, w:w) and 1:1 Liposome:TMZ (molar ratio) is as follows: For a final volume of approximately 700 uL, at a TMZ concentration of 25 mg/kg/injection, mix 319 μL of Lip:TMZ (8 mM stock) with 305 μL of antibody fragment (at an anti-transferrin receptor single chain antibody fragment [TfRscFv] concentration of 0.2 mg/mL). Add 6 μL of water or buffer and, as the last step, 70 μL of 50% Dextrose or no water or buffer and 140 uL of 50% sucrose.

A second specific example at a preferred ratio of 1:30 (antibody fragment:liposome, w:w) and 1:1 Liposome:TMZ (molar ratio) is as follows: For a final volume of approximately 1.8 mL, at a TMZ concentration of 25 mg/kg/injection, mix 1276 μL of Lip:TMZ (2 mM stock) with 305 μL of antibody fragment (at an anti-transferrin receptor single chain antibody fragment [TfRscFv] concentration of 0.2 mg/mL). 39 μL of water or buffer is added and 180 μL of 50% Dextrose is added as the last step.

Another specific example at a preferred ratio of 1:30 (antibody fragment:liposome, w:w) and 1:1 Liposome:TMZ (molar ratio) is as follows: For a final volume of approximately 400 μL, at a TMZ concentration of 5 mg/kg/injection, mix 280 μL of Lip:TMZ (2 mM stock) with 64 μL of antibody fragment (at an anti-transferrin receptor single chain antibody fragment [TfRscFv] concentration of 0.2 mg/mL). 16.5 μL of water or buffer is added and 40 μL of 50% Dextrose is added as the last step.

The size (number average) of the final complex prepared by the methods is between about 10 to 800 nm, suitably about 20 to 400 nm, most suitably about 25 to 200 nm with a zeta potential of between about 1 and 100 mV, more suitably 10 to 60 mV and most suitably 25 to 50 mV as determined by dynamic light scattering using a Malvern Zetasizer ZS. This size is small enough to efficiently pass through the tumor capillary bed, or cross the blood brain barrier, and reach the tumor cells.

Example 3

Determination of the Percent Encapsulation of TMZ in the scL-TMZ Complex

To determine the percent of the TMZ encapsulated in the scL-TMZ complex, we prepared scL-TMZ as described in Example 1 with 2 mM stock Lip:TMZ. Various amounts of complex were prepared ranging from 126 to 560 ul scL-TMZ. The scL-TMZ complex was subsequently diluted to a Lip:TMZ concentration of 0.5 mM. The initial concentration of TMZ was checked by measuring the absorbance of the scL-TMZ complex at 320 nm using a Beckman spectrophotometer. A standard curve of TMZ concentrations spanning 0.001 to 0.1 mM TMZ was also generated by measuring absorbance at 320 nM using DMSO as the blank. Free TMZ was separated from complexed scL-TMZ by filtration through a Vivaspin® 500, 5 kDa MWCO (GE Healthcare, UK). 200 ul of the diluted scL-TMZ complex was loaded onto the filter and centrifuged at 14,000 g for 15 min at room temperature. The flow through was collected and the volume (175 ul), and optical density at 320 nm were determined. Endotoxin free LAL water (175 ul) was added to the filter which was mixed by inversion 10 times and again centrifuged as above. The flow through was again collected, volume and OD measured as above. The bound complex on the filter was recovered by addition of 100 ul of Endotoxin free LAL water to the filter. After inversion 10 times the filter was placed upside down in the collection tube and centrifuged at 1,000 g for 2 minutes and the OD measured. The TMZ concentrations of the loaded scL-TMZ complex, each of the flow through samples and the retained sample were determined from the standard curve and the amount of TMZ in each calculated, correcting for volume of each sample and for dilution. In all cases, all of the unencapsulated TMZ was recovered in the initial flow through with nothing detected in the wash sample. Multiple experiments were performed and the average percent encapsulation was found to be 38.7±3.7% (mean±S.E.)

The identical procedure was employed to test the encapsulation when 8 mM stock Lip:TMZ was prepared. In this instance the volume of scL-TMZ prepared as described in Example 1 was 350 ul. Multiple experiments were performed. The percent encapsulation of TMZ, 39.2±3.7% (mean±S.E.), was virtually identical to that obtained with 2 mM Lip:TMZ. Moreover, the size of the scL-TMZ was determined using the Malvern Zetasizer ZS after recovery from the Vivaspin® filter and compared to the initial size obtained immediately post-preparation prior to loading on the column. There was no change evident, with the initial and final sizes of the scL-TMZ complex being 75.99 nm and 76.93 nm, respectively.

Example 4

In Vitro Efficacy of Targeted Cationic Liposomes Comprising Temozolomide

Human glioblastoma multiforme (GBM) cell lines U87MG and T98G were obtained from ATCC (Manassas, Va.). U87 is derived from a grade IV glioblastoma, and carries wtp53 (Van Meir E G, Kikuchi T, Tada M, Li H, Diserens A C, Wojcik B E, Huang H J S, Friedmann T, Detribolet N and Cavenee W K (1994) Analysis of the P53 Gene and Its Expression in Human Glioblastoma Cells. Cancer Research 54: pp 649-652). A version of U87MG that stably expresses the luciferase gene has been obtained from Caliper Life Sciences for use in in vivo studies where tumor growth and response will be monitored by the IVIS® Imaging System, Xenogen. The human GBM cell line U251 was obtained from the Division of Cancer Treatment and Diagnosis Tumor Repository, National Cancer Institute-Frederick (Frederick, Md.). Cells were maintained at 37° C. in a 5% $CO_2$ atmosphere in modified IMEM (Gibco, Grand Island, N.Y.; U87 and U87MG-luc2 cells), MEM (Mediatech Manassas, Va.; T98G cells), or RPMI 1640 medium (Gibco; U251 cells) supplemented with 10% heat-inactivated fetal bovine serum (Omega Scientific, Tarzana, Calif.), 2 mmol/L L-glutamine (Mediatech, Manassas, Va.), and 50 μg/mL each of penicillin, streptomycin, and neomycin (PSN). Cells were grown to 70-80% confluence before the next passage or further experiments through trypsinization using TrypLE Express (Gibco). Sodium 3'-[1-(phenylaminocarbonyl)-3,4-tetrazolium]-bis(4-methoxy-6-nitro)benzene sulfonate (XTT) was purchased from Polysciences (Warrington, Pa.).

The human multiple myeloma cell line KMS-11 was maintained at 37° C. in a 5% $CO_2$ atmosphere in RPMI 1640 medium supplemented with 10% heat-inactivated fetal bovine serum 2 mmol/L L-glutamine and 50 ng/mL each of penicillin, streptomycin, and neomycin (PSN). Cells were grown to 70-80% confluence before the next passage or further experiments. These cells grow in suspension and not as monolayers.

U87MG is categorized as being sensitive to TMZ (Patil R, Portilla-Arias J, Ding H, Inoue S, Konda B, Hu J W, Wawrowsky K A, Shin P K, Black K L, Holler E and Ljubimova J Y (2010) Temozolomide Delivery to Tumor Cells by a Multifunctional Nano Vehicle Based on Poly (Beta-L-Malic Acid). Pharmaceutical Research 27: pp 2317-2329). This is a well established orthotopic mouse model of GBM (Liu Y, Lang F, Xie X, Prabhu S, Xu J, Sampath D, Aldape K, Fuller G and Puduvalli V K (2011) Efficacy of Adenovirally Expressed Soluble TRAIL in Human Glioma Organotypic Slice Culture and Glioma Xenografts. Cell Death & Disease 2). U87MG cells reproducibly develop tumors within 10 days when $5\times10^5$ cells are intracranially injected in athymic nude mice. The mice succumb to tumor burden within 30-40 days. T98G is also isolated from a human glioblastoma. However, this cell line is known to be resistant to TMZ (Patil R, Portilla-Arias J, Ding H, Inoue S, Konda B, Hu J W, Wawrowsky K A, Shin P K, Black K L, Holler E and Ljubimova J Y (2010) Temozolomide Delivery to Tumor Cells by a Multifunctional Nano Vehicle Based on Poly(Beta-L-Malic Acid). Pharmaceutical Research 27: pp 2317-2329) and carries a mutant form of the p53 gene (Van Meir E G, Kikuchi T, Tada M, Li H, Diserens A C, Wojcik B E, Huang H J S, Friedmann T, Detribolet N and Cavenee W K (1994) Analysis of the P53 Gene and Its Expression in Human Glioblastoma Cells. Cancer Research 54: pp 649-652). T98G xenograft tumors are induced via subcutaneous inoculation of $5\text{-}10\times10^6$ cells in Matrigel™ (Torres S, Lorente M, Rodriguez-Fomes F, Hernandez-Tiedra S, Salazar M, Garcia-Taboada E, Barcia J, Guzman M and Velasco G (2011) A Combined Preclinical Therapy of Cannabinoids and Temozolomide Against Glioma. Molecular Cancer Therapeutics 10: pp 90-103). Both cell lines have elevated TfR expression (Sang H, Kelley P Y, Hatton J D and Shew J Y (1989) Proto-Oncogene Abnormalities and Their Relationship to Tumorigenicity in Some Human Glioblastomas. Journal of Neurosurgery 71: pp 83-90).

Studies were carried out to compare the efficacy of standard free (unencapsulated) TMZ; and unliganded TMZ-containing liposomes (Lip-TMZ) The Lip-TMZ was prepared as described above in Example 1 using a liposome concentration of 2 mM. The zeta potentials of the Lip-TMZ molecules ranged from 35.6-40.1 mV. The TMZ concentration used was varied from 1 to about 250 uM. The ratios of Liposome to TMZ was 0.5:1, 1:1 or 2:1 (molar ratio).

Human brain tumor derived U251 cells were plated in triplicate at $2\times10^3$ per well in a 96-well plate. Following overnight incubation, the medium was replaced with serum-free medium, overlaid with 100 μL of indicated concentrations of either Lip-TMZ, or free TMZ, incubated for 5 h, and then supplemented with fetal bovine serum. After incubation for an additional 91 h, cell viability was determined by the XTT assay as described previously (Rait A, Pirollo K F, Rait V, et al. Inhibitory effects of the combination of HER-2 antisense oligonucleotide and chemotherapeutic agents used for the treatment of human breast cancer. Cancer Gene Ther 2001; 8:728-39.). Formazan absorbance, which correlates to cell viability, was measured at 450 nm using a microplate reader (Bio-Rad, Hercules, Calif.). The $IC_{50}$ value, the drug concentration resulting in 50% cell kill, was interpolated from the graph of the log of drug concentration versus the fraction of surviving cells.

FIG. 1 demonstrates that in human brain tumor (GBM) cell line U251, compared with the effects of free TMZ, in vitro treatment with the liposome encapsulated TMZ as described herein resulted in a significant reduction in $IC_{50}$ values in human GBM cells. 50% of the cells were killed at TMZ concentrations of only 46.3 μM, 28.8 μM and 16 μM, when these concentrations of TMZ were encapsulated in the targeted cationic-liposome-TMZ complex at Lip/TMZ molar ratios of 0.5:1, 1:1 and 2:1, respectively. In contrast these concentrations of TMZ had virtually no cell killing effect when not part of the scL-TMZ complex. The higher the ratio of Lip to TMZ, the greater the increase in cell killing effect, yielding a lower $IC_{50}$ value. It is well known by those familiar with the art that free, unencapsulated TMZ is the form of the drug most commonly used to treat tumors in patients.

Figure 2:
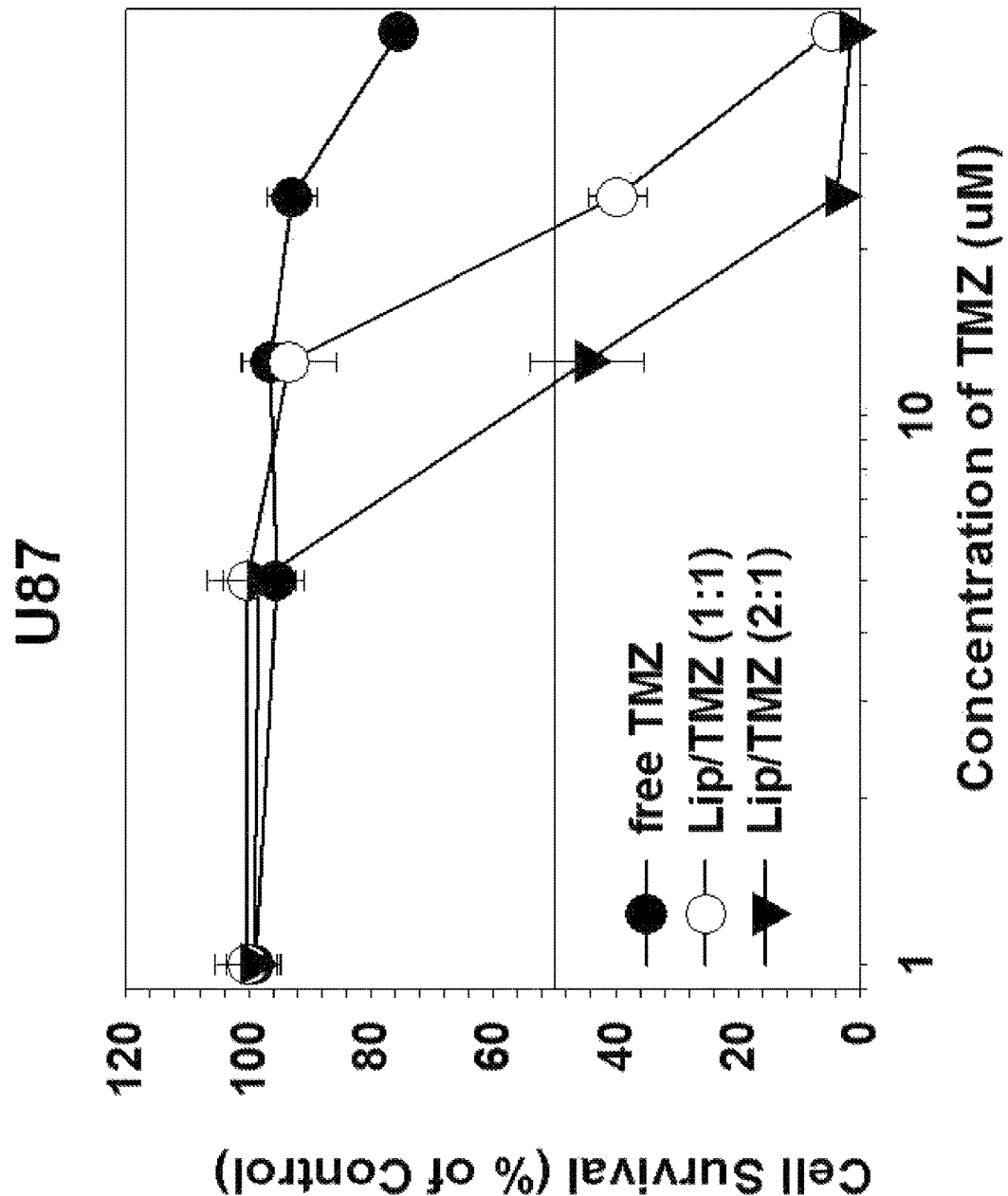
FIG. 2 shows U87 cell survival versus concentration of TMZ for free TMZ and cationic liposomes comprising TMZ, as described herein.

Similar results are shown in FIG. 2 with human GBM tumor cell line U87 comparing free TMZ and the Lip-TMZ at molar ratios of Liposome to TMZ of 1:1 and 2:1. Once again the unencapsulated TMZ has virtually no cell killing effect on these brain tumor cells. In contrast when encapsulated in the Liposome at molar ratios of 1:1 or 2:1 (Lip:TMZ) using the method of this invention, TMZ concentrations of only 11.4 and 21.5 µM, respectively resulted in significant tumor cell death.

Example 5

Increased Effect of scL-TMZ On Tumor Cells Compared to Free (Unencapsulated) TMZ The scL-TMZ complex was prepared as described above in Examples 1-2 using an anti-transferrin receptor single-chain antibody fragment (TfRscFv) as the targeting moiety, a Lip:TMZ molar ratio of 1:1 (size=46.2 nm; zeta potential=42.5 mV) (liposome concentration=2 mM) and an TfRscFv to Liposome ratio if 1:30 (w:w). The size of the scL-TMZ complex was about 27.5 nm. The in vitro cell killing ability of the scL-TMZ was compared to free, unencapsulated TMZ in TMZ resistant human brain tumor cell line T98G using the XTT assay.

Figure 3A:
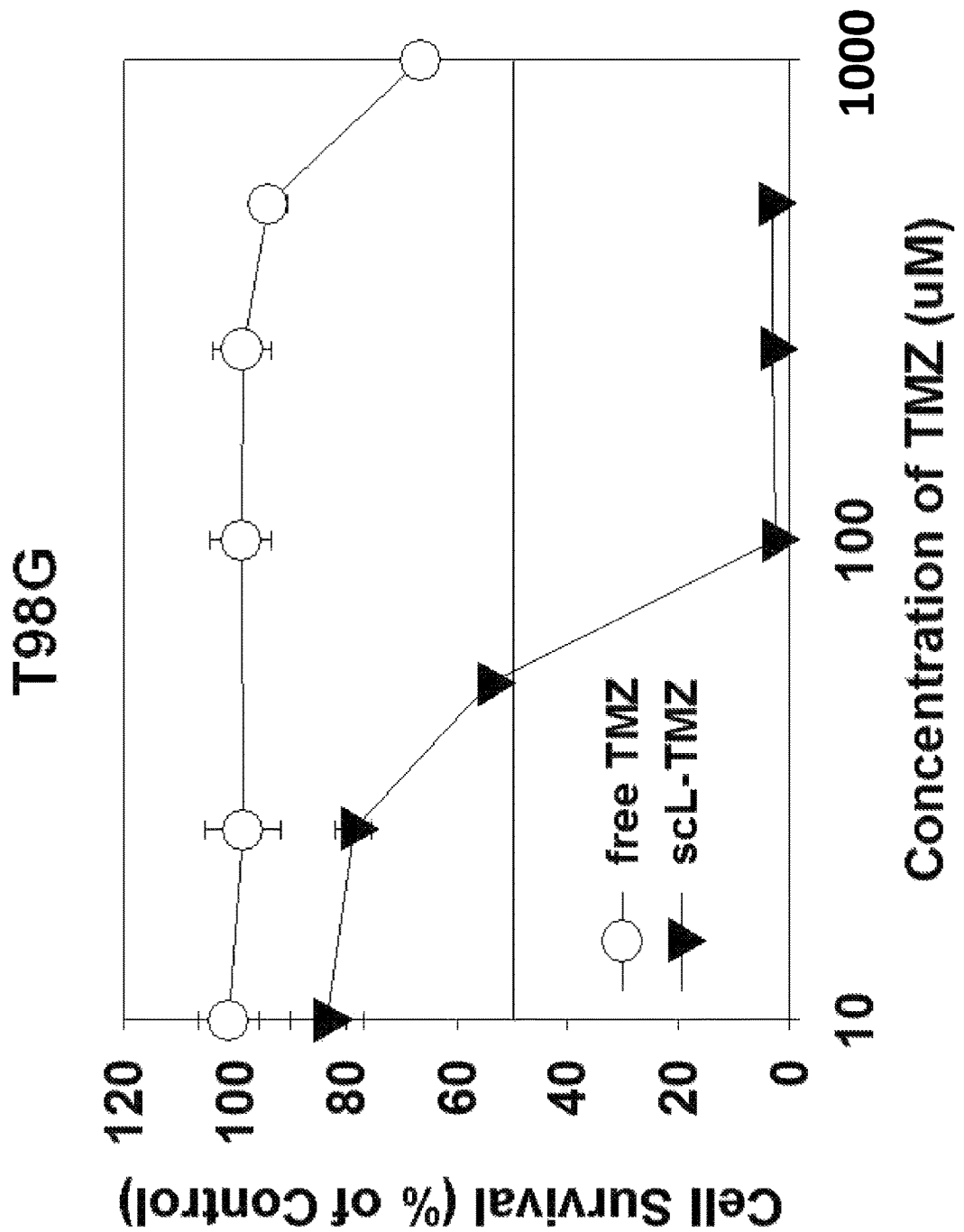
FIG. 3A shows T98G cell survival versus concentration of TMZ for free TMZ and a targeted cationic liposome comprising TMZ, as described herein.

FIG. 3A shows that tumor targeting scL-TMZ complex, has significantly improved anti-cancer efficacy compared to free TMZ. The free TMZ has an $IC_{50}$ value >1000 µM. In contrast, when prepared according to the methods described herein and delivered to the tumor cell by means of the tumor-targeting complex, at least 20 fold less TMZ effectively kills the cancer cells. This is especially significant as this GBM cell line is well known in the art to be resistant to the killing effects of TMZ. This reversal of resistance is due to the efficient delivery and uptake of the TMZ payload into the tumor cell by means of the binding of the targeting ligand (protein, antibody or antibody fragment) to its receptor on the cell and the triggering of uptake through active transport mechanisms like receptor mediated endocytosis. This process "floods" the cells with drug overcoming the mechanisms the tumor cell has in place to repair the DNA damage caused by TMZ (such as upregulation of MGMT), and/or the mechanisms to pump the TMZ out of the cells. Thus the cell dies.

There are a number of ramifications as a result of the tumor-targeting delivery of TMZ via the targeted cationic liposomes described herein.
1) Increased efficacy means less drug needs to be delivered to the patient to see improved anti-tumor effect.
2) Tumor-specific delivery (tumor specificity) will decrease the deleterious side-effects currently associated with TMZ as the drug will not be taken up by non-target cells.
3) The efficient delivery of TMZ to the tumor cells overcomes the resistance to TMZ inherent in a significant population of brain tumors (GBM and astrocytomas) and other cancer types including, but not limited to, prostate cancer, multiple myeloma, lung cancer, liver cancer, ovarian cancer, pancreatic cancer, head and neck cancer, kidney cancer, stomach cancer, and melanoma. This reversal of resistance broadens the scope of use for TMZ as an anti-cancer treatment.

Figure 3B:
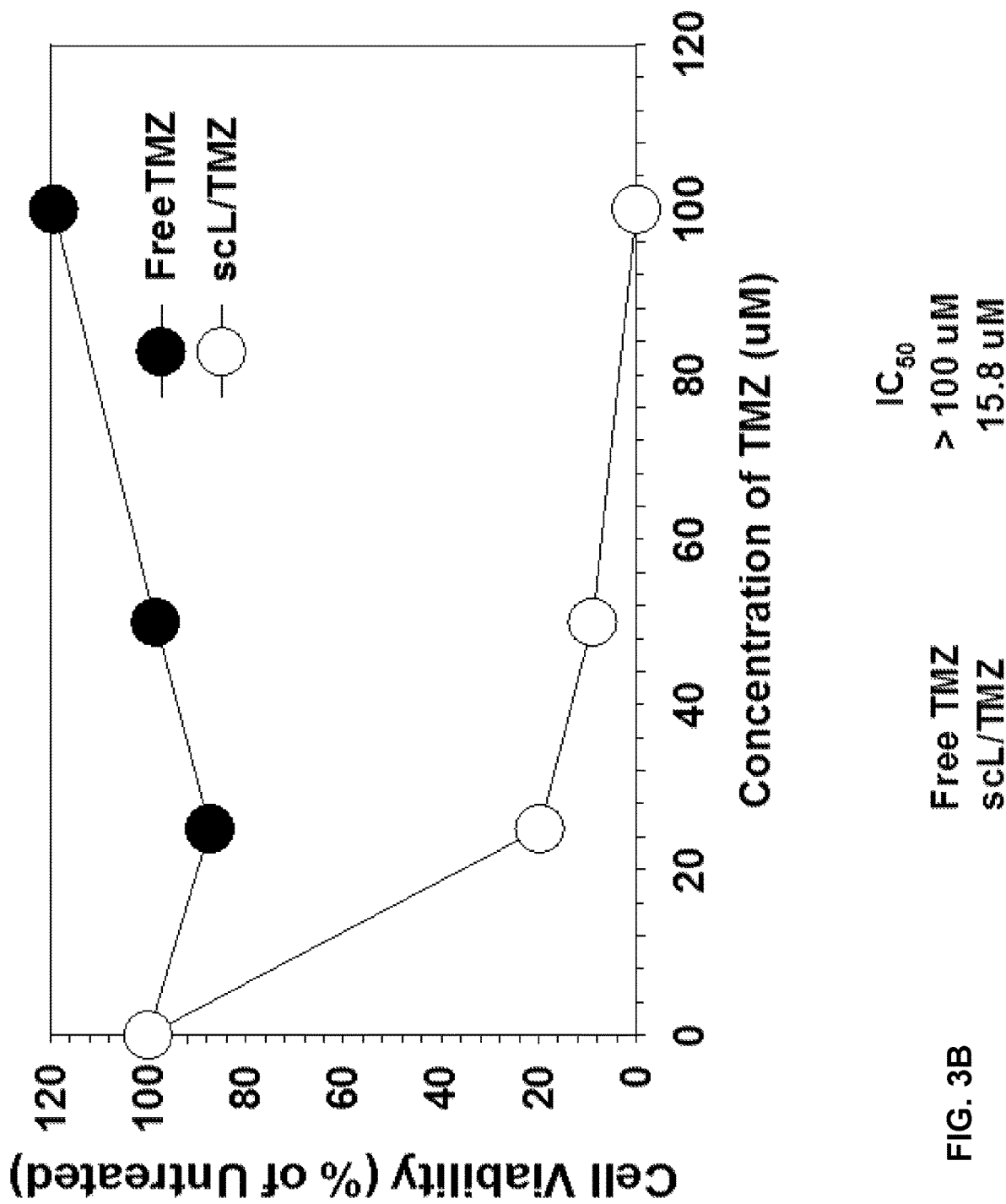
FIG. 3B shows KMS-11 cell survival versus concentration of TMZ for free TMZ and a targeted cationic liposome comprising TMZ, as described herein.

FIG. 3B demonstrates that the method of this invention is not limited to sensitization of brain tumor cells to TMZ. The killing effects of scL-TMZ were compared to that of free (unencapsulated TMZ) in multiple myeloma cell line KMS-11. The scL-TMZ complex was prepared with different increasing doses of TMZ (0 to 100 uM TMZ) as described above using an anti-transferrin receptor single-chain antibody fragment (TfRscFv) as the targeting moiety, a Lip:TMZ molar ratio of 1:1 (liposome concentration=8 mM) and an TfRscFv to Liposome ratio if 1:30 (w:w). The size of the scL-TMZ complex was about 143 nm. The in vitro cell killing ability of the scL-TMZ was compared to free, unencapsulated TMZ in multiple myeloma cell line KMS-11. Transfection was performed and the viability of the KMS-11 cells 48 hours post-transfection was assessed. TMZ has not previously been used to treat multiple myeloma, thus, it was very surprising that delivery of TMZ to these cells by encapsulation in the scL complex resulted in significant cell death, even at a very low concentration (25 uM) of TMZ.

The identical methodology and procedures described above were used to prepare Lip-TMZ and scL-TMZ and the resultant scL-TMZ nanocomplex was also used to transfect prostate (DU145), lung (A549), ovarian (Hey-A8), pancreatic (PANC-1) and hepatocellular carcinoma (HEP-G2) cells. In all cases there was a significant increase in tumor cell response to the TMZ when it was encapsulated in the scL nanocomplex when compared to free (unencapsulated) TMZ, the current standard method of delivery.

Example 6

TfRscFV Liposomes Crossing the Blood Brain Barrier

Figure 4A:
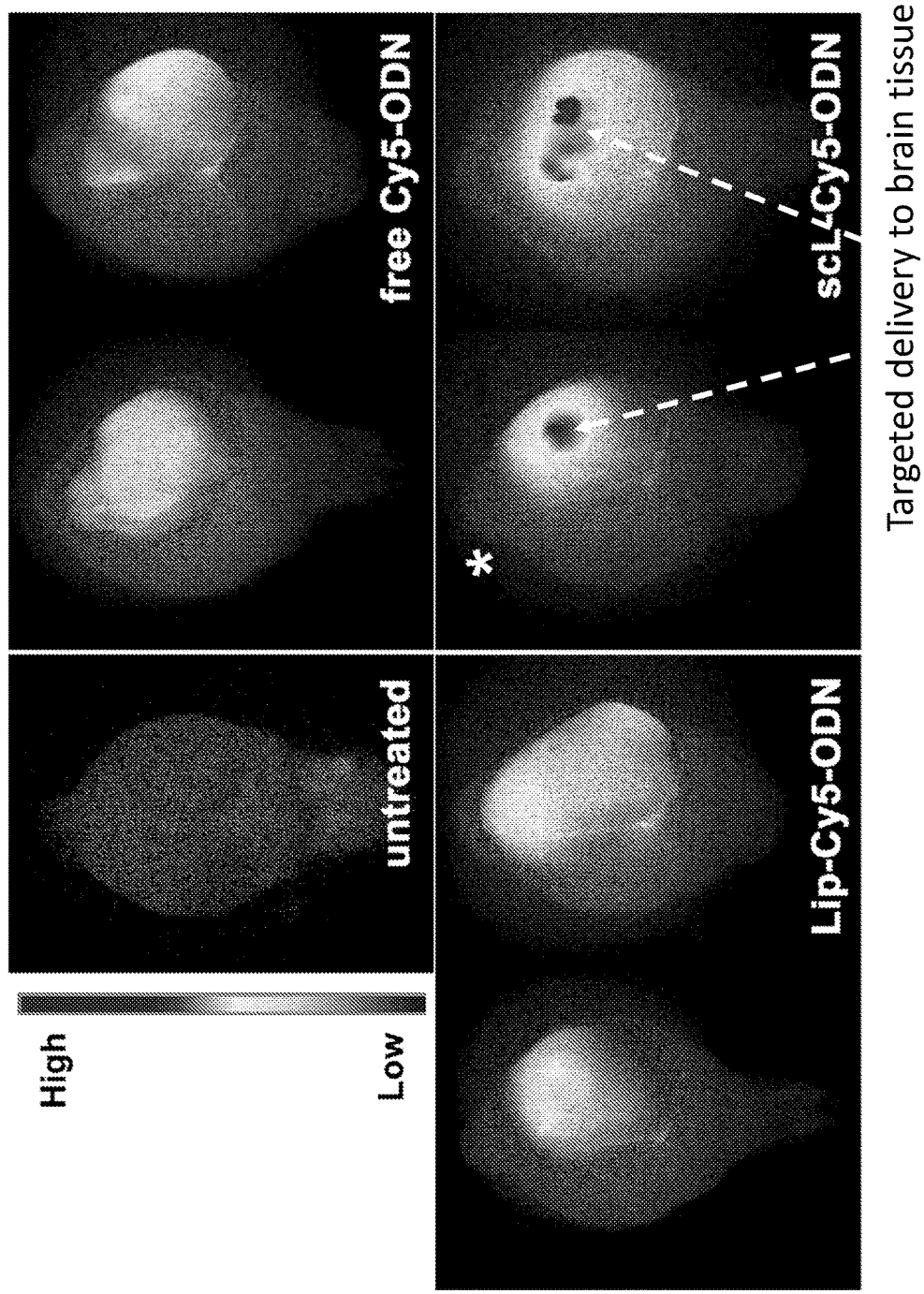
FIG. 4A shows fluorescence intensity of the brain tumors after systemic delivery of a targeted cationic liposome-fluorescently labeled oligonucleotide using the Maestro™ in vivo fluorescence imaging system.

Studies were performed to determine if the TfRscFv targeted liposome (scL) complex (scL) can cross the blood-brain barrier (BBB) and target tumors after i.v injection. Brain tumors were induced in nude mice by intracranial inoculation of $5 \times 10^5$ U87 cells. Three weeks later, the mice were I.V. injected with uncomplexed free Cy5-ODN, scL-Cy5-ODN, or unliganded Lip-Cy5-ODN (without the targeting moiety; unL-Cy5-ODN) (25 µg/mouse) (2 mice/group). Twenty-four hours post-injection, mice were euthanized and tumor-bearing brains imaged using the Maestro™ in vivo fluorescence imaging system. Fluorescence intensity of the brain tumors were compared using the Maestro™ software. I.V. injection of scL-Cy5-ODN resulted in a strong fluorescence signal specifically in the brain tumor (FIG. 4A). In contrast, only low levels of fluorescence were observed in the tumors after injection of either free Cy5-ODN or unL-Cy5-ODN. This result demonstrates the ability of scL to cross the BBB and efficiently deliver a payload to brain tumors.

Example 7

Efficacy of scL-TMZ in Animal Models of Brain Cancer Compared to Free, Unencapsulated TMZ Intra cranial GBM tumors were induced in 5-6 week old female athymic nude mice by stereotaxic inoculation of U87MG-luc2 cells that stably carry the luciferase gene. Seven to ten days post-inoculation, tumors were evaluated by bioluminescence using Xenogen IVIS in vivo imaging system (Caliper Life Sciences) and mice were evenly divided into treatment groups. Treatment was initiated on the day of randomization (day 0). Animals were injected intravenously (i.v.) via the tail vein with 5 mg/kg (per injection per mouse) of TMZ alone or TfRscFv-targeted TMZ cationic liposome complex (scL-TMZ). The scL-TMZ complex was prepared as described above in Examples 1-2 using an anti-transferrin receptor single-chain antibody fragment (TfRscFv) as the targeting moiety, a Lip:TMZ molar ratio of 1:1 (liposome concentration=2 mM) and an TfRscFv to Liposome ratio of 1:30 (w:w). Mice were injected twice per week with each reagent for 5 weeks. Control animals (Vehicle) received Liposome only (no TMZ, no TfRscFv). The sizes of the scL-TMZ complexes iv injected into the mice during this study were found to average about 100.5+14.7 nm (number average) (Mean+S.E.).

Assessment of in vivo efficacy: The in vivo response to treatment was evaluated based upon the changes in tumor growth, body weight change, and overall survival. Tumor growth was monitored by bioluminescence imaging (BLI) using Xenogen IVIS in vivo imaging system before, during, and after the treatments at the indicated date. U87MG-luc2 cells were genetically engineered to express luciferase gene which results in the emission of bioluminescence signal when treated with the substrate luciferin. The bioluminescence intensity of the brain tumors, a measure of tumor size/growth, was measured and compared between treatment groups. Half-way through treatment (after mice received 3 weeks of treatment with each reagent), all animals were scanned with magnetic resonance imaging (MRI) to evaluate the brain tumor. The animal imaging was done with a 7T with a Bruker Biopsin (Billerica, Mass.), using a respiratory gated (BioPac Physiological Data Monitor) T1-Weighted, 2 dimensional Turbo Multi-slice Multi-echo imaging sequences. Tumor volume was calculated from the MRI scan and compared between treatment groups. Body weight change was monitored weekly. Overall survival was recorded and plotted by Kaplan-Meier method.

Figure 4B:
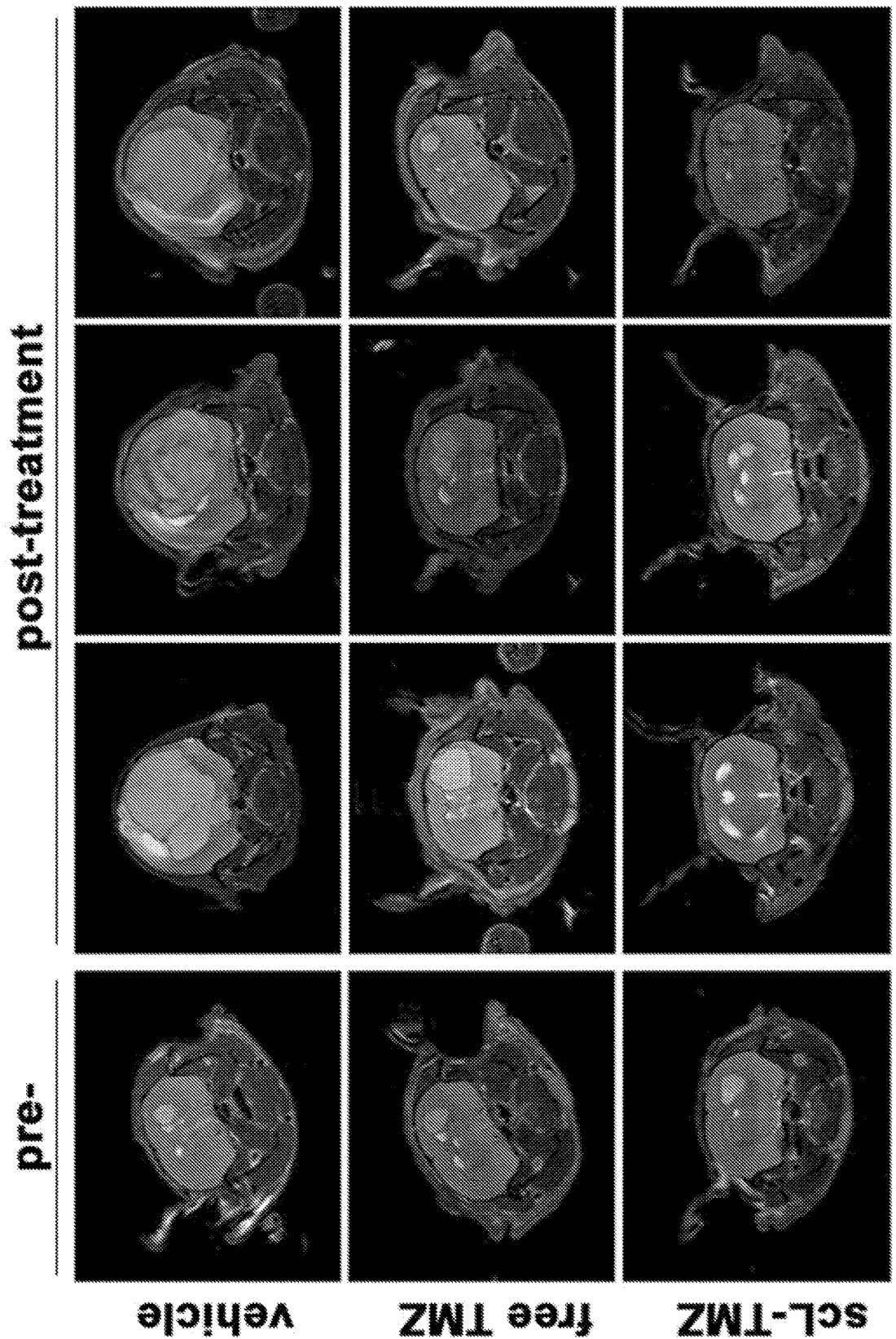
FIG. 4B shows magnetic resonance imaging (MRI) images of U87MG-luc2 glioblastoma tumor xenografts in response to treatment with free TMZ and a TfRscFv targeted cationic liposome-TMZ complex (scL-TMZ).

FIG. 4B shows the comparison of in vivo anti-tumor efficacy of the scL-TMZ and free, unencapsulated TMZ on intracranial U87MG-luc2 glioblastoma tumor xenografts. The brain tumors were imaged using MRI before treatment began and again after the mice had received 3 weeks of treatment (6 injections). The outlined areas indicate the glioblastoma tumors. Over this 3 week period the tumors in the control mice grew significantly larger as expected. As this cell line is known to be responsive to TMZ, some tumor growth inhibition was expected and was evident in the mice that received free TMZ. However, in the animals that received the scL-TMZ, not only was tumor growth inhibition evident, but tumor regression had also occurred, even over this short period of treatment, indicating the increased effectiveness of the scL-TMZ as a therapeutic agent. This was an unexpected result.

Figure 5:
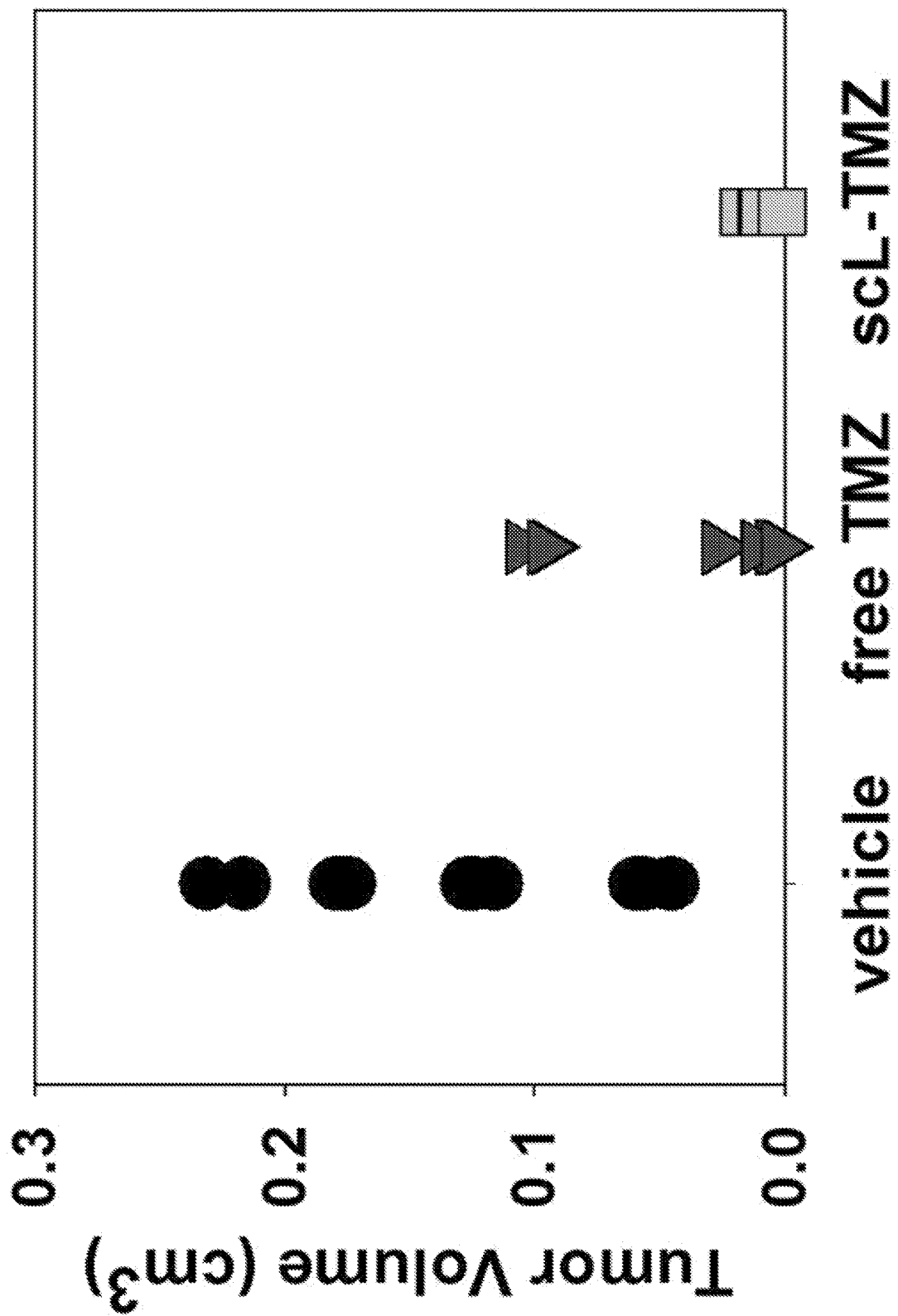
FIG. 5 shows the size of brain tumors measured by MRI after treatment with free TMZ or scL-TMZ.

A comparison of the tumor sizes in the animals of all three groups is shown graphically in FIG. 5 and show the consistent dramatic response and small tumor size of the mice treated with the scL-TMZ.

Figure 6:
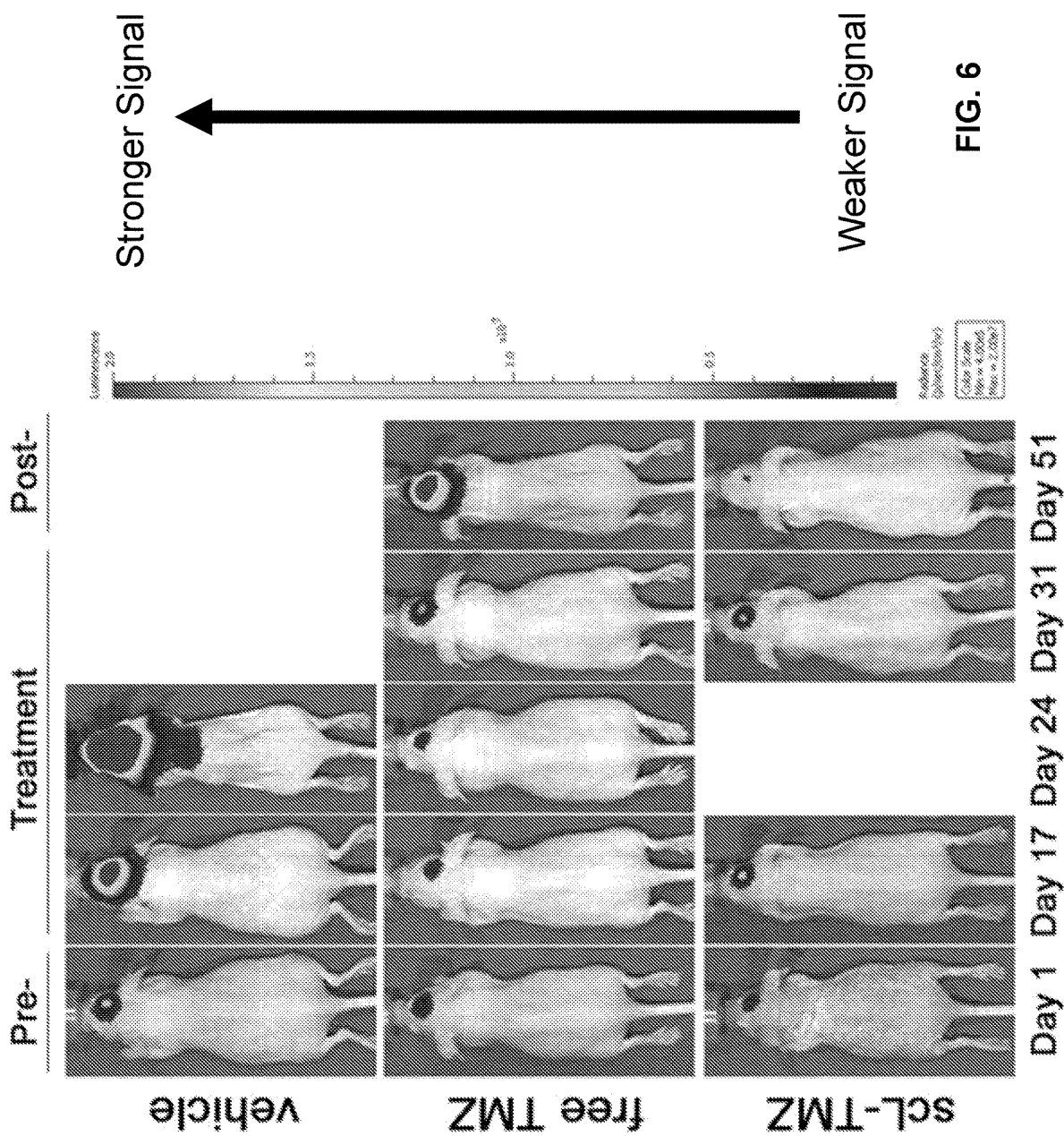
FIG. 6 shows bioluminescence imaging of tumors in mice treated with free TMZ and scL-TMZ.
Figure 7:
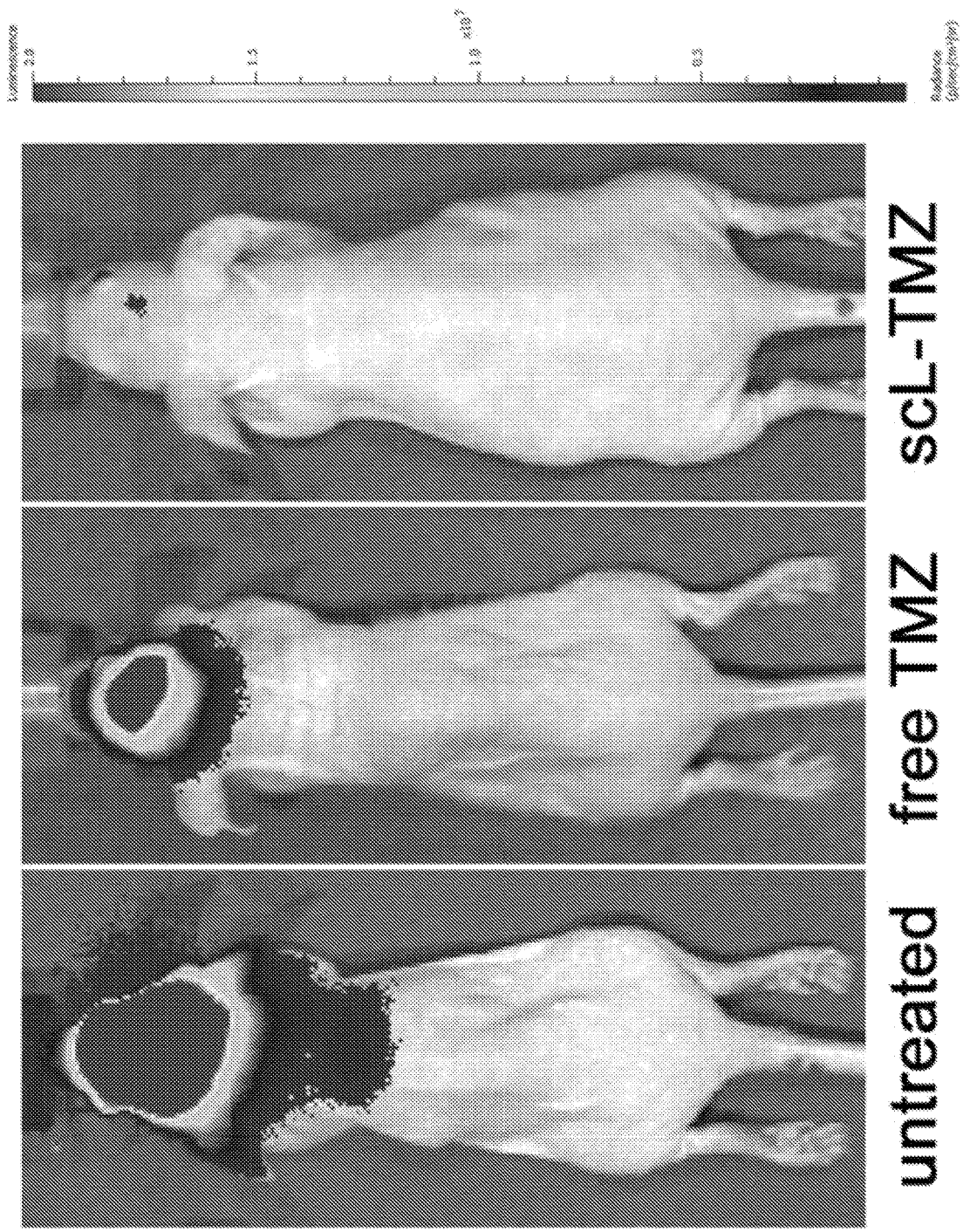
FIG. 7 shows additional bioluminescence imaging of tumors in mice treated with free TMZ and scL-TMZ.
Figure 8:
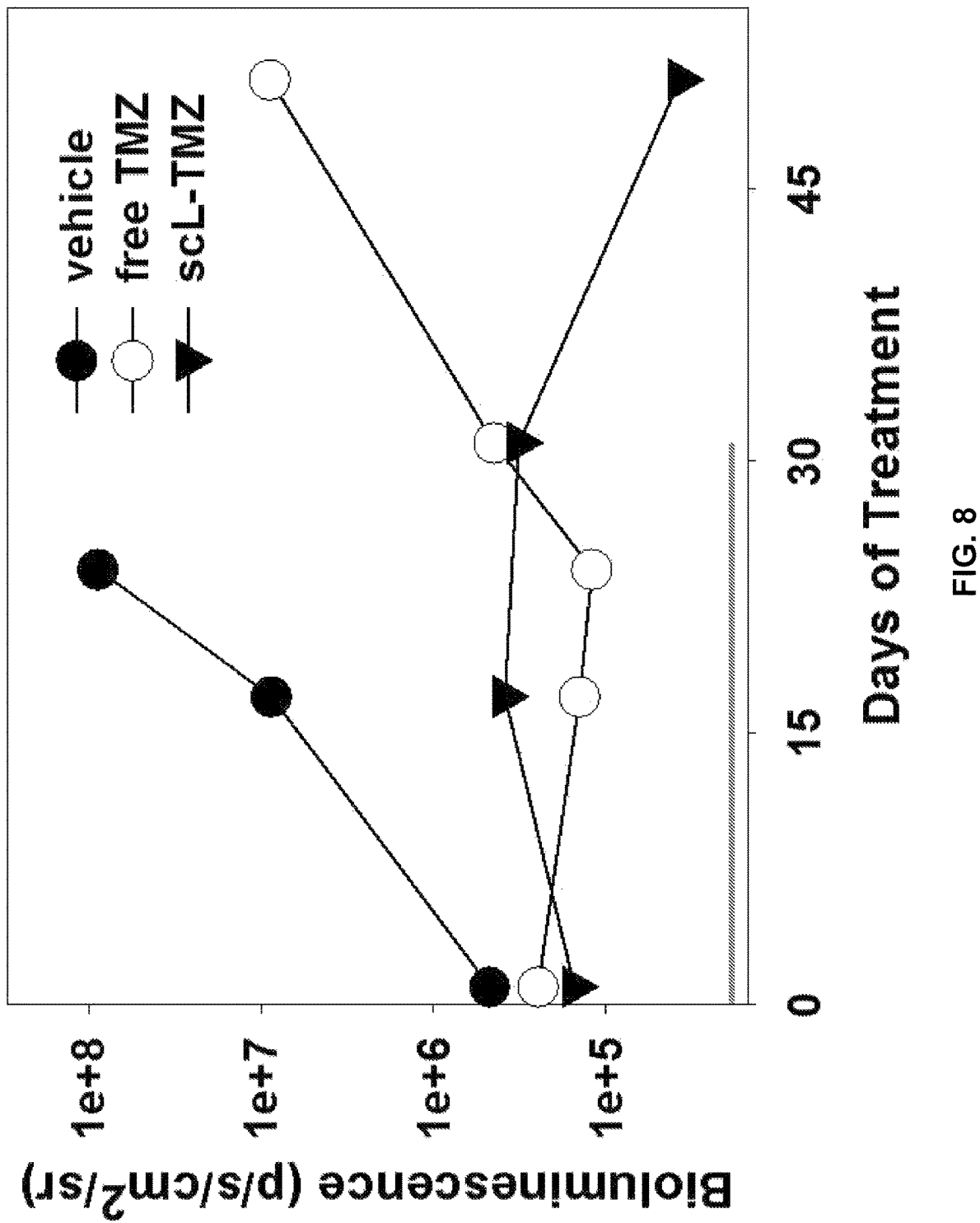
FIG. 8 shows the quantification of bioluminescence signal intensities of tumors in mice treated with free TMZ and scL-TMZ.
Figure 9:
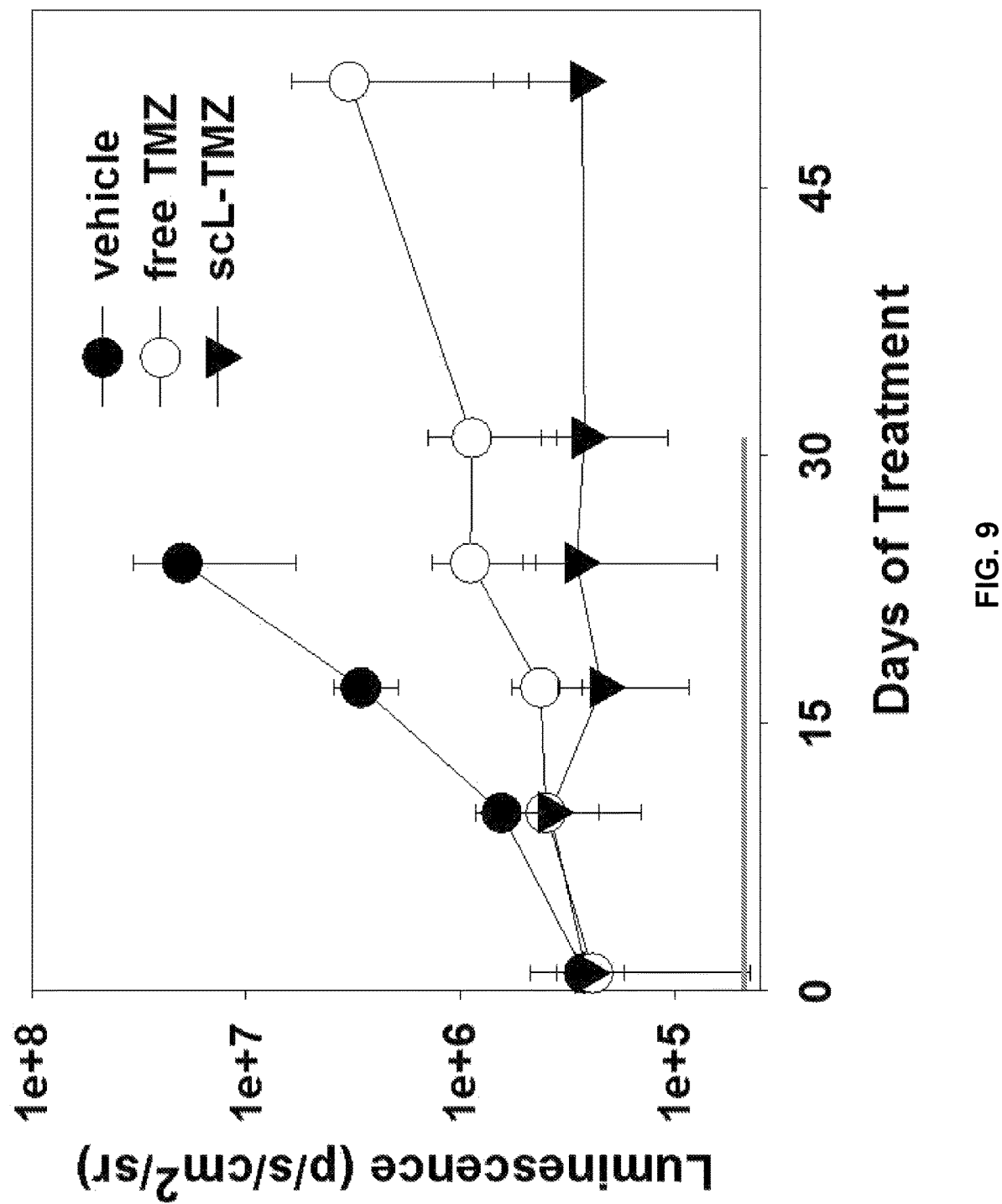
FIG. 9 shows the quantification of bioluminescence signal intensities of tumors in mice treated with free TMZ and scL-TMZ.

FIG. 6 shows the Bioluminescence (BLI) imaging via Xenogen of a representative animal from each group followed from pre-treatment through the treatment period and post-treatment. The intensity of the Bioluminescence signal, which correlates to tumor size, is shown in a color map: Red color=a stronger signal, Violet color=a weaker signal. Free TMZ, the current method of administration for brain tumors, was able to control the growth of the tumor for ~2.5 weeks. However, once treatment ended after 5 weeks, significant tumor growth occurred. In fact, recurrence was even evident at day 31 of treatment. In contrast, in the animal that was treated with scL-TMZ, not only was the tumor growth inhibition maintained throughout treatment and post treatment, but an unexpected result of tumor regression (see Day 51) was observed that lasted at least 2 weeks after the end of treatment. FIG. 7 shows an additional comparison of the results. A graphic representation of the BLI signal intensities from the mice in FIG. 6 is shown in FIG. 8 (bar at bottom of graph indicates the duration of treatment). A similar plot of the signal intensities over time for all of the mice in each group is given in FIG. 9. Here again the unexpected result of lack of tumor recurrence after the end of treatment in the scL-TMZ treated group is evident. This is unexpected since tumor recurrence is a common problem in cancers of all types including brain cancers.

Figure 10:
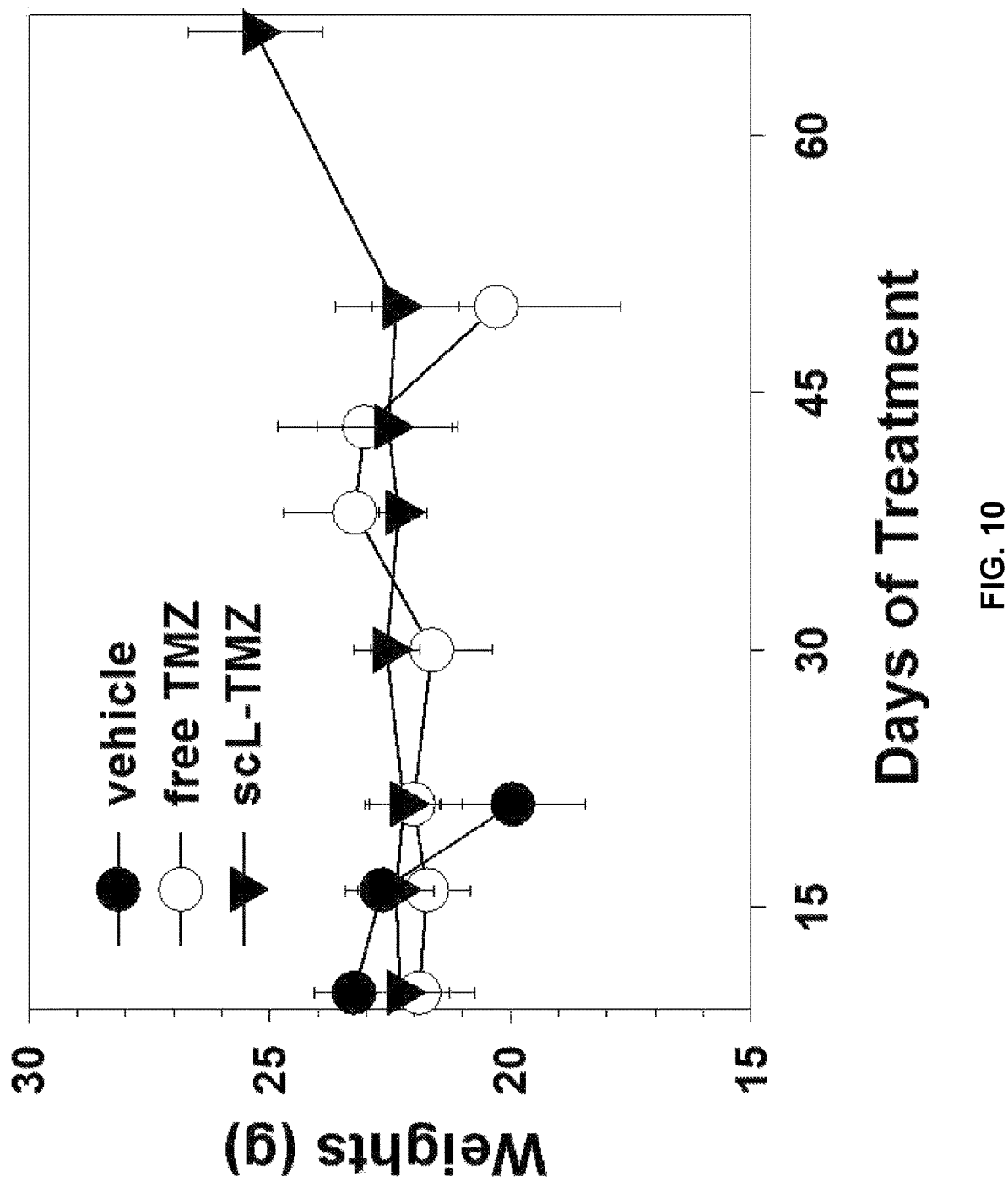
FIG. 10 shows body weight measurements of mice during and after treatment with free TMZ and scL-TMZ.

The lack of toxicity of the scL-TMZ treatment is shown by body weight measurements during treatment and post-treatment (FIG. 10). The steep decrease in weight of the animals in the Vehicle (Day 21) and Free TMZ (Day 51) groups is caused by the advanced disease state. Compared to these other groups, the animals treated with scL-TMZ evidenced no decrease in weight over the course of the experiment and even gained weight at the end. This demonstrates the lack of toxicity of this approach.

Figure 11:
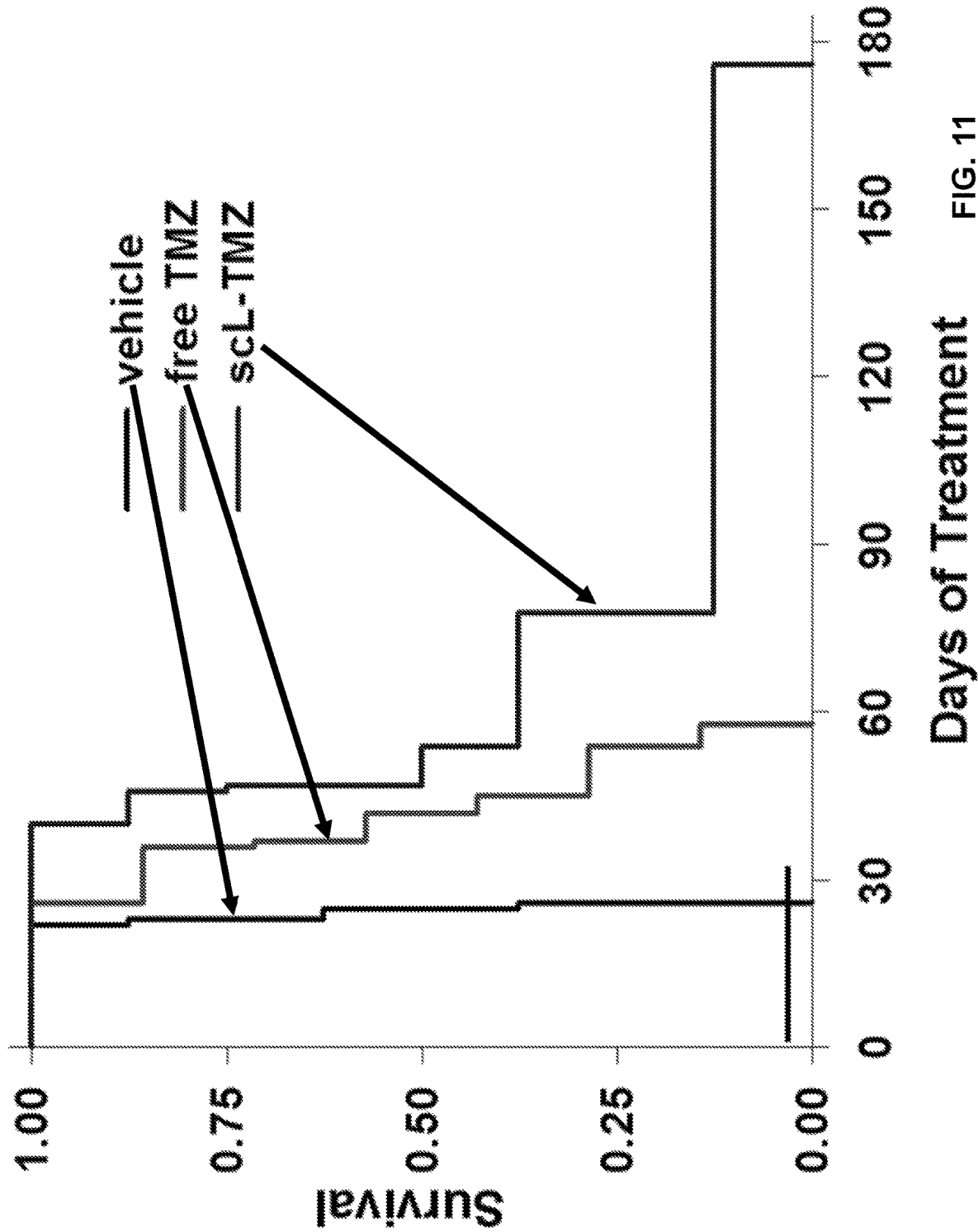
FIG. 11 shows a Kaplan-Meier plot demonstrating long term survival for animals treated with free TMZ and scL-TMZ.

The long term survival of the animals in this experiment is shown in a Kaplan-Meier plot (FIG. 11). All of the mice in the Vehicle group had died by day 30. Although the free TMZ extended the lifespan of these mice compared to the control group, there was a significant increase in long term survival after treatment with scL-TMZ compared the Free TMZ group.

Figure 12:
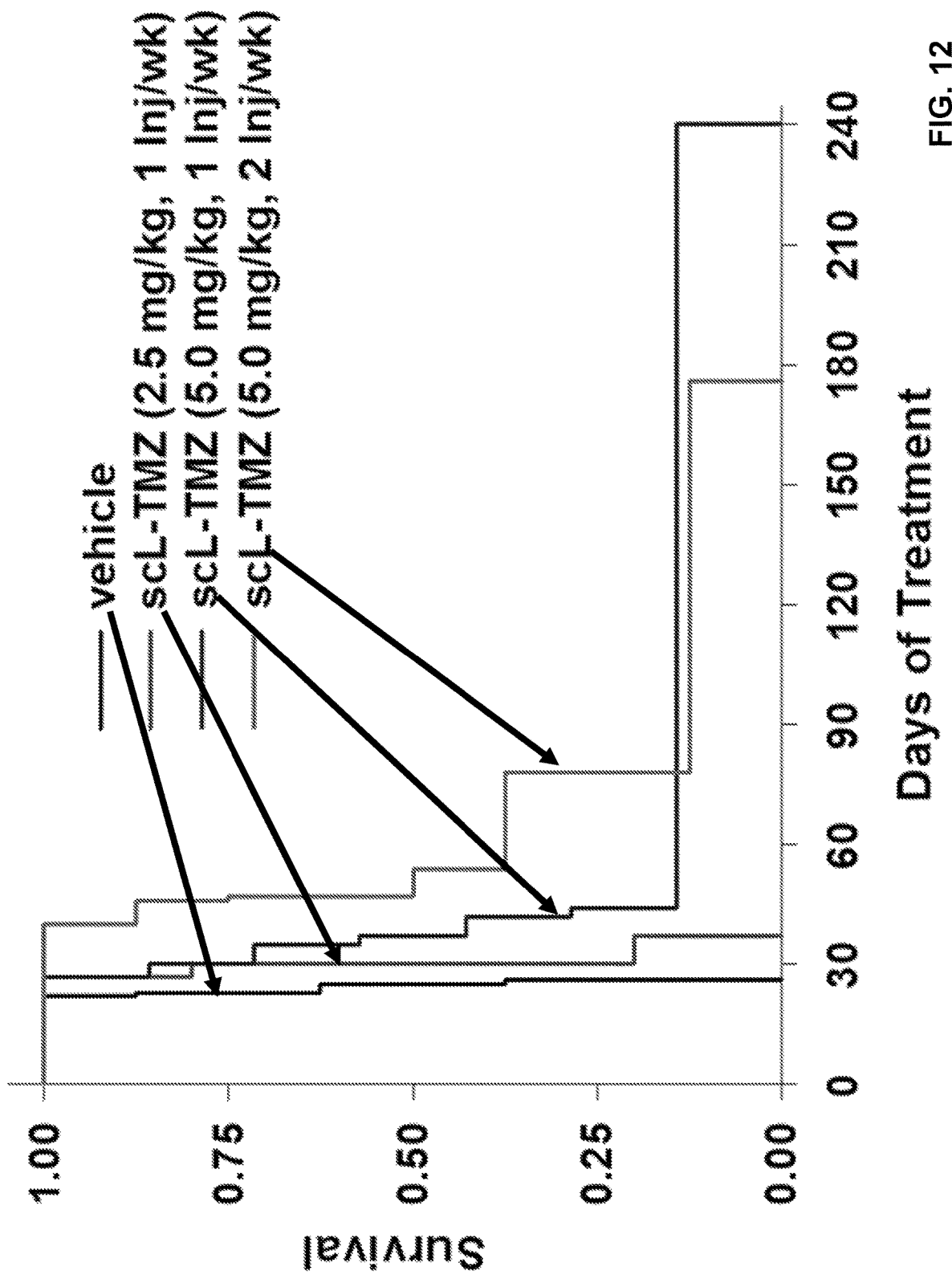
FIG. 12 shows a Kaplan-Meier plot demonstrating long term survival for animals treated with free TMZ and scL-TMZ at different doses.

In a second experiment, different doses/number of injections per week of scL-TMZ, prepared as described herein, were compared. Groups of mice bearing U87MG-luc2 glioblastoma intracranial xenograft tumors were iv tail vein injected for 5 weeks with scL-TMZ at: 2.5 mg/kg one injection per week; 5 mg/kg one injection per week; or 5 mg/kg two injections per week and survival determined. The Kaplan-Meier plot in FIG. 12 shows a dose dependent response and that even a single injection at a dose of 5 mg/kg can extend the life span of mice bearing intracranial brain tumors. Furthermore injections at a lower dose of TMZ can also be effective if the number of injections/week is increased.

Results Summary: Compared to the treatment with free TMZ, intravenous treatment with scL-encapsulated TMZ resulted in a robust inhibition against tumor growth monitored by either MRI or BLI, and prolonged the survival in an intracranial U87MG-luc2 GBM tumor xenograft model. However, no significantly increased toxicity assessed by body weight change was observed in scL-TMZ treated animals compared to those of free TMZ treated animals. Also, an unexpected result was the maintenance of the tumor response, including tumor regression, for at least 2 weeks after treatment had ended.

Example 8

In Vivo Induction of Apoptosis by scL-TMZ in Cancer Stem Cells and Differentiated Cancer Cells Intracranial U87MG-luc2 tumor was induced in 5-6 week old female athymic nude mice as described above. Three weeks after inoculation, tumor bearing mice were randomly divided into groups and treatment was started. Animals were injected i.v. via the tail vein with 5 mg/kg (per injection per mouse) of TMZ alone or TMZ encapsulated in tumor targeting liposome complex. The scL-TMZ complex was prepared as described above using an anti-transferrin receptor single-chain antibody fragment (TfRscFv) as the targeting moiety, a Lip:TMZ molar ratio of 1:1 (liposome concentration=2 mM) and an TfRscFv to Liposome ratio if 1:30 (w:w). Control animals (Vehicle) received Liposome only (no TMZ, no TfRscFv). Prepared as described above, the sizes of the scL-TMZ liposomes iv injected into the mice during this study were found to average 85.5+4.96 nm (number average) (Mean+S.E.).

The mice were treated two times per week. After receiving 3 injections, all animals were euthanized and brains were harvested. Brain tumors were carefully dissected from normal brain tissue and weighed. The in vivo anti-tumor efficacy was evaluated by assessing the level of apoptosis. After weighing the tumors, single-cell suspensions were obtained from the tumors by collagenase digestion in Hank's balanced solution containing 1 mg/mL collagenase (Roche) and 2 mmol/L DNase I (Sigma) 1 h at 37° C. The fractionated cells were passed through a 70-μm cell strainer (Fisher Scientific, Pittsburgh, Pa.) and washed with PBS. To determine the level of apoptosis, single cells were stained with antibodies for cleaved caspase-3 (Cell Signaling Technology, Danvers, Mass.), and human CD133 (Miltenyi Biotec). The labeled cells were analyzed by flow-activated cell sorting (FACS) on BD FACS Aria flow cytometer (BD Biosciences, San Jose, Calif.).

Figure 13:
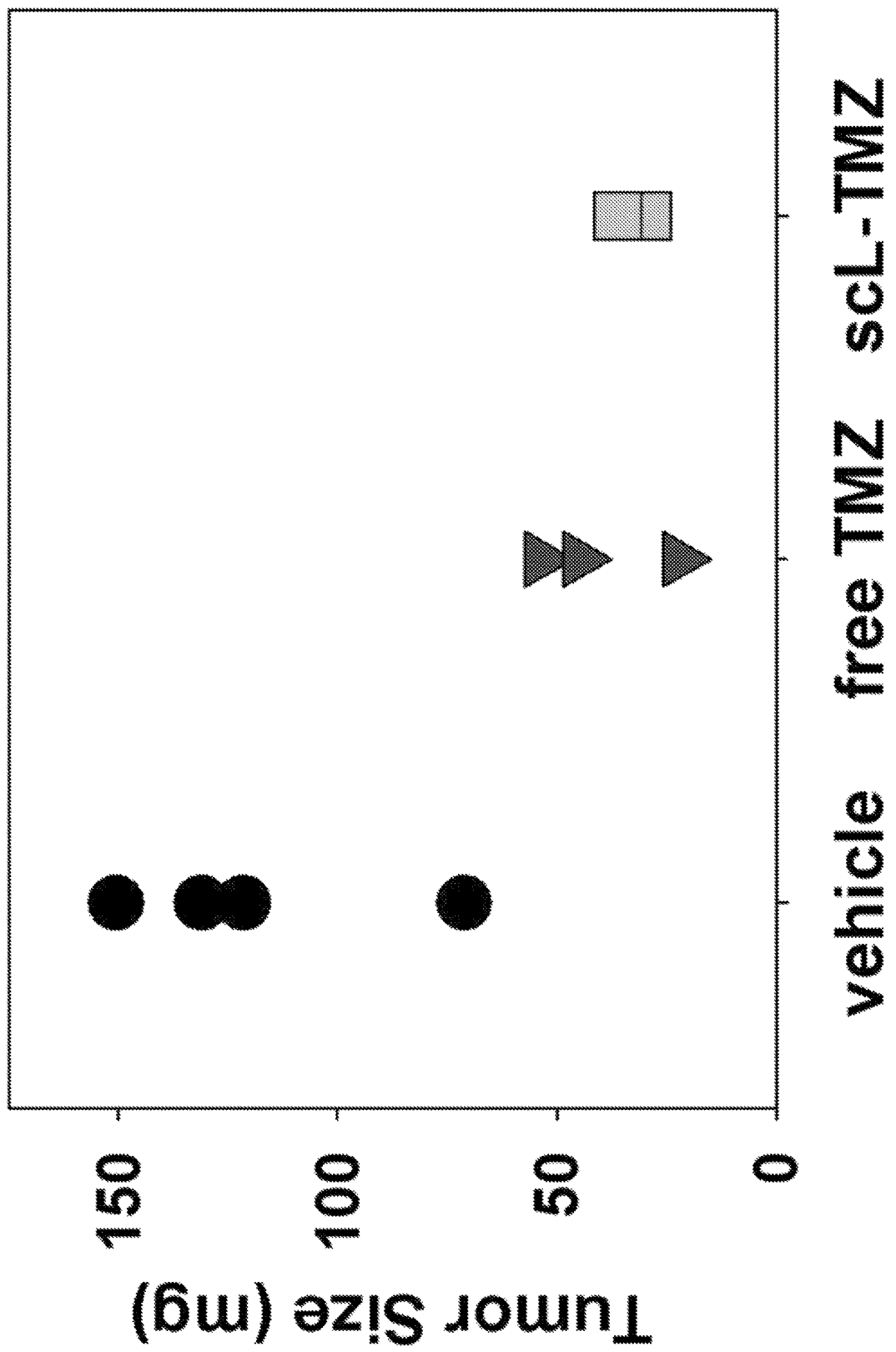
FIG. 13 shows weights of brain tumors demonstrating the effect of free TMZ and scL-TMZ.

Assessment of in vivo efficacy: The anti-tumor efficacy was assessed by evaluating the induction of apoptosis in the intracranial U87MG-luc2 brain tumors. The weights of the brain tumors after 3 iv injections of Vehicle (liposome only, no TMZ, no TfRscFv), Free unencapsulated TMZ or scL-TMZ are shown in FIG. 13. Unexpectedly, even after only three injections a difference in the tumor size between the free TMZ and scL-TMZ is evident.

Figure 14:
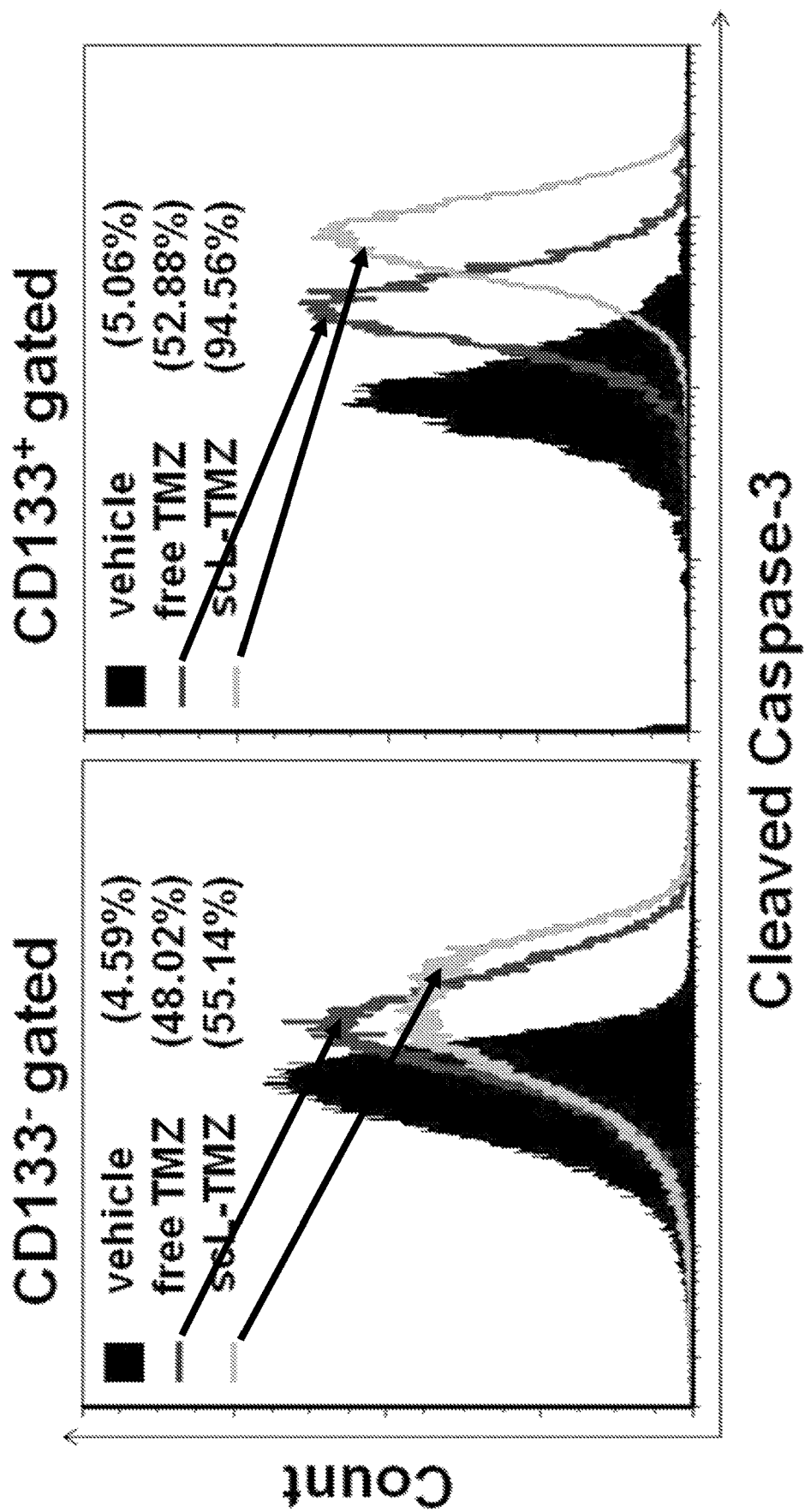
FIG. 14 shows results of flow cytometric analysis for the level of apoptosis as determined by cleaved caspase-3 antibody staining of single cells isolated from brain tumors.

Cancer stem cells (CSC) are often responsible for tumor recurrence and resistance to chemotherapy. Because of the unexpected finding described above wherein the tumor growth inhibition and even regression were observed after the end of treatment with scL-TMZ (but NOT with free TMZ), the level of apoptosis was assessed in cancer stem cells, as well as in differentiated cancer cells (non-CSC) in these tumors. FIG. 14 shows the results of flow cytometric analysis for the level of apoptosis as determined by cleaved caspase-3 antibody staining of single cells isolated from the brain tumors. CD133, a marker of GBM cancer stem cells (CSCs) was used to distinguish CSCs from differentiated cancer cells. The CSC population (CD133+) clearly show a significant increase in the % of cells undergoing apoptosis compared to free TMZ. Thus the scL-TMZ can target and efficiently transfect CSCs resulting in significant tumor cell death.

Results Summary: In an intracranial U87MG-luc2 GBM tumor xenograft model, intravenous treatment with scL-TMZ resulted in a significant inhibition of tumor growth demonstrated by tumor weight compared to those treated with free TMZ. In addition, intravenous treatment with scL-TMZ resulted in a significantly increased induction of apoptosis not only in CD133− differentiated cancer cells but also in CD133+ CSCs.

Example 9

In Vivo Efficacy of scL-TMZ in TMZ Resistant Brain Cancer Cell Line T98G Subcutaneous Xenograft Tumors T98G GBM tumor cells are known to be resistant to treatment with TMZ. For the TMZ-resistant GBM tumor model, subcutaneous T98G xenografts were used. T98G xenograft tumors were induced in female athymic nude mice by the subcutaneous injection of T98G cells or tumor particles suspended in Matrigel collagen basement membrane (BD Biosciences, San Jose, Calif.) on the lower back above the tail, two sites per mouse. When the subcutaneous T98G tumors reached ~100 to 300 $mm^3$, the mice were randomly divided into groups and i.v. injected with 25 or 66 mg/kg (per injection per mouse) of free TMZ or 25 mg/kg (per injection per mouse) TMZ encapsulated in tumor targeting complex (1:1 molar ratio). The scL-TMZ complex was prepared as described above in Example 1 using an anti-transferrin receptor single-chain antibody fragment (TfRscFv) as the targeting moiety, a Lip:TMZ molar ratio of 1:1 (liposome concentration=8 mM) and an TfRscFv to Liposome ratio if 1:30 (w:w). Control animals (Vehicle) received Liposome only (no TMZ, no TfRscFv). Prepared by the methods described above, the sizes of the scL-TMZ complexes iv injected into the mice during this study were found to average 130.8+13.5 nm (number average) (Mean+S.E.). The mice were treated once per day for 5 consecutive days. They were euthanized 48 hours after the last injection and the tumors harvested. Treatment was started on day 0.

Assessment of in vivo efficacy: The in vivo response of T98G subcutaneous tumors to treatment with either free TMZ or scL-TMZ complex was evaluated based upon the changes in tumor growth, body weight change, and induction of apoptosis. The size of each tumor was measured and tumor volume (L×W×H) in $mm^3$ was plotted versus time. Body weight change was also monitored during injection. The in vivo efficacy was further evaluated by assessing the level of apoptosis by TUNEL assay or cleaved caspase-3 staining with flow cytometry. Forty eight hours after the last injection the mice were euthanized and tumors harvested. Single-cell isolation was performed as described above. To determine the level of apoptosis, single cells were stained either for TUNEL assay or with antibodies for cleaved caspase-3, human CD133 and SSEA-1. SSEA-1 is known to be a marker for CSCs in GBM tumors. The labeled cells were analyzed by FACS.

Figure 15:
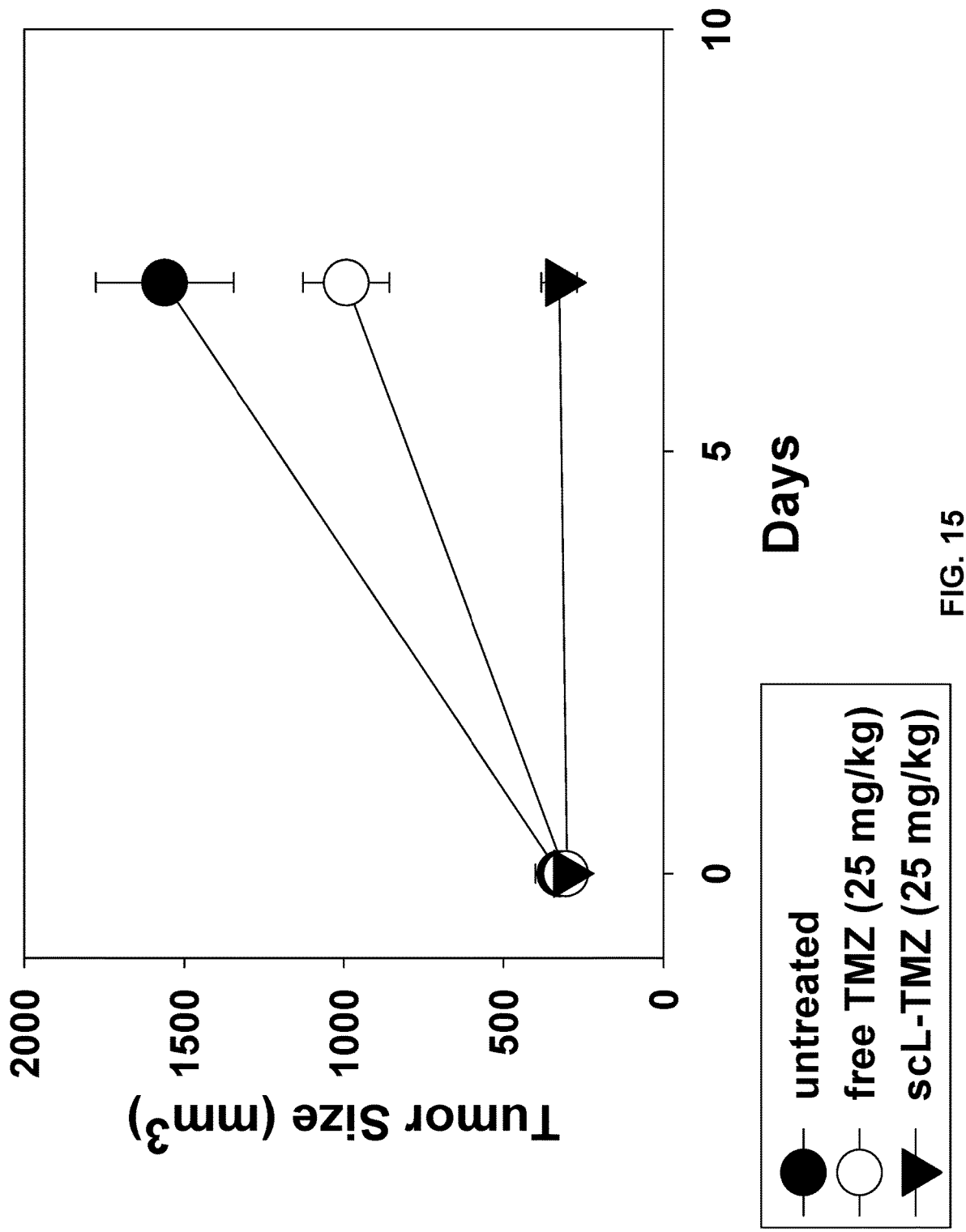
FIG. 15 shows tumor size for free TMZ and scL-TMZ treated mice.
Figure 16:
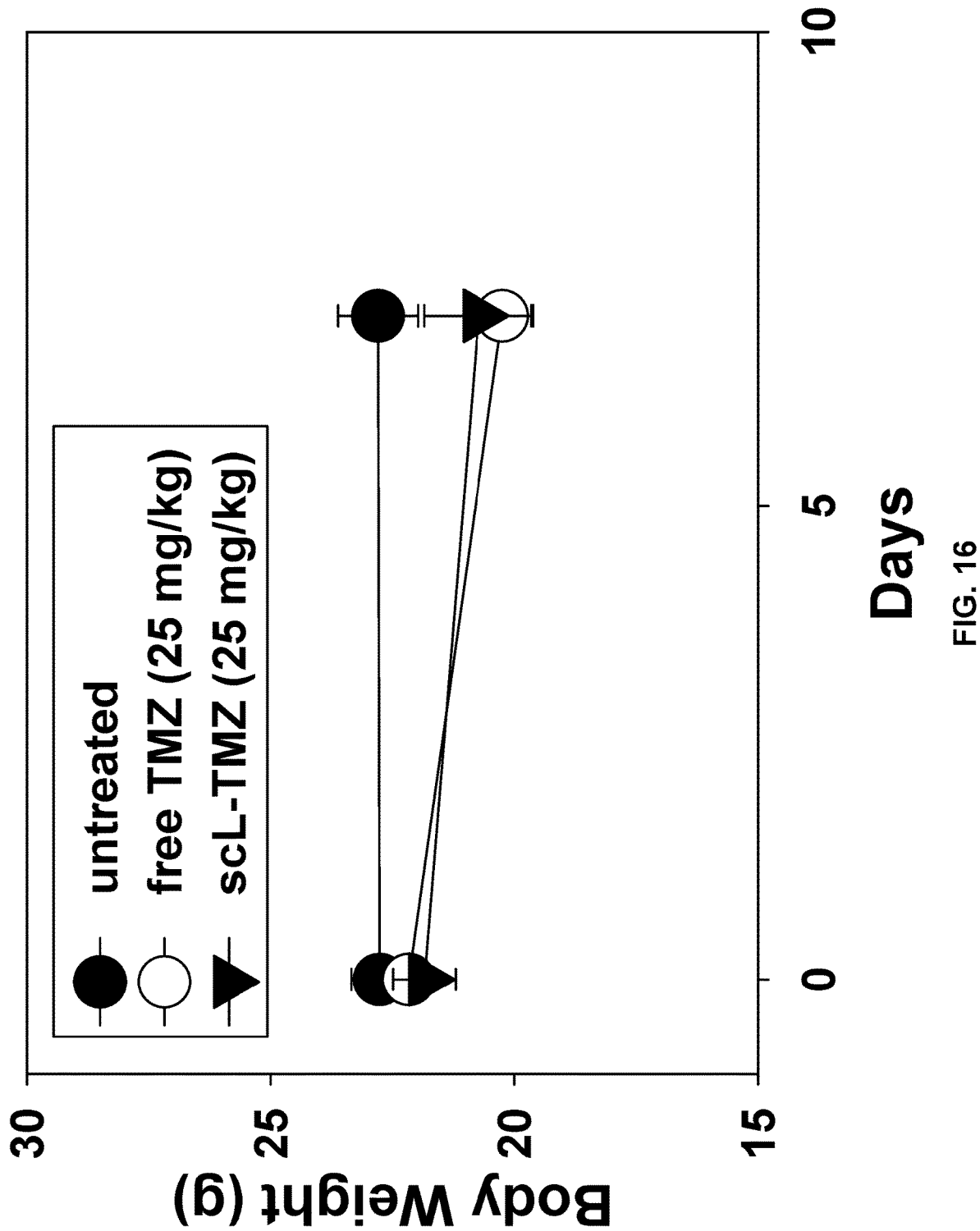
FIG. 16 shows body weight of mice treated with free TMZ and scL-TMZ.

The tumor size (volume in $mm^3$) of the tumors over this short period of time is shown in FIG. 15. Here again there is a significant difference in growth of these TMZ resistant tumors between those animals that received the free TMZ and the scL-TMZ complex, both administered at 25 mg/kg, in which there is significant tumor growth inhibition. As T98G tumors are known to be resistant to TMZ it is novel and unexpected that TMZ could control tumor growth. As discussed above for use in vitro, this reversal of resistance is due to the efficient delivery and uptake of the TMZ payload into the tumor cell by means of the binding of the targeting ligand (protein, antibody or antibody fragment) to its receptor on the cell and the triggering of uptake via through active transport mechanisms like receptor mediated endocytosis. This process "floods" the cells with drug overcoming the mechanisms the tumor cell has in place to repair the DNA damage caused by TMZ (such as upregulation of MGMT), and/or the mechanisms to pump the TMZ out of the cells. Thus the tumor cell and consequently the tumor dies. Based upon this in vivo data, the same mechanism works in vivo and thus demonstrates the potential use of the scL-TMZ complex as an anticancer agent for brain and other tumors, including those currently resistant to TMZ. The lack of toxicity of the iv administered scL-TMZ is indicated by the minimal change in body weight over the short term of this experiment (FIG. 16).

Figure 17:
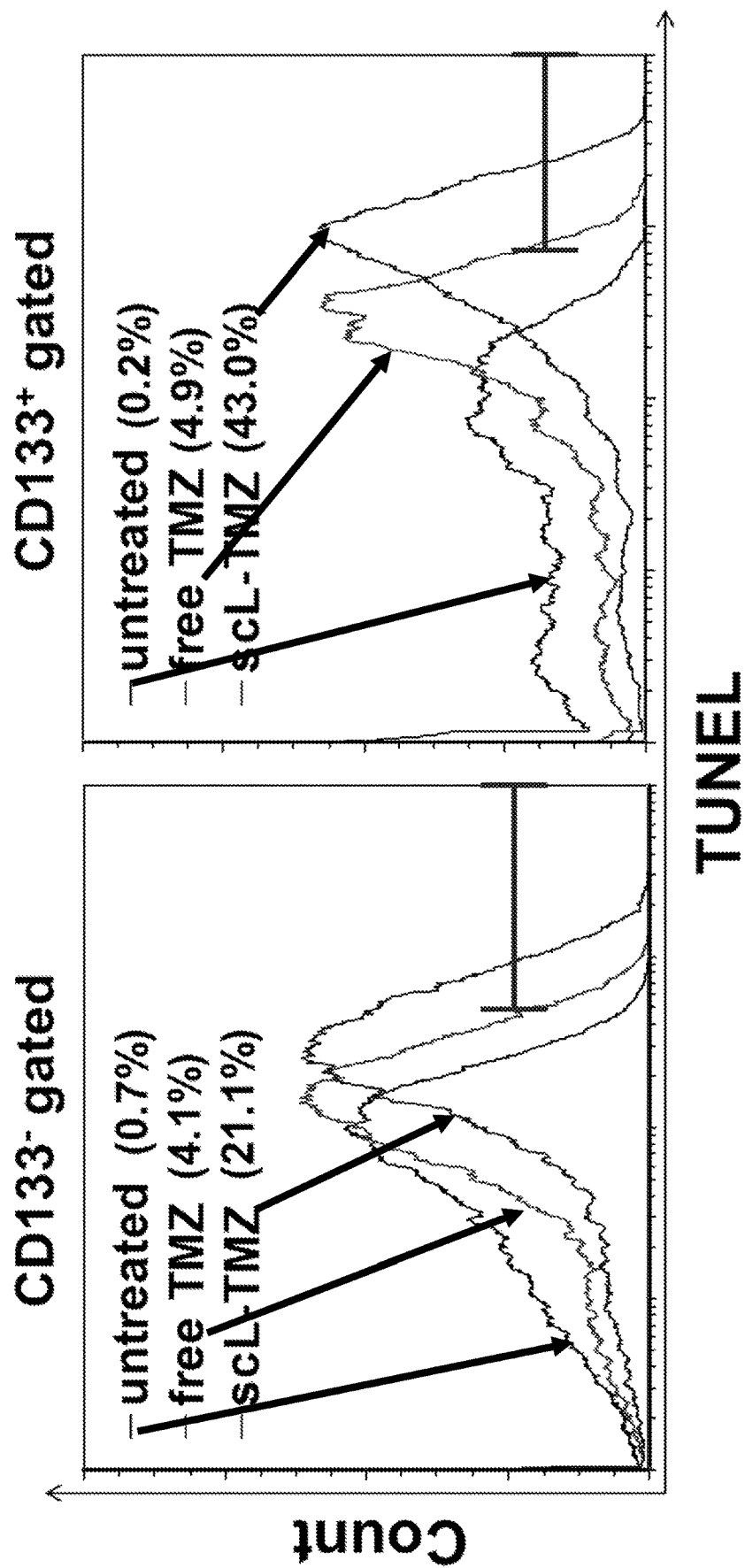
FIG. 17 shows TUNEL staining of CD133+ CSCs and CD133– non-CSCs isolated from subcutaneous T98G xenograft tumors after treatment.

The level of apoptosis in the tumors from animals that had been iv injected with 66 mg/kg (per injection per mouse) of free TMZ or 25 mg/kg (per injection per mouse) TMZ encapsulated in tumor targeting complex was assessed 8 hours post-injection by TUNEL staining of CD133+ CSCs and CD133− non-CSCs isolated from subcutaneous T98G xenograft tumors. As shown in FIG. 17, even though the animals were treated with more than double the dose of free TMZ compared to the amount of TMZ encapsulated in scL, the level of apoptosis induced by scL-TMZ was more than 5 fold higher in the non-CSCs and 8 fold higher in the CSCs.

Figure 18:
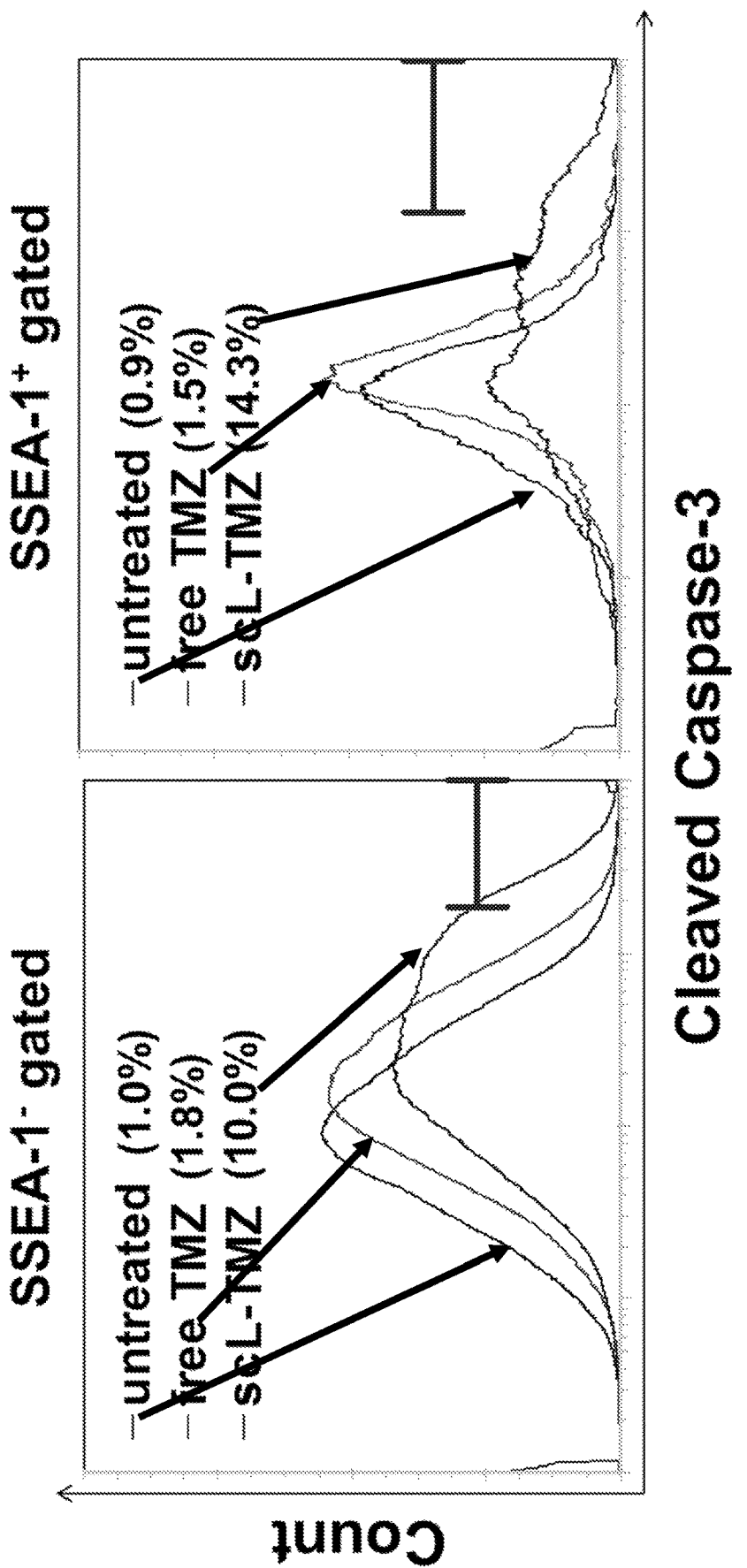
FIG. 18 shows levels of apoptosis assessed by cleaved caspase-3 antibody staining of SSEA-1+ CSCs from subcutaneous T98G brain tumors after treatment.

Similar results were obtained when the level of apoptosis was assessed by cleaved caspase-3 antibody staining of SSEA-1+ CSCs from the same subcutaneous T98G brain tumors (FIG. 18). SSEA-1, another marker of CSCs was used to distinguish CSCs from differentiated cancer cells. Here also the scL-TMZ induced a 5 fold (SSEA-1−) and 9.5 fold (SSEA-1+) higher level of apoptosis than free TMZ even though more than twice the amount of free TMZ was administered.

Results Summary: Compared to the treatment with free TMZ, intravenous treatment with scL-TMZ (at the same or even lower dose of TMZ) resulted in a significantly enhanced growth inhibition against TMZ-resistant T98G tumor xenografts. However, no significantly increased toxicity based upon body weight change was observed in scL-TMZ treated animals compared to those of free TMZ treated animals. In addition, intravenous treatment with scL-TMZ resulted in a significantly increased level of apoptosis not only in CD133− and SSEA-1− differentiated cancer cells, but also in CD133+ or SSEA-1+ CSCs.

These results demonstrate that delivery of TMZ by scL can induce massive apoptosis and overcome the inherent resistance of tumors cells (including, but not limited to brain, multiple myeloma, lung cancer, prostate cancer, liver cancer, ovarian cancer, pancreatic cancer, head and neck cancer, kidney cancer, melanoma, stomach cancer) to this drug.

Example 10

Combination Therapy for TMZ-Resistant Tumors

Although the first-line chemotherapeutic agent Temozolomide (TMZ) has shown benefit in patients with brain tumors, it also has significant therapeutic dose limiting toxicities (Villano J L, Seery T E and Bressler L R (2009) Temozolomide in Malignant Gliomas: Current Use and Future Targets. Cancer Chemotherapy and Pharmacology 64: pp 647-655), including myelosuppression. Thus, ways to tumor-target TMZ so that it is specifically and efficiently delivered to, and taken up by, tumor cells in the brain thereby reducing non-specific toxicities, would be of significant benefit to those patients who are currently candidates for use of this drug.

However, even if efficiently delivered to the tumor cells, one significant drawback to the widespread use of TMZ for glioblastomas and other brain cancers is that a significant percent of tumors are resistant to TMZ. This is primarily due to overexpression of $O^6$-methylguanine-DNA-methyl transferase (MGMT), which repairs the TMZ-induced DNA lesions by removing the $O^6$-guanine adducts (Mrugala M M, Adair J and Kiem H P (2010) Temozolomide: Expanding Its Role in Brain Cancer. Drugs of Today 46: pp 833-846), thus negating the therapeutic action of TMZ. Therefore, it is imperative to develop ways to overcome this resistance.
Tumor-Targeting scL-p53 Nanocomplex for Gene Therapy As described in U.S. Pat. No. 7,780,822, the disclosure of which is incorporated by reference herein in its entirety, a delivery system carrying a plasmid DNA encoding the wtp53 gene and targeted via TfRscFv (scL-p53) has been successfully developed. scL-p53 has also been developed for use in combination with chemotherapy/radiation to increase the tumor response to these standard therapeutic modalities.

Although TMZ is a first-line chemotherapeutic for the treatment of brain tumors, only a subset of GBM patients respond to this drug. Based on the work of Stupp et al., (Stupp R, Hegi M E, Mason W P, van den Bent M J, Taphoorn M J B, Janzer R C, Ludwin S K, Allgeier A, Fisher B, Belanger K, Hau P, Brandes A A, Gijtenbeek J, Marosi C, Vecht C J, Mokhtari K, Wesseling P, Villa S, Eisenhauer E, Gorlia T, Weller M, Lacombe D, Cairncross J G and Mirimanoff R O (2009) Effects of Radiotherapy With Concomitant and Adjuvant Temozolomide Versus Radiotherapy Alone on Survival in Glioblastoma in a Randomised Phase III Study: 5-Year Analysis of the EORTC-NCIC Trial. Lancet Oncology 10: pp 459-466) as well as that of Hegi et al., (Hegi M E, Diserens A, Gorlia T, Hamou M, de Tribolet N, Weller M, Kros J M, Hainfellner J A, Mason W, Mariani L, Bromberg J E C, Hau P, Mirimanoff R O, Cairncross J G, Janzer R C and Stupp R (2005) MGMT Gene Silencing and Benefit From Temozolomide in Glioblastoma. New England Journal of Medicine 352: pp 997-1003) two distinct groups of patients were indentified regarding response to TMZ treatment: those with a downregulated MGMT promoter with better prognosis and those with an active MGMT promoter with worse prognosis.

Thus, development of a means to down-regulate MGMT would increase the number of patients that respond to TMZ. There have been a number of reports indicating that increasing wtp53 expression could down-regulate expression of DNA repair genes such as MGMT (Bocangel D, Sengupta S, Mitra S, Bhakat K. K (2009) P53-Mediated Down-Regulation of the Human DNA Repair Gene 06-Methylguanine-DNA Methyltransferase (MGMT) Via Interaction With Sp1 Transcription Factor. Anticancer Research; Harris L C, Remack J S, Houghton P J and Brent T P (1996) Wild-Type P53 Suppresses Transcription of the Human 06-Methylguanine-DNA Methyltransferase Gene. Cancer Research 56: pp 2029-2032; Srivenugopal K S, Shou J, Mullapudi S R S, Lang F F, Rao J S and Ali-Osman F (2001) Enforced Expression of Wild-Type P53 Curtails the Transcription of the 06-Methylguanine-DNA Methyltransferase Gene in Human Tumor Cells and Enhances Their Sensitivity to Alkylating Agents. Clinical Cancer Research 7: pp 1398-1409). The use of the scL-p53 nanocomplex, shown to efficiently target primary and metastatic tumors and to cross the BBB, should be an effective means to overcome the MGMT induced resistance to TMZ observed in a significant percentage of GBM and other tumors, thus broadening the application of this drug for use in, and improving the prognosis of, patients with primary and metastatic brain tumors. Moreover, since TMZ is also being evaluated for use in other non-brain refractory or advanced malignancies including pancreatic, neuroendocrine and areodigestive tract cancers (Tentori L and Graziani G (2009) Recent Approaches to Improve the Antitumor Efficacy of Temozolomide. Current Medicinal Chemistry 16: pp 245-257.), treatment with scL-p53 will enhance the potential of TMZ to be an effective therapeutic agent for a variety of cancers.
scL-TMZ and scL-p53 Combination Therapy Described herein is the use of the combination of scL-TMZ and scL-p53. The development of scL-TMZ for use as a monotherapy will be of benefit to patients that currently are candidates for TMZ treatment. However, the combinatorial approach will have an even greater therapeutic potential. The decreased tumor resistance due to scL-p53, along with the improved properties that result from tumor-targeted delivery of scL-TMZ, would result in converting currently TMZ unresponsive brain tumors (and possibly other cancers) to responsive. Therefore, this approach has the potential to be developed into a new, less toxic, more effective therapeutic regimen for the treatment of GBM and other cancers.

Experimental Approach

The experiments are designed to demonstrate development of a new, more effective treatment regimen for GBM with use of scL-TMZ, both alone and when used in combination with scL-p53.

Human Brain Tumor Cell Lines and In Vivo Models

Human brain cancer cell lines U87MG and T98G were described above. A version of U87MG that stably expresses the luciferase gene has been obtained from Caliper Life Sciences for use in in vivo studies where tumor growth and response will be monitored by the IVIS® Imaging System Xenogen.

Imaging Protocol

The MR imaging for brain tumors will be performed on a 7T Bruker Biopsin (Billerica, Mass.) horizontal spectrometer/imager with a 20 cm bore equipped with 100 gauss/cm microimaging gradients and run by Paravision 4.0 software. The imaging protocol is a T1-weighted Turbo rapid acquisition with rapid enhancement three-dimensional imaging sequence as previously described (Haggerty T, Credle J, Rodriguez O, Wills J, Oaks A W, Masliah E and Sidhu A (2011) Hyperphosphorylated Tau in an Alpha-Synuclein-Overexpressing Transgenic Model of Parkinson's Disease. European Journal of Neuroscience 33: pp 1598-1610).

Demonstration of In Vivo Efficacy of scL-TMZ Alone and in Combination with scL-p53

In these studies, the U87-Luc orthotopic intracranial (TMZ sensitive) and T98G (TMZ resistant) subcutaneous tumor models will be used to examine the effect of scL-TMZ alone and in combination with scL-p53 on tumor growth and/or regression. It should be noted that although U87MG has wt p53, an increased in vivo response is observed when U87 intracranial tumors are treated with the combination of scL-p53 and free TMZ. Groups of mice (6 mice/group/tumor model) will receive i.v (tail vein) injections of Free TMZ alone, scL-TMZ alone, scL-p53 alone, scL-p53 plus free TMZ or scL-TMZ. Untreated mice will serve as controls. The p53 dose will be 30 ug/mouse/injection, and TMZ will be used at 5 mg/kg. Both treatments will be administered twice weekly for 5 weeks. Tumor growth inhibition/regression will be assessed by size for T98G and with the Xenogen for the intracranial tumors where tumor volume will be determined by MRI. Xenogen/MRI imaging will be done pre-treatment, once/week during treatment and immediately after treatment has ended. Half-way through treatment, tumors and various normal organs and tissues will be taken from 3 mice in each group and coded. Half of each tissue will be used for the analysis of cancer stem cell targeting and the remainder examined by histology for markers of apoptosis (Tunnel, Caspase-3) and for proliferation marker Ki67. One day after treatment has ended, 3 mice will be humanely euthanized and necropsied by a commercial CRO (BioReliance, Rockville Md.) to look for differences in myelotoxic effects and lymphopenia associated with TMZ.

In Vitro Results

Figure 19:
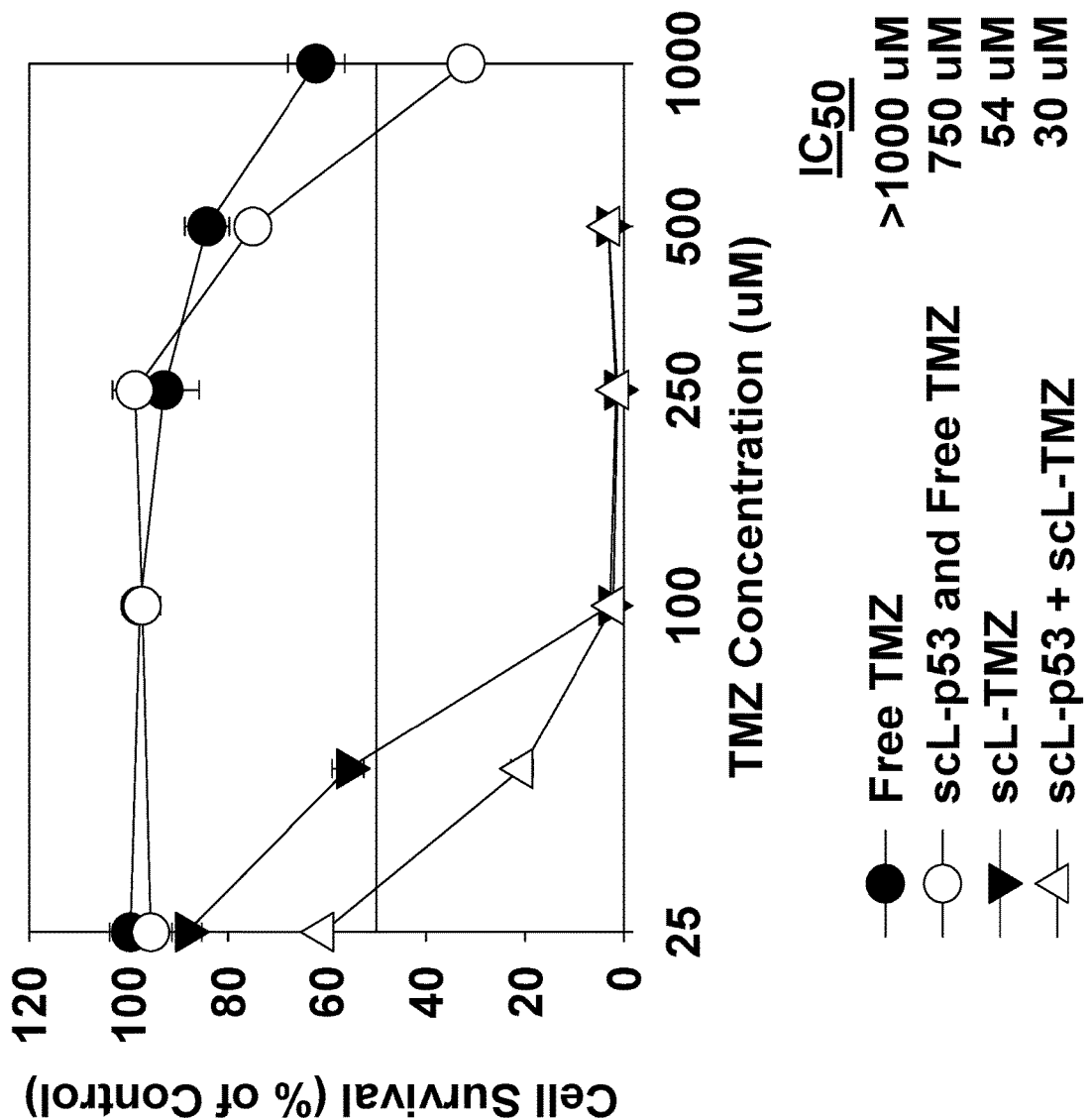
FIG. 19 shows T98G cell survival versus concentration of TMZ for free TMZ, scL-TMZ, as described herein and the combination scL-TMZ along with targeted cationic liposomes expressing the p53 gene.

To test the hypothesis that treatment with scL-p53 could down modulated MGMT activity and sensitize TMZ resistant brain tumors to this drug, a preliminary XTT cell survival assay was performed. TMZ resistant T98G cells were plated at $2\times10^3$ per well in a 96-well plate and transfected with scL-p53 in combination with either Free TMZ or scL-TMZ. The cells were also transfected with just free TMZ or just scL-TMZ. The XTT assay was performed 90 h later and the $IC_{50}$ values (the concentration yielding 50% growth inhibition) determined. Transfection with scL-p53 in combination with either free or scL complexed TMZ resulted in an increased level of response compared to single agent TMZ in this known TMZ resistant cell line (Patil R, Portilla-Arias J, Ding H, Inoue S, Konda B, Hu J W, Wawrowsky K A, Shin P K, Black K L, Holler E and Ljubimova J Y (2010) Temozolomide Delivery to Tumor Cells by a Multifunctional Nano Vehicle Based on Poly (Beta-L-Malic Acid). Pharmaceutical Research 27: pp 2317-2329) (FIG. 19). Moreover, compared to free TMZ alone, transfection with the scL-TMZ nanocomplex resulted in a significant level of chemosensitization to the drug.

Example 11

Figure 20:
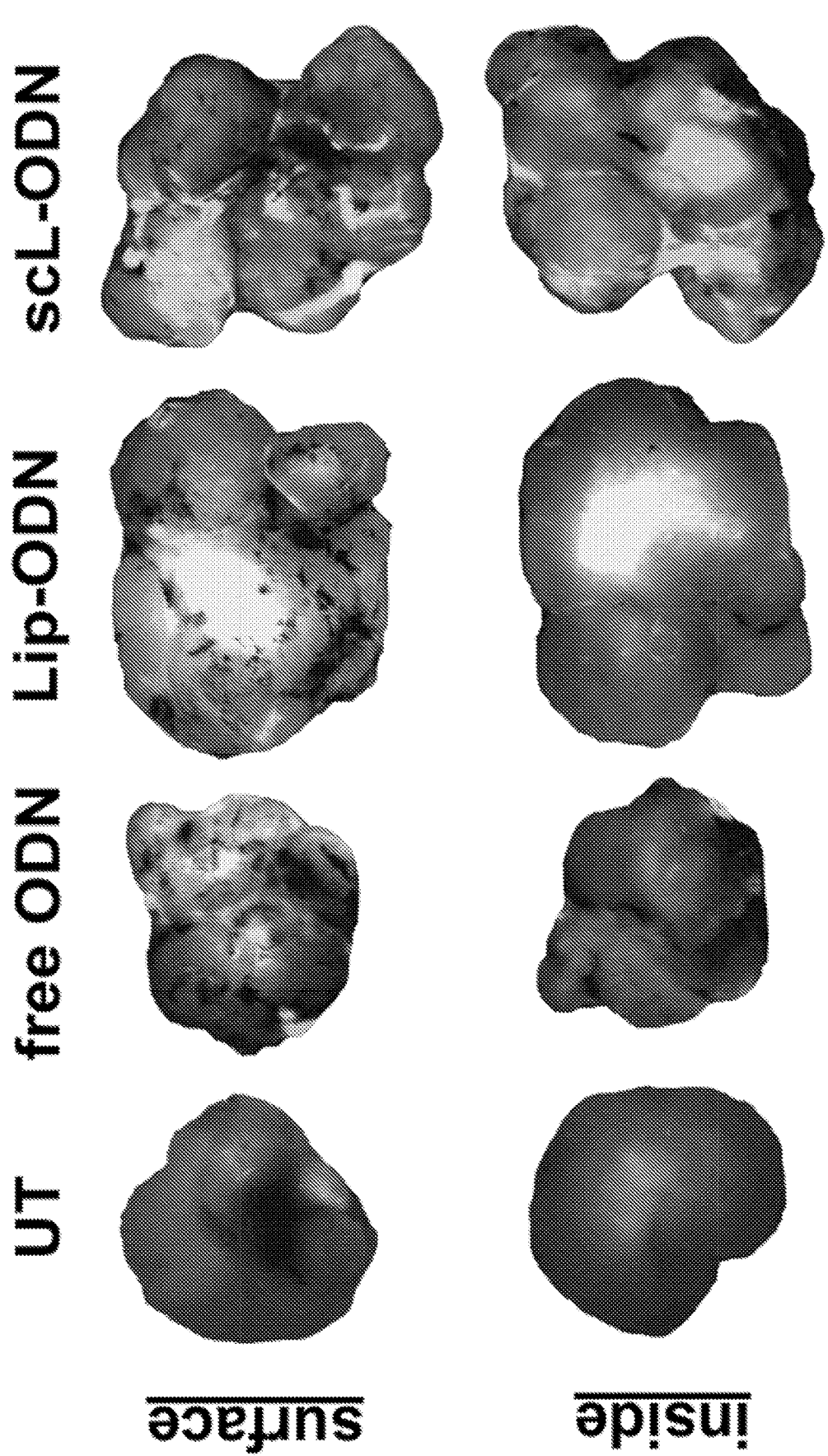
FIG. 20 shows tumor-targeted delivery of systemically administered scL-6FAM-ODN to U251 xenograft brain tumors.

In Vivo Targeting of Cancer Stem Cells by Systemically Administered scL-Complex in a Mouse Brain Tumor Model Human brain tumor xenografts were induced in nude mice by subcutaneous inoculation of U251 cells. Three weeks later, the mice were I.V. injected with 6FAM-ODN (100 µg/mouse) administered as either uncomplexed free 6FAM-ODN, scL-6FAM-ODN (scL-ODN), or the unliganded Lip-6FAM-ODN (the liposome without the targeting moiety) (LIP-ODN). 24 hours post-injection, the tumors were imaged using the Maestro™ in vivo fluorescence imaging system to determine the level of fluorescence in the tumors. After Maestro™ imaging, single cells were isolated from the tumors by enzyme digestion, and the amount of 6FAM-ODN uptake in CD133+(Cancer Stem Cell (CSC)) and CD133- (non-CSC) cells analyzed and quantitated by FACS. Systemic administration of both free 6FAM-ODN and unliganded Lip-ODN resulted in very little, if any, fluorescence in the tumors. In contrast, a strong fluorescence signal was evident in the tumor from the mouse that received the scL-ODN nanocomplex (FIG. 20).

Figure 21:
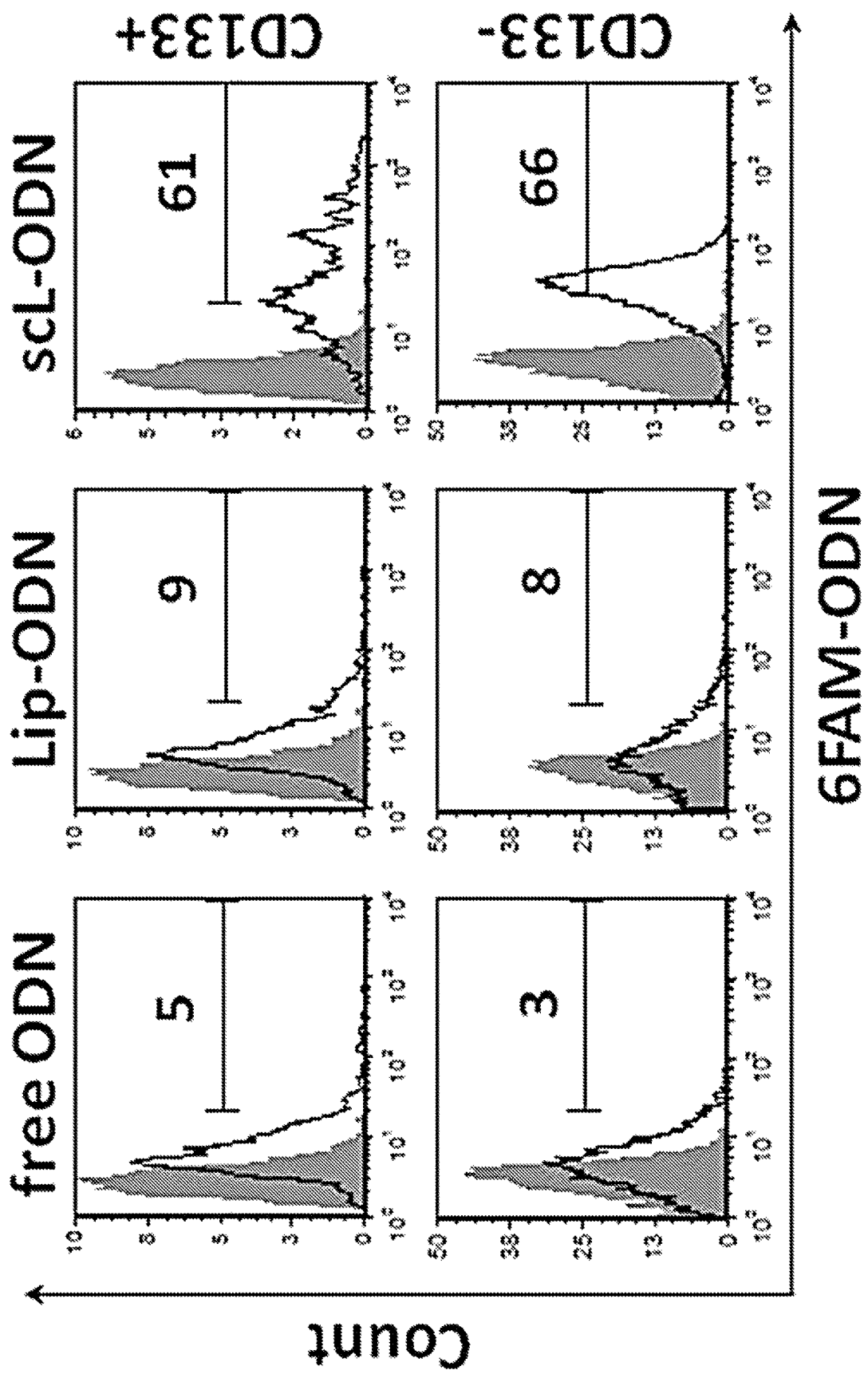
FIG. 21 shows flow cytometric analysis of scL-delivered 6FAM-ODN uptake in CD133+ and CD133– non-CSC cells isolated from U251 xenograft tumors after systemic administration.

More importantly, this significant difference was also reflected in the transfection efficiency of CSCs (FIG. 21). Whereas less than 10% of the CSC and Non-CSC cells were transfected with the free or unliganded 6FAM-ODN, >60% of both CSC and non-CSC cell populations demonstrated the presence of the payload after I.V. injection. Gray histograms represent untreated controls. These findings confirm that with systemic administration, the scL delivery system described herein can target and efficiently deliver payloads to CSCs in vivo.

Example 12

Figure 22:
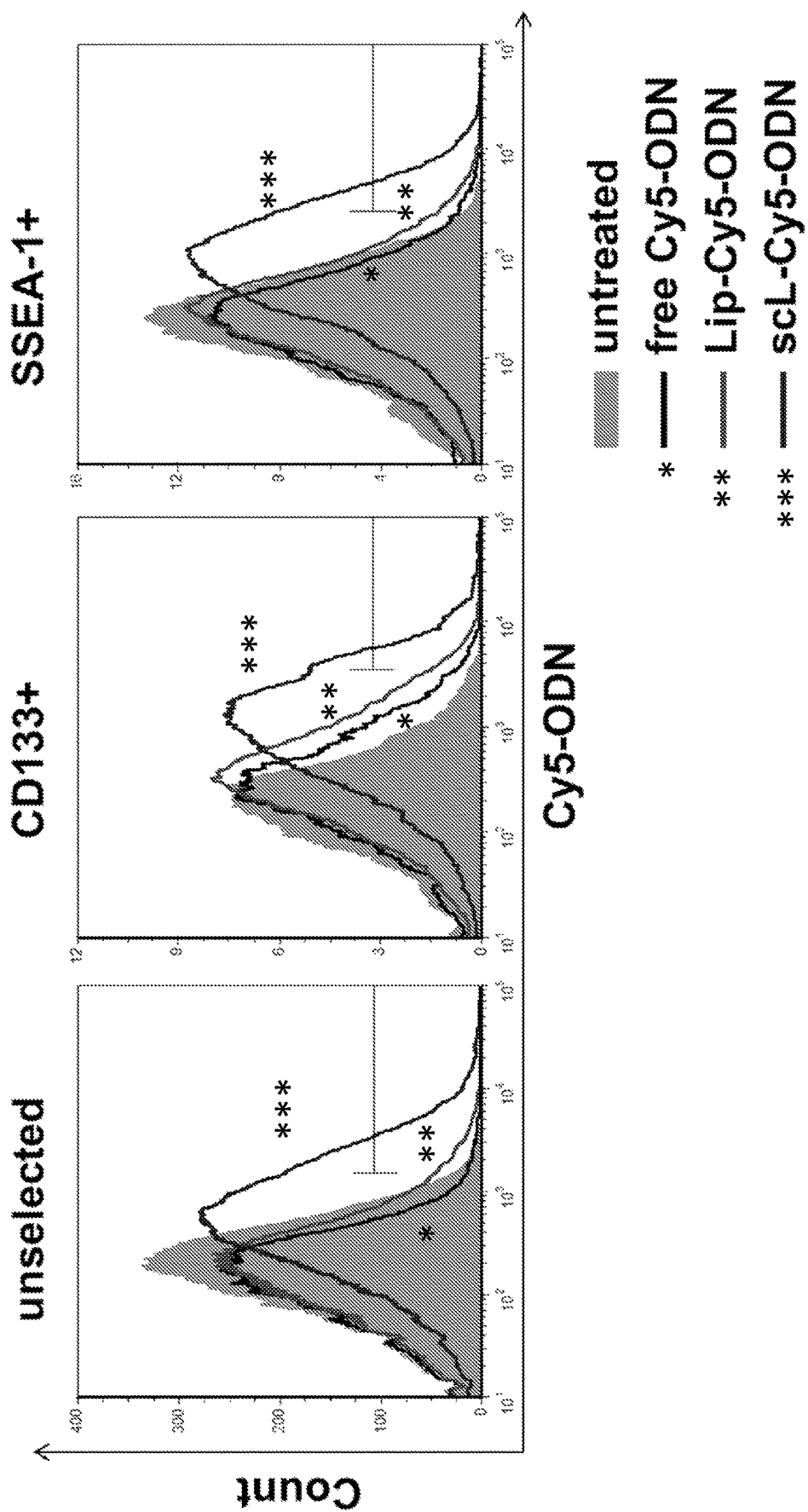
FIG. 22 shows tumor specific targeting of CSCs in IC GBM by scL-Delivered ODN after systemic administration.

Tumor Specific Targeting of CSCs in IC GBM by scL-Delivered ODN After Systemic Administration FIG. 22 shows the comparison of in vivo delivery efficiency of payload delivered by tumor-targeting complex, non-targeting complex, and payload itself without the delivery system in an animal model of intracranial U87MG-luc2 glioblastoma multiforme (GBM) brain tumors. Fluorescently labeled (Cy5) oligonucleotide (Cy5-ODN) was encapsulated in tumor-targeted complexes (scL-Cy5-ODN) (prepared as described in U.S. Pat. No. 7,780,882) or complexes without tumor-targeting ligand (Lip-Cy5-ODN). Twenty five micrograms of Cy5-ODN (free or encapsulated with or without the targeting moiety) were injected intravenously to each animal bearing a U87MG-luc2 intracranial tumor. At 60 hr after injection, the animals were euthanized and tumors were harvested to assess the efficiency of delivery to cancer stem cells (CSCs) in these intracranial tumors by flow cytometry using markers for cancer stem cells, CD133 and SSEA, both of which are known by those familiar with the art to be markers of CSC in general (CD133+) and CSC in brain tumors (SSEA-1+). Single cells were isolated from brain tumors and subjected to FACS analysis after staining with CSC marker antibodies (CD133+ or SSEA-1+). The shift in the curve in each histogram in FIG. 22 represents Cy5-ODN uptake in cancer stem cells. Only the curves representing the CSCs isolated from the mice receiving the scL-Cy5-ODN demonstrated a significant shift, indicating that neither the free Cy5-ODN, nor the Lip-Cy5-ODN (without the targeting moiety) efficiently transfected CSCs in the brain tumor.

Example 13

In Vitro Sensitization of Brain Tumor Cells to Temozolomide (TMZ) by scL-p53

To assess the ability of scL delivered wtp53 to sensitize brain tumor cells to first-line chemotherapeutic agent TMZ, human brain tumor derived U87 and U251 cells were treated with TMZ alone, or the combination of TMZ plus scL-p53 (prepared as described in U.S. Pat. No. 7,780,882). As a control, cells were also treated with the combination of TMZ and the scL delivery system carrying the same vector used to construct the pSCMVp53 plasmid, but without the p53 insert (scL-vec). The cells were plated in a 96-well plate and treated 24 hours later with scL-p53 or scL-vec. 6 hours post-transfection, the TMZ was added in increasing concentrations. The XTT assay was performed 144 h after the addition of the TMZ to the wells and the $IC_{50}$ values (the concentration yielding 50% growth inhibition) determined. As these two cell lines are known to be sensitive to TMZ, it was not unexpected that there was some response to TMZ alone. However, as shown in FIG. 23, there is a significant increase in sensitization to TMZ when the cells are transfected with wtp53 delivered by the scL delivery system when compared to TMZ alone for both cell lines. Minimal to no sensitization (U87 and U251, respectively) was observed with the complex carrying the empty vector, demonstrating that the effect is due to the p53 and not the delivery system.

However, as only a subset of brain tumor patients respond to TMZ it was more critical to assess the ability of scL-p53 to sensitize TMZ resistant tumors to this chemotherapeutic agent. Thus, to assess the ability of scL delivered wtp53 to sensitize TMZ resistant brain tumor cells to this first-line chemotherapeutic agent, human brain tumor derived LN-18 and T98G cells were treated with TMZ alone, or the combination of TMZ plus scL-p53 (FIG. 23). As a control, cells were also treated with the combination of TMZ and the scL delivery system carrying the same vector used to construct the pSCMVp53 plasmid, but without the p53 insert (scL-vec). The cells were plated in a 96-well plate and treated 24 hours later with scL-p53 or scL-vec. 24 hours post-transfection, the TMZ was added in increasing concentrations. The XTT assay was performed 72 h after the addition of the TMZ to the wells and the $IC_{50}$ values (the concentration yielding 50% growth inhibition) determined. As shown in FIG. 23 with LN-18 cells, after transfection with scL-p53 these TMZ resistant cells are now responding to even very low doses of TMZ. More than 50% of the cells are killed at a dose of TMZ as low as ~50 uM compared to TMZ alone, in which no significant cell death is observed until a dose of ~1000 uM. With the T98G cells (FIG. 23), although not as responsive as to TMZ as LN-18 after treatment with scL-p53, these highly resistant cells are also sensitized to the killing effects of this drug. The cells treated with scL-p53 prior to exposure to TMZ have an $IC_{50}$ of 600 uM while those receiving TMZ only do not reach $IC_{50}$ until the TMZ dose is ~2000 uM. As above, there is minimal or no effect on the response of the cells to TMZ after transfection with the control scL-vec indicating that the response in these resistant cell lines is due to the presence of wtp53.

Example 14

In Vivo Sensitization of Brain Tumor Cells to Temozolomide (TMZ) by Systemically Administered scL-p53

Figure 24:
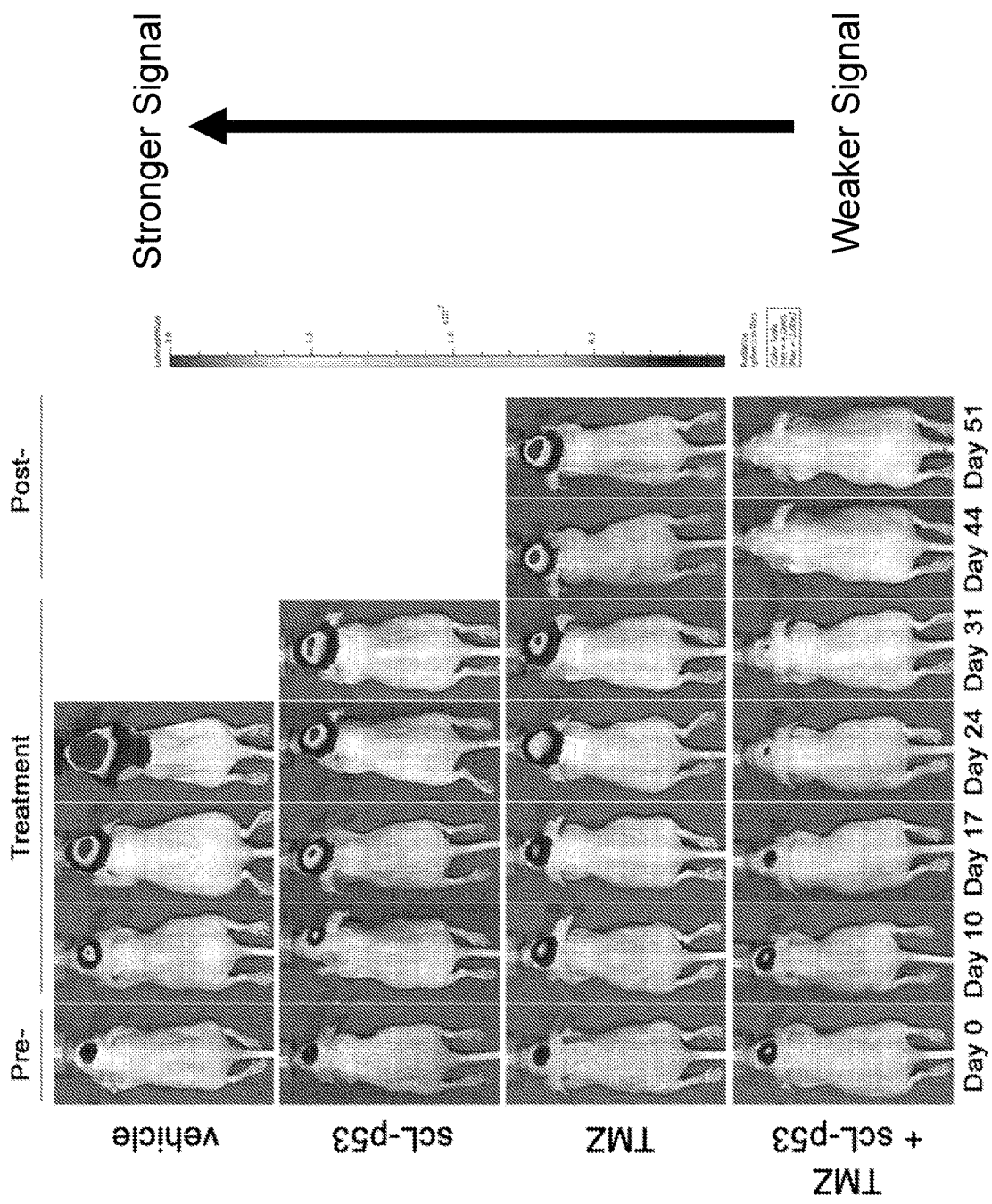
FIG. 24 shows bioluminescence imaging of U87 IC tumors using Xenogen showing the synergistic effect of the combination of SGT-53+TMZ.
Figure 25:
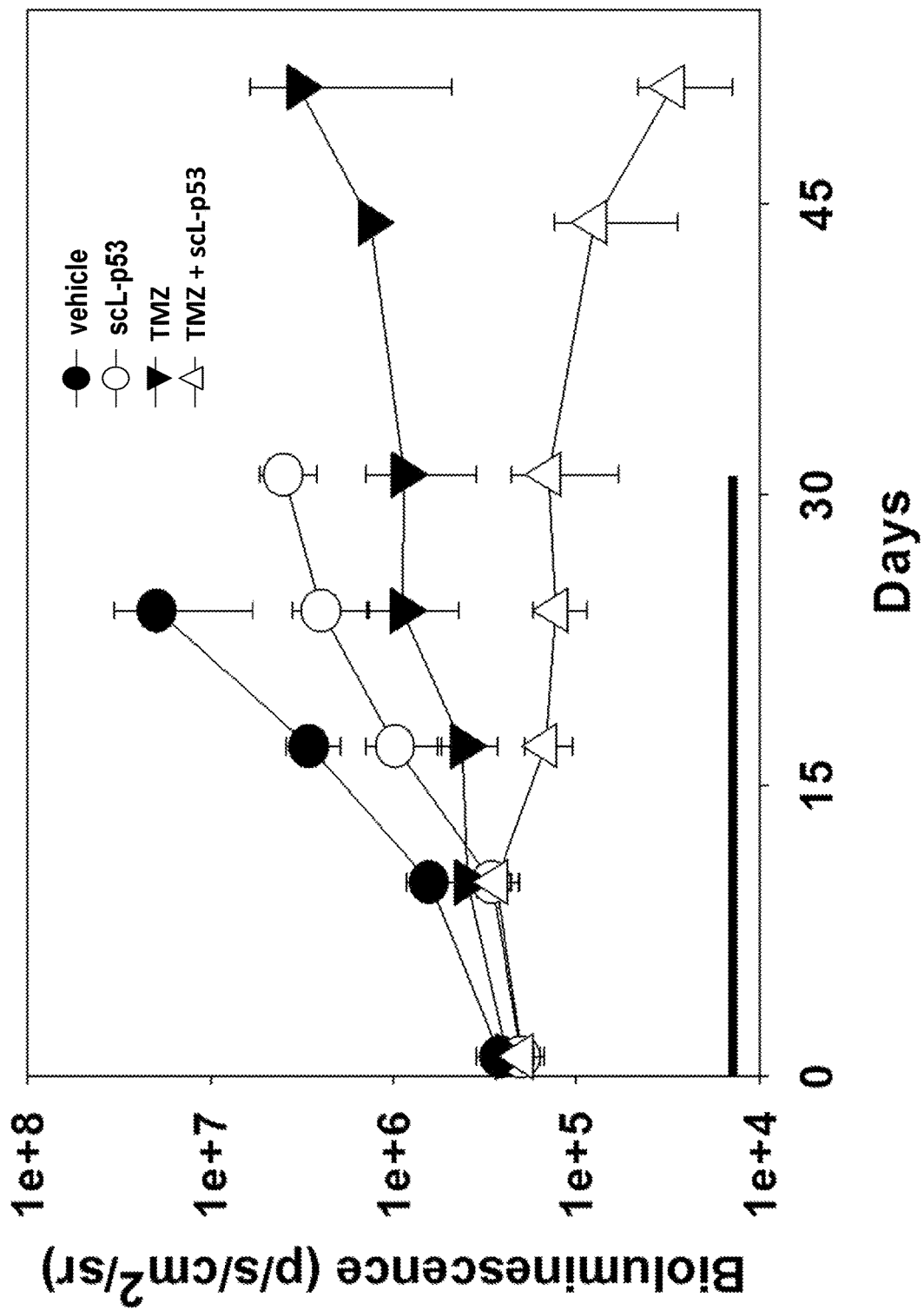
FIG. 25 shows the synergistic effect of SGT-53 plus TMZ on intracranial (IC) U87 glioblastoma multiforme (GBM).

Tumor Regression in an Intracranial (IC) Mouse Model of Brain Cancer Induced by Systemic Treatment with the Combination of scL-p53 Plus TMZ An experiment was performed to examine tumor growth inhibition induced by the sensitization of IC brain tumors to TMZ by systemic administration of scL-p53 prepared as described in U.S. Pat. No. 7,780,882. U87MG-Luc xenograft brain tumors were induced in nude mice by intracranially inoculating U87MG-luc cells. This cell line, obtained from Caliper Life Sciences, has been modified to stably express the Luciferase gene. 10 days post-inoculation, tumor-bearing animals were i.v. tail vein injected with TMZ alone (5.0 mg/kg/injection), scL-p53 alone (30 ug DNA/mouse/injection) or TMZ in combination with scL-p53. As a control, one group received PBS (vehicle). All i.v. injections were administered 2x/week to a total of 10 injections. To assess tumor response, bioluminescence imaging (BLI) was performed using IVIS® Imaging System's Xenogen. FIG. 24 is a comparison of in vivo anti-tumor efficacy of the various groups. Bioluminescence signals which correlate to tumor size are shown in a color map. Red color (at the top of the scale bar): the stronger signal, Violet color (at the bottom of the scale bar): the weaker signal. The bioluminescence intensity of the brain tumors, a measure of tumor size/growth, was compared between groups using Xenogen Living Image® software and is plotted over time in FIG. 25. The horizontal bar indicates the duration of treatment (Last treatment=Day 24).

While TMZ alone and scL-p53 alone had some minimal effect on IC tumor growth during treatment, the tumors in both groups rapidly increased in size after the end of treatment. In contrast, the tumors in the group of mice that received the combination of scL-p53 and TMZ displayed not only tumor growth inhibition, but tumor regression during treatment. More significantly, this regression continued for more than 20 days after treatment had ended.

Figure 26:
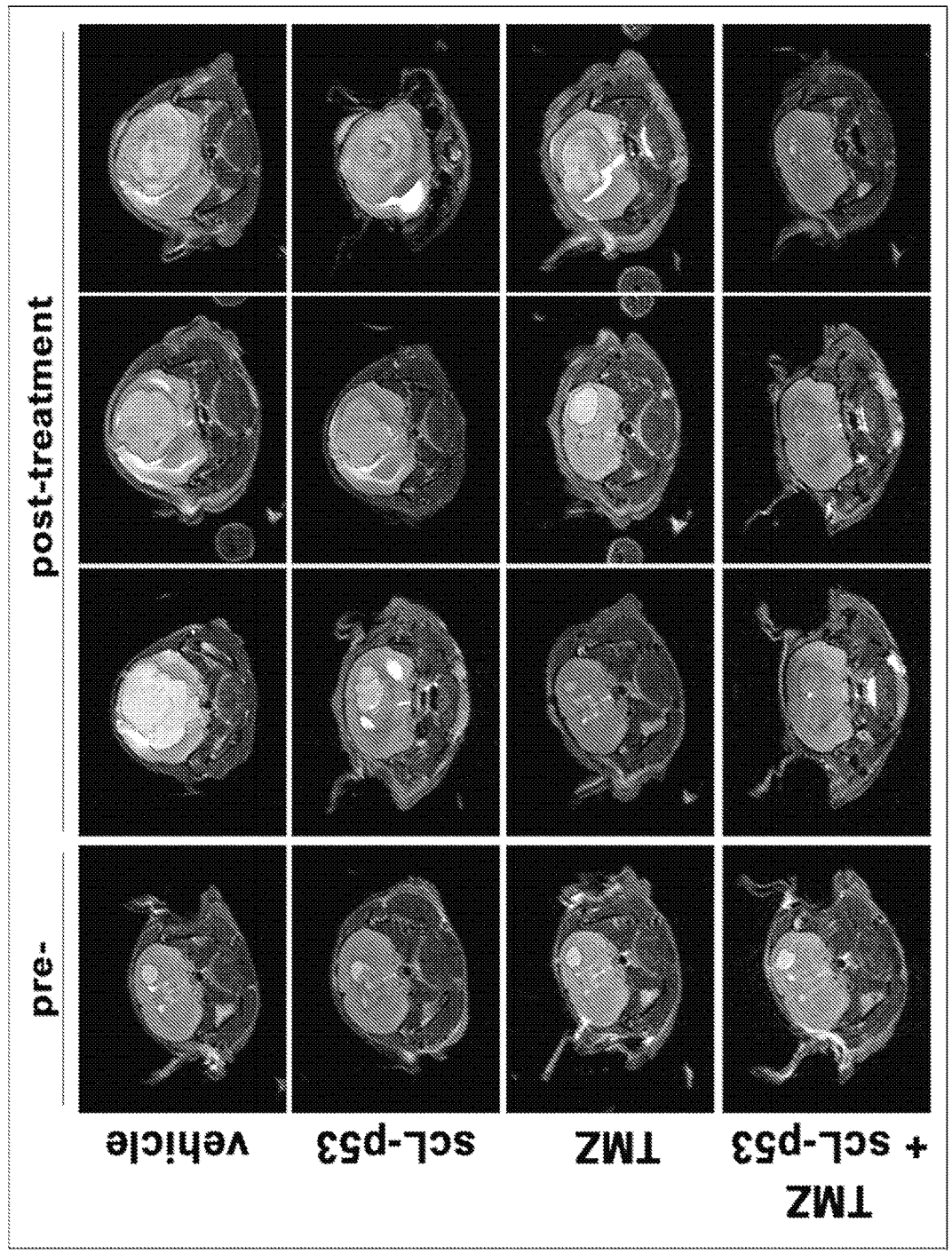
FIG. 26 shows the synergistic Effect of the combination of systemically administered scL-p53 plus TMZ.

To confirm the bioluminescence findings, the mice were also imaged by MRI, without contrast agent, before and after the mice received 3 weeks of treatment. The tumor regression observed in the combination treatment group by bioluminescence was also observed here. In FIG. 26 the outlines indicate the glioblastoma tumors. It is evident that instead of increasing in size post treatment as is evident in the single agent treatment groups, any residual tumor is barely detectable in the these animals that received both scL-p53 and TMZ. Therefore, this experiment demonstrates that the presence of scL-delivered wtp53 can sensitize GBM tumors to TMZ leading to significant tumor response (regression) not just tumor growth inhibition.

Figure 27:
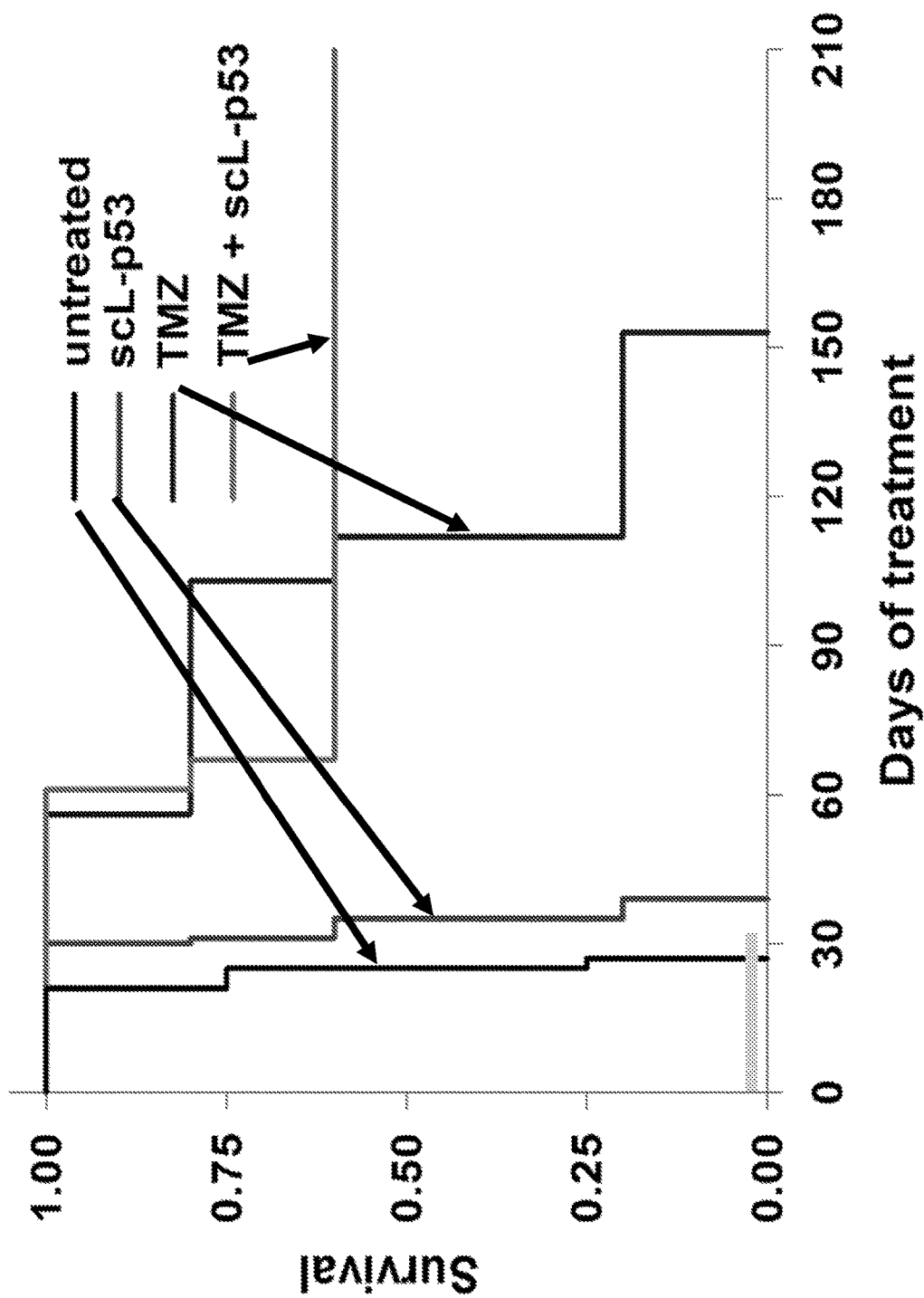
FIG. 27 shows Kaplan-Meier plots demonstrating SGT-53 sensitization to TMZ treatment significantly enhances survival in an intracranial U87 model of GBM.

Significantly Increased Survival of Mice Bearing Intracranial GBM Tumors after Treatment with the Combination of scL-p53 and TMZ As the above experiments demonstrated significant tumor responses, including regression post-treatment, the effect of this combination treatment on survival was next assessed. U87MG-Luc xenograft brain tumors were induced in nude mice as described above. 10 days post-inoculation, tumor-bearing animals were i.v. tail vein injected with TMZ alone (25.0 mg/kg/injection), scL-p53 alone (30 ug DNA/mouse/injection) (prepared as described in U.S. Pat. No. 7,780,882) or TMZ in combination with scL-p53. As a control, one group received PBS (vehicle). All i.v. injections were administered 2×/week to a total of 10 injections. The animals were monitored 2-3 times/week and euthanized when moribund. The results, analyzed by Kaplan-Meier method, are shown in FIG. 27 and Table 1 below. The gray bar in FIG. 27 indicates the duration of treatment. Although TMZ alone was able to prolong survival for a period of time in this TMZ responsive cell line, all of the mice succumbed to their tumor by ~day 155 with a Median Survival of 112 days. However, the survival time was extended considerably by the addition of scL-p53 to the treatment regimen. In these animals 60% of the mice were still surviving at day 210. Therefore, the % survival prolongation for mice receiving this combination regimen was >740 times that of the untreated mice, 500 times that of scL-p53 alone and almost twice that of TMZ alone. Thus, this adding scL-p53 to treatment with TMZ results in a significant increase in long term survival.

TABLE 1

| Treatment | n | Median Survival (Days) | Survival Prolongation (%)* | Log Rank P-value |
|---|---|---|---|---|
| Untreated | 4 | 25 | — | — |
| scL-p53 | 5 | 35 | 40 | 0.0117 |
| TMZ | 5 | 112 | 348 | 0.0088 |
| TMZ + scL-p53 | 5 | >210 | >740 | 0.0058 |

*Determine as a ratio of the median survival of untreated GBM xenografts

Figure 28:
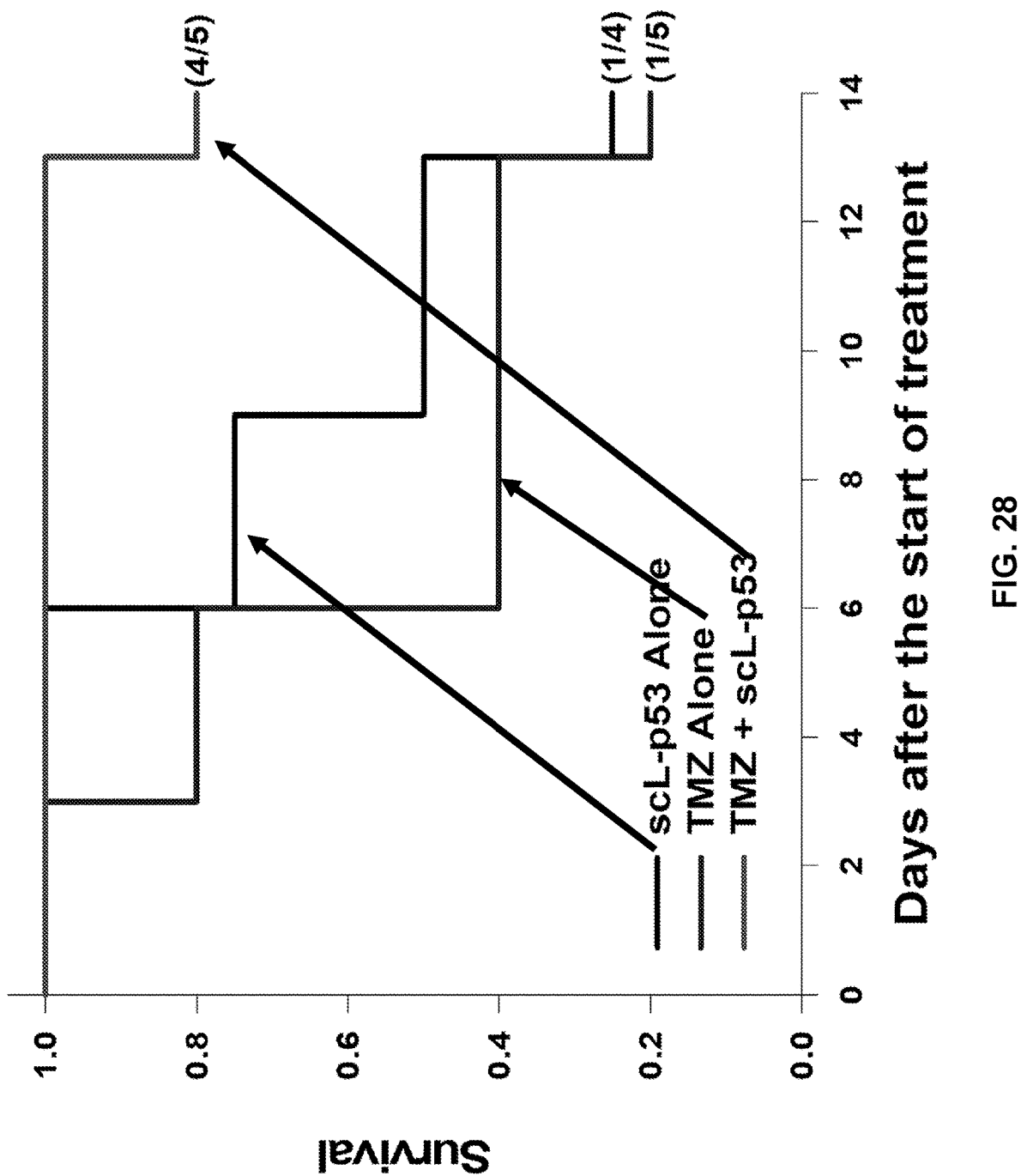
FIG. 28 shows Kaplan-Meier plots demonstrating SGT-53 sensitization to TMZ treatment significantly enhances survival in an intracranial TMZ Resistant Model of GBM (T98G Cells).

Significantly Increased Survival of Mice Bearing TMZ Resistant Intracranial GBM Tumors after Treatment with the Combination of scL-p53 and TMZ The in vitro studies described above indicated that transfection of TMZ resistant brain tumor cells could be sensitized to TMZ by transfection of scL-p53. Thus an experiment was performed to assess survival of mice bearing intracranial tumors derived from TMZ resistant human GBM cell line T98G. Athymic nude mice were intracranially inoculated with T98G human glioblastoma cell line. Ten days after the inoculation, animals were imaged by MRI and evenly divided into 3 groups. Treatment was started immediately after imaging. The animals were iv treated with 100 mg/m$^2$ of TMZ once a day for 14 consecutive days, iv administered scL-p53 (30 ug DNA/injection) (prepared as described in U.S. Pat. No. 7,780,882) twice weekly for 2 weeks, or the combination of both treatments. Survival was monitored. The results, analyzed by Kaplan-Meier method, are shown in FIG. 28. The number of mice surviving/group at day 14 is indicated for each group. Over this 2 week time of treatment a significant number of animals succumbed to their disease in the two groups that received TMZ or scL-p53 as a single agent. In contrast, 4 of 5 mice that had received the combination therapy were still surviving. Thus, this small efficacy experiment confirms the in vitro data and indicates that treatment with scL-p53 can sensitize previously resistant GBM tumors to TMZ.

Example 15

Enhanced Apoptosis in Intracranial Brain Tumors by the Combination of scL-p53 and TMZ Tumor suppressor p53 is known to play a role in the apoptotic pathway. To begin to evaluate the mechanism responsible for the increase in tumor cell response and increase in animal survival observed with the combination of scL-p53 and TMZ, the level of apoptosis induced in intracranial U87MG-luc2 brain tumors after various treatments was determined using Annexin V-FITC and Flow Cytometry. U87MG-luc2 brain tumors were induced as described above. 10 days post inoculation of the cells, the mice were treated with either TMZ alone (5 mg/kg per injection per mouse, 2 injections per week), scL-p53 alone (30 ug DNA per injection per mouse, 2 injections per week) (prepared as described in U.S. Pat. No. 7,780,882) or the combination of scL-p53 and free TMZ. Each animal received a total of 3 injections after which the animals were euthanized, single cell population isolated from the tumors and subjected to the Annexin V assay.

Figure 29:
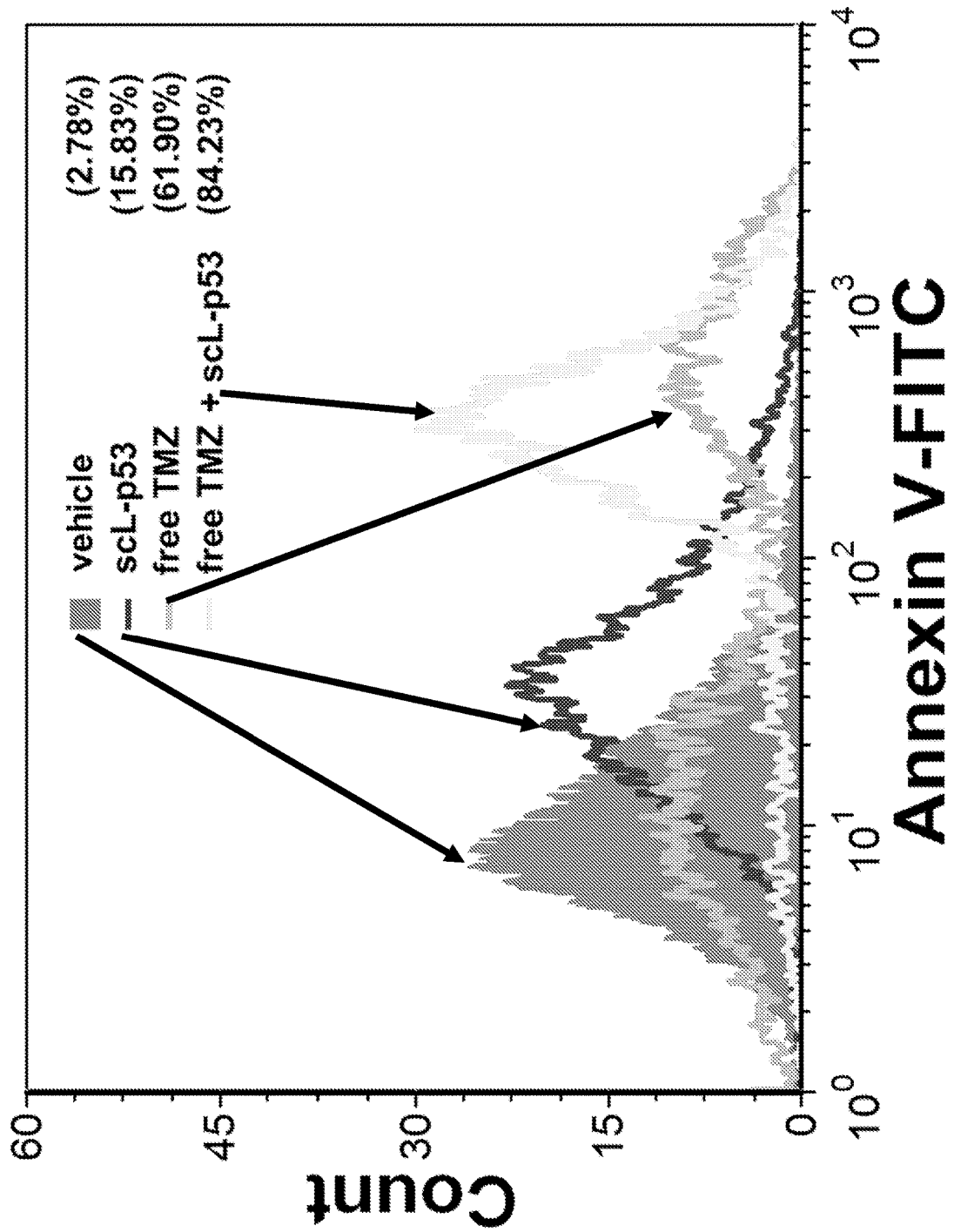
FIG. 29 shows percent of tumor cells in apoptosis post-treatment as indicated.

As shown in FIG. 29, there is a significant increase in the percent of the tumors cells in apoptosis after treatment with the combination of scL-p53 and TMZ compared to either treatment alone. Thus, these results indicate that uptake of systemically administered scL-p53 by the IC tumors results in an enhanced apoptotic response to chemotherapeutic agent TMZ.

Example 16

Treatment of TMZ Resistant GBM Tumors with scL-p53 Downmodulates MGMT Expression In Vitro and In Vivo The primary mechanism of resistance to TMZ is over expression of O$^6$-methylguanine-DNA-methyl transferase (MGMT), which repairs the TMZ-induced DNA lesion by removing the O$^6$-guanine adducts. Thus, a means to down modulate MGMT activity would enhance the therapeutic effect of TMZ. A number of reports have indicated that increasing wtp53 expression could down-regulate expression of DNA repair genes such as MGMT and increase the sensitivity of tumor cells to alkylating agents such as TMZ. The in vitro and in vivo data described in the Examples above indicated that treatment with scL-p53 could reverse resistance to TMZ in brain tumor cells. One possible mechanism for this sensitization is p53 dependent down modulation of MGMT. Uptake of scL-delivered wtp53 was examined to determine if it had an effect on the level of MGMT expression in TMZ-resistant T98G human glioblastoma cells in vitro and in in vivo subcutaneous xenograft tumors. T98G cells were transfected with scL-p53 (prepared as described in U.S. Pat. No. 7,780,882). 16 and 24 hours post-transfection, the cells were harvested, protein isolated and 40 ug micrograms total protein was electrophoretically fractionated using a Nu-PAGE Precast 4-12% gradient gel, transferred to nitrocellulose membrane, and probed for expression of MGMT and GAPDH by Western blot analysis. The signal was detected by ECL reagent (FIG. 30).

Figure 30:
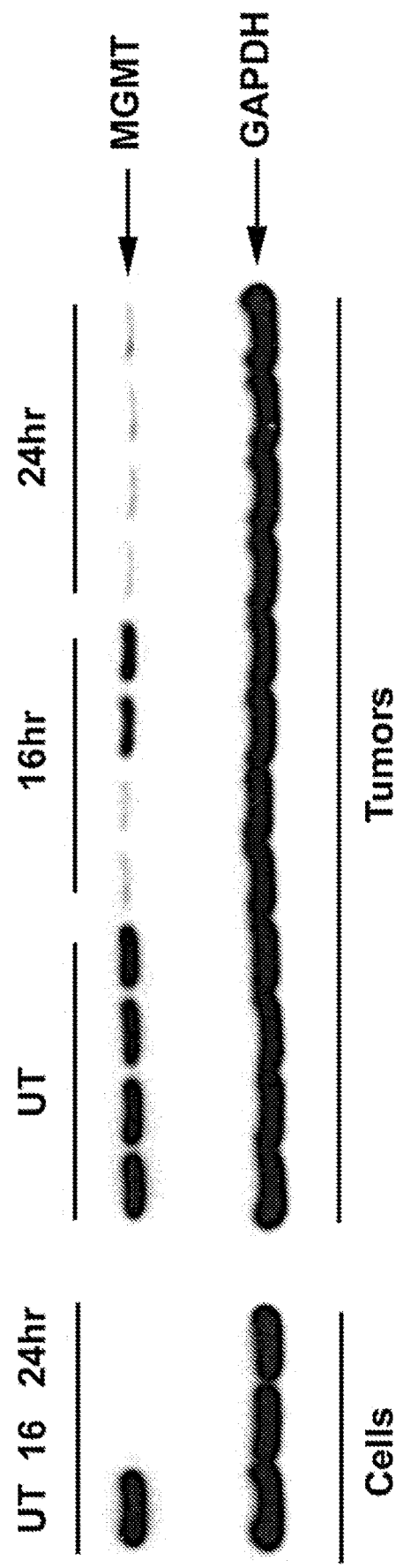
FIG. 30 shows down modulation of MGMT expression in T98G TMZ-resistant brain tumor cells and SQ xenograft tumors by systemic complex p53 gene therapy.

For the in vivo experiment shown in FIG. 30, scL-p53 (30 ug DNA/injection/mouse) was i.v. injected three times over a 24 hr period. At 16 and 24 hours after the last scL-p53 treatment, the mice were euthanized, tumors harvested, and protein extracted. Four mice were harvested at each time point. One group as a control did not receive SGT-53. 40 ug micrograms total protein was electrophoretically fractionated using a Nu-PAGE Precast 4-12% gradient gel, transferred to nitrocellulose membrane, and probed for expression of MGMT and GAPDH by Western blot analysis. The signal was detected by ECL reagent.

In vitro, there was complete down modulation of MGMT expression by 16 hours, which lasted as long as 24 hours post-transfection. Similarly, in the in vivo study, a significant decrease in the expression of MGMT was evident at 16 hours, with virtual elimination of the protein in two of the animals. By 24 hours after the last injection, virtually complete down modulation of MGMT was evident in all of the mice treated with SGT-53. Consistent expression of GAPDH protein demonstrated equal protein loading. The lack of MGMT to repair the DNA damage induced by TMZ in these tumors, along with the exogenous SGT delivered wtp53's positive effect on the apoptotic pathway, likely plays a role in overcoming the resistance of T98G to the killing effects of TMZ.

Figure 31:
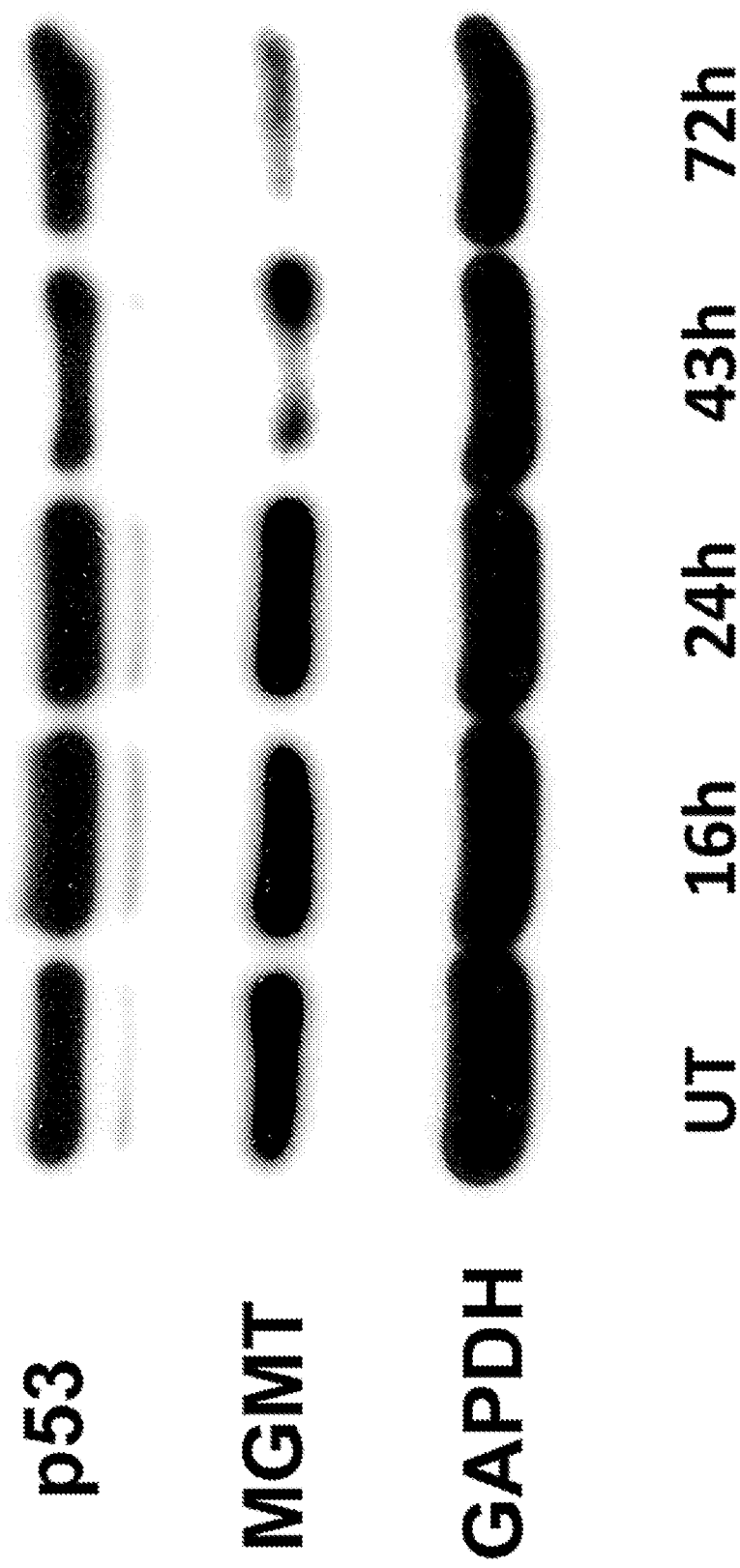
FIG. 31 shows down modulation of MGMT expression in T98G TMZ-resistant intracranial brain tumors by systemic TfRscFv-cationic liposome-p53 plasmid DNA (scL-p53) complex gene therapy.

More significantly, similar results were observed in an intracranial tumor model with T98G (FIG. 31). In this experiment, scL-p53 (at 30 ug DNA/mouse) was i.v. injected only once. At various time points between 16 and 72 hours after the scL-p53 injection, mice were euthanized, tumors harvested, and protein extracted. One group as a control (UT) did not receive SGT-53. 40 ug micrograms total protein was electrophoretically fractionated using a Nu-PAGE Precast 4-12% gradient gel, transferred to nitrocellulose membrane, and probed for expression of p53, MGMT and GAPDH by Western blot analysis. The signal was detected by ECL reagent.

At 16 and 24 hours after the single scL-p53 i.v. injection, an increase in the level of p53 protein is evident as compared to the UT animal indicating the presence of the exogenous p53. By 43 and 72 hours this signal had decreased back to a level similar to that of the UT control. More, importantly, as observed with the subcutaneous tumors, in these Intracranial tumors a significant decrease in expression of MGMT was observed at both 43 and 72 hours after treatment with scL-p53. This timing for the observed decrease in MGMT signal is consistent with the mechanism of action of p53 in sensitizing cells to TMZ by interfering with DNA repair mechanisms.

Example 17

Combination Treatment of scL-p53 and TMZ in Patients with Glioblastoma or Gliosarcoma Standard administration of temozolomide requires a daily dose of Temozolomide for 21 days. To optimize effectiveness of the potential chemosensitization of scL-p53, in a preferred embodiment, scL-p53 treatment will begin 1 day before temozolomide treatment. Pre-clinical studies have shown that the wtp53 tumor suppressor gene delivered by the scL-p53 complex functions to sensitize tumors to the chemotherapeutic agent, making them more responsive to the drug. Thus, it is critical that p53 is being expressed when temozolomide is administered in order to have the benefit of the scL-p53. Using the proposed schedule shown in FIG. 32, scL-p53 is being expressed at the start of temozolomide treatment.

In an alternate embodiment, two scL-p53 treatments will be administered before the start of temozolomide treatment. Here, scL-p53 will be administered on the same scheduled indicated in the table in FIG. 33, beginning on Day 1. However, the first TMZ treatment will not be until Day 6. Temozolomide will be administered orally at 100-250 mg/m$^2$ every day (including weekends) for 21 days (from day 6 to day 26).

Example 18

Preparation of Targeted Cationic Liposomes Comprising Melphalan (MEL)

Materials:
DOTAP (1,2-dioleoyl-3-trimethylammonium propane, chloride salt)
  Obtained from Avanti Polar Lipids, Inc. Cat. #890890E, MW 698.55
  Concentration: 25 mg/mL ethanol solution
  Dilute lipid to 20 mg/ml with absolute ethanol before use
DOPE (1,2-dioleoyl-sn-glycero-3-phosphoethanolamine)
  Obtained from Avanti Polar Lipids, Inc. Cat. #850725E, MW 744.04
  Concentration: 25 mg/mL ethanol solution.
  Dilute lipid to 20 mg/ml with absolute ethanol before use
Melphalan Hydrochloride (Mel), powder (M Wt=341.7)
  Obtained from Sigma, M2011-100 mg,
  Dissolve in absolute ethanol to a concentration of 50 mg/ml, with 10-15 ul of 6N HCl to aid in dissolution
Ultra-pure, endotoxin free LAL Reagent Water (e.g. Bio-Whittaker, Cat. #W50-500, endotoxin <0.005 EU/ml)
Injector: Hamilton Gastight Syringe, 1 ml (Hamilton #81230) with a 22 gauge needle, part #81365)

Procedure:
1. Fresh Mel solution is prepared each time by dissolving Mel in absolute ethanol to a concentration of 50 mg/ml (146.3 mM) with the addition of 6N HCl (~10-15 uL) by vortexing at high speed until dissolved (must be clear). Hold at room temperature until used to mix with lipids (Step 3 below).
2. Place lipid solutions at 37° C. for 10-15 min, following which place the lipid solutions in a 65° C. water bath with occasional shaking for 5 min.
3. To prepare the Lip-Mel: Place a brown glass bottle with stir bar on a hot plate set to 50° C. to 60° C. While stirring at high speed without splashing, add the lipids and Mel to the bottle in the following order (important):

For 1:1 (Lip:Mel) molar ratio
DOTAP           175 µl (of 20 mg/ml) = 5 µmol or 3.5 mg
DOPE            187.5 µl (of 20 mg/ml) = 5 µmol or 3.75 mg
Add Mel soln.,  68.3 µl (of 50 mg/ml) = 10 µmol,
Continuously stir for 3 min. after all 3 have been added 4. In the meantime, warm 4,569 uL LAL water to 65° C. in water bath in brown glass bottle with stir bar. Immediately prior to addition of the Lipid-Mel solution, move the bottle to a hot plate (50°-60° C.). Stir water at high speed with no splashing for a few sec to remove bubbles from the stir bar.
5. Keep the water on the hot plate. Continue stirring the water at high speed (without splashing) during lipid addition. After mixing lipids and Mel as above (Step 2), immediately and as rapidly as possible, using the Hamilton syringe for injection, inject the mixture into the hot water on the hot plate (50°-60° C.) directly into the center of the vortex. Continue stirring on high speed (without splashing) for 1 min after the addition of the lipid mixture while loosely covered.
6. Move the glass bottle to a RT stir plate, and, continue to stir slowly until the loosely covered solution cools down to 20-25° C. (room temperature)
7. Adjust the volume to 5 ml with room temperature LAL water.
8. Filter the solution using a 0.22 μm pore Milex GV filter.
9. Measure particle size and zeta potential if desired.

Results of these preparation methods demonstrate liposomes having a particle size of about 20-60 nm and a Zeta Potential of about 10 to 50 mV.

Example 19

Preparation of Targeted Cationic Liposome Containing Melphalan (scL/MEL) Without Chemical Conjugation (By Simple Mixing)

Using the MEL-comprising cationic liposomes prepared according to the procedure described above, the ligand targeted MEL cationic liposome complex as described herein is prepared by simple mixing of the components and without chemical conjugation. The preparation of the complexes was in accordance with the following general procedure:

To the liposome-water (or buffer) the appropriate amount of targeting moiety is added to give the desired ratio and mixed by gentle inversion 5-10 seconds. The targeting moiety can be a ligand including but not limited to transferrin or folate, or other proteins. It can also be an antibody or an antibody fragment that targets a cell surface receptor including, but not limited to, the transferrin or HER-2 receptor (e.g., TfRscFv). This mixture is kept at room temperature for 10-15 minutes (again inverted gently for 5-10 seconds after approximately 5 minutes). To yield the desired final volume the targeting moiety-Lip-MEL admixture is mixed with any volume (including none) of water (suitably deionized water) or a buffer of any pH including, but not limited to, Tris buffers, HEPES buffers or Phosphate Buffered Saline, required to give a desired volume and inverted gently for 5-10 seconds to mix. This mixture is kept at room temperature for 10-15 minutes (again inverted gently for 5-10 seconds after approximately 5 minutes).

Typically, for use in an in vitro assay, it is desirable that the amount of MEL in the final complex is in the range of about 1 μM to 30 μM per well; for in vivo use, it is desirable to provide about 1 mg/kg to about 50 mg/kg of MEL per injection. For use in vivo dextrose or sucrose is added last to a final concentration of about 1-50% (V:V) dextrose or sucrose, suitably 5% dextrose or 10% sucrose, and mixed by gentle inversion for 5-10 seconds. This mixture is kept at room temperature for 10-15 minutes (again inverted gently for 5-10 seconds after approximately 5 minutes).

A specific example for in vitro transfection at a suitable ratio of 1:30 (antibody fragment:liposome, w:w) and 1:1 Liposome:MEL (molar ratio) is as follows: For a final volume of approximately 600 uL, mix 250 μL of Lip:TMZ (2 mM stock) with 56.7 μL of antibody fragment (at an anti-transferrin receptor single chain antibody fragment [TfRscFv] concentration of 0.21 mg/mL). Add 293.34 of water or buffer.

The size (number average) of the final complex prepared by the method is between about 10 to 800 nm, suitably about 15 to 400 nm, most suitably about 20 to 200 nm with a zeta potential of between about 1 and 100 mV, more suitably 5 to 60 mV and most suitably 10 to 50 mV as determined by dynamic light scattering using a Malvern Zetasizer ZS. This size is small enough to efficiently pass through the tumor capillary bed, or cross the blood brain barrier, and reach the tumor cells.

The complex prepared as described above containing dextrose or sucrose (1-50%, volume to volume) can also be lyophilized to dryness and stored at room temperature, 2-8° C., or −20 to −80° C. The samples are reconstituted with water prior to use. The size (number average) of the final lyophilized complex after reconstitution is between about 10 to 800 nm, suitably about 15 to 400 nm, more suitably about 20 to 200 nm and most suitably 50 to 150 nm with a zeta potential of between about 1 and 100 mV, more suitably 5 to 60 mV and most suitably 10 to 50 mV as determined by dynamic light scattering using a Malvern Zetasizer ZS. These complexes retain at least 80% of the original biological activity.

Example 20

Increased Effect of Lip/MEL on Tumor Cells Compared to Free (Unencapsulated) MEL The scL-MEL nanocomplex was prepared as described above using an anti-transferrin receptor single-chain antibody fragment (TfRscFv) as the targeting moiety, a Lip:MEL molar ratio of 1:1 and 0.75:1 (sizes=30 and 25 nm, respectively) (liposome concentration=2 mM) and an TfRscFv to Liposome ratio if 1:30 (w:w). The size of the scL-MEL nanocomplex was 45 and 57 nm, respectively. The in vitro cell killing ability of the scL-MEL was compared to free, unencapsulated MEL in KMS-11 cells.

For these in vitro cell survival studies, the human multiple myeloma cell line KMS-11 was used. These are non-adherent cells and grow in suspension. $4 \times 10^5$ cells in 2.6 ml of serum free media were incubated in a sterile 50 ml centrifuge tube with 400 ul of the scL-MEL (at either ratio) or unencapsulated MEL for one hour. Following this incubation, the medium was supplemented with fetal bovine serum to a final concentration of 10% (0.3 ml/tube). After incubation for an additional 47 h, cell viability was determined by Trypan Blue counting of the cells. To accomplish this, one part trypan blue solution is mixed with 1 part cell suspension (1:1 dilution) in a 2 mL eppendorf tube (e.g. 200 μL trypan blue is mixed with 200 μL cell suspension). Using a hemacytometer and a microscope the number of viable cells (unstained) and dead cells (stained) are counted. The average number of cells per 0.1 $mm^3$ is calculated and the number of cells per mL determined. The percent of viable cells is calculated as follows:

Viable Cells %=(Number of viable cells/Number of Cells)*100

The results are plotted and the $IC_{50}$ and $IC_{30}$ values, the drug concentration resulting in 50% and 30% cell kill, respectively, was interpolated from the graph of the drug concentration versus the percent of viable cells.

Figure 33:
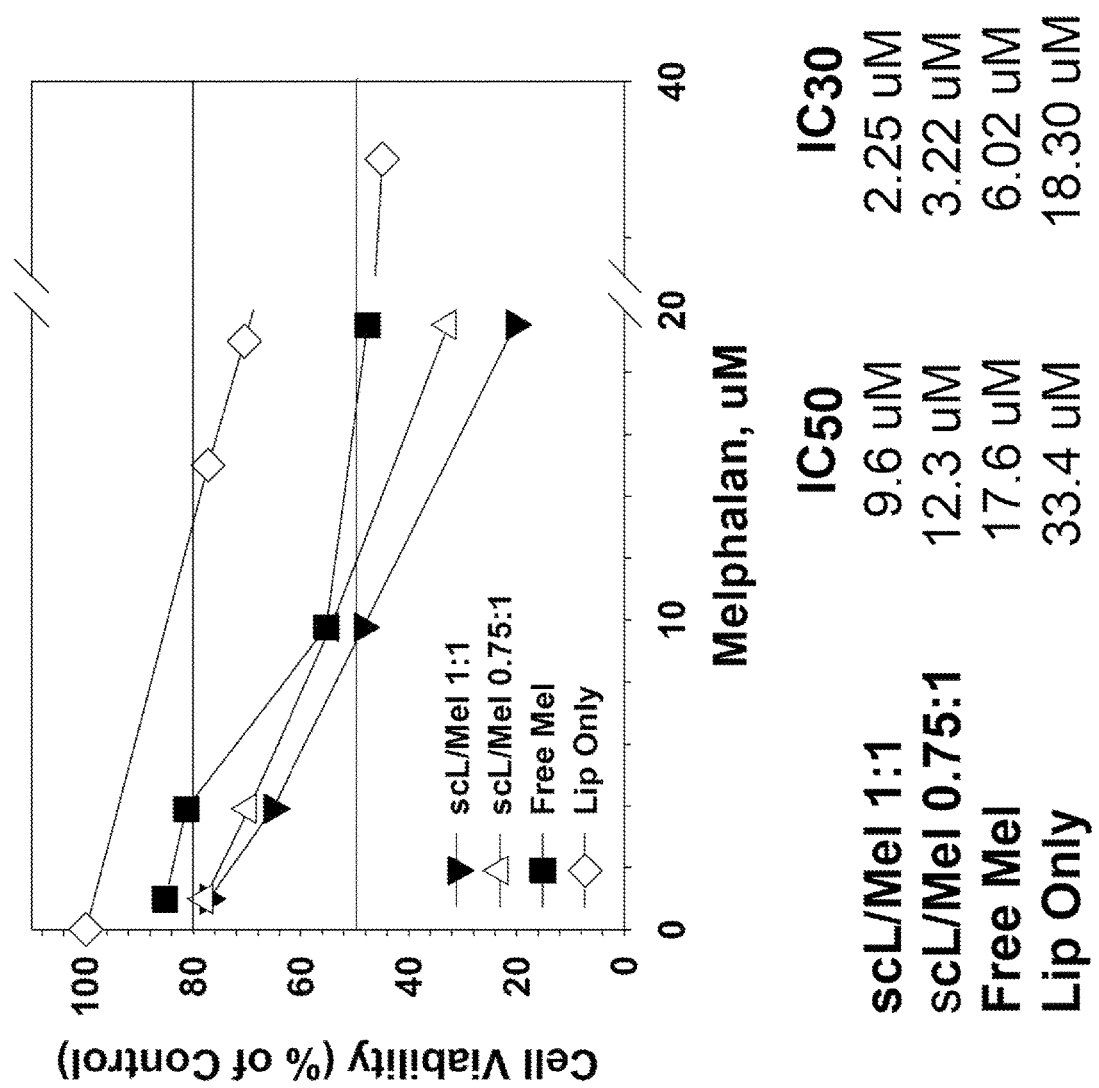
FIG. 33 shows KMS-11 cell survival versus concentration of melphalan (MEL) for free MEL and a targeted cationic liposome comprising MEL, as described herein.

FIG. 33 shows that tumor targeting scL-MEL nano complex, in which the MEL is encapsulated in the liposome, has significantly improved anti-cancer efficacy compared to unencapsulated MEL. The unencapsulated MEL has an $IC_{50}$ value of 17.6 uM. In contrast, when encapsulated in the liposome via the method of this invention at a 1:1 molar ratio of Liposome to MEL, and delivered to the tumor cell by means of the tumor-targeting nanocomplex of this invention at approximately 2 fold less MEL will effectively kill the cancer cells ($IC_{50}$ of 9.6 uM). Although not as dramatic, there was also a 30% decrease in the $IC_{50}$ values between the unencapsulated MEL and scL-MEL when the Lip-MEL was prepared at a Liposome:Mel ratio of 0.75:1 (molar ratio). Transfection with the Liposome alone did not result in any significant cell kill ($IC_{50}$>33 µM) indicating that the sensitization observed with the scL-MEL is not a result of non-specific cell kill by the liposome. Thus a variety of different molar ratios of liposome to Melphalan when used in the methods of this invention will result in a compound which when complexed to the targeting moiety by simple mixing and without chemical conjugation using the methods of this invention will result in a complex that has unexpected enhanced efficacy against multiple myeloma cells.

Figure 34:
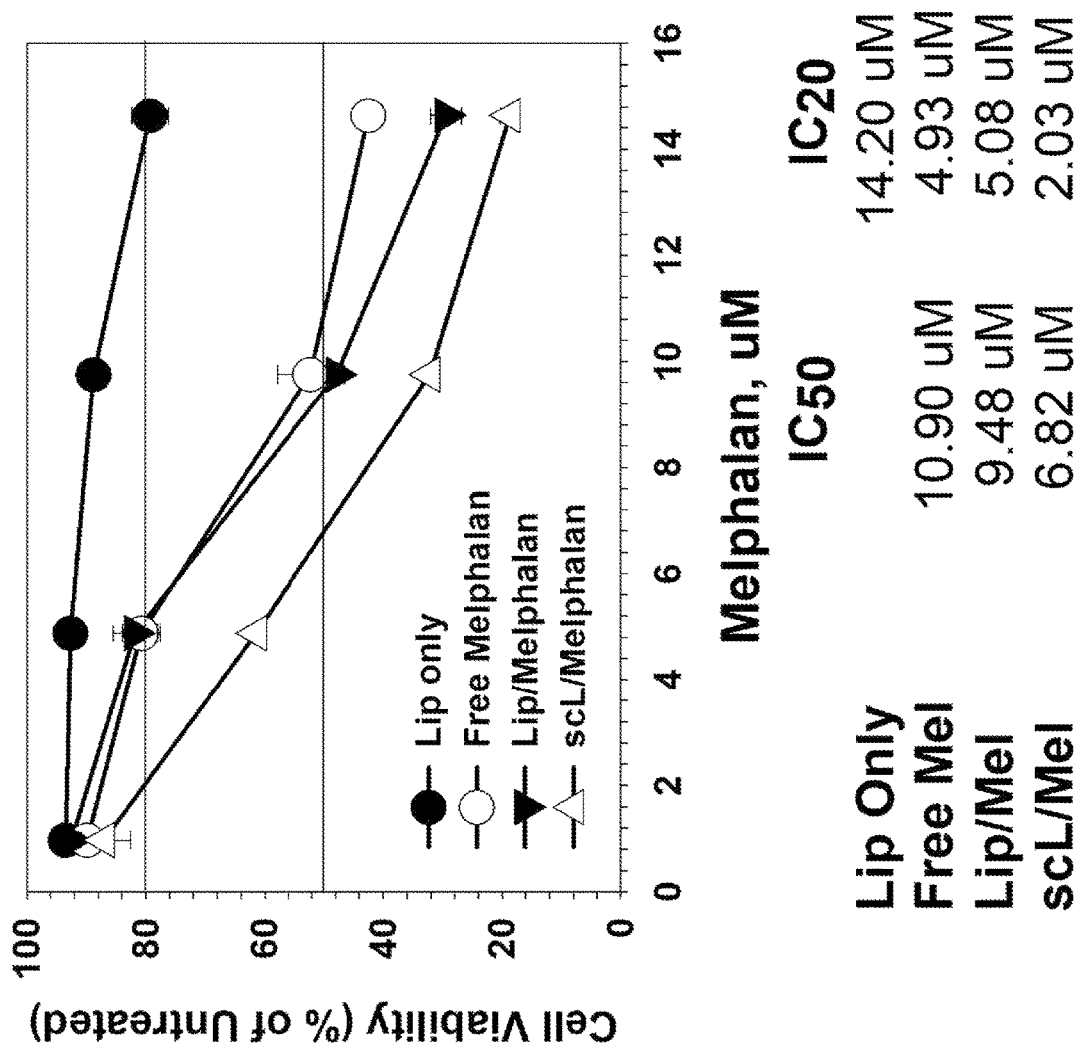
FIG. 34 shows comparison of unencapsulated MEL, with Lip-MEL without the targeting moiety and with the full TfRscFv-cationic liposome-melphalan complex (scL-MEL), as well as with liposome only.

Similar results are shown in FIG. 34 comparing unencapsulated MEL, with Lip-MEL as described herein without the targeting moiety and with the full scL-MEL nanocomplex, as well as with liposome only. The Lip-MEL and scL-MEL were prepared as described in Examples 1 and 2 at molar ratios of Liposome to MEL of 1:1) (liposome concentration=2 mM). An anti-transferrin receptor single-chain antibody fragment (TfRscFv) was used as the targeting moiety, with a TfRscFv to Liposome ratio of 1:30 (w:w). Once again the liposome only has virtually no cell killing effect on these multiple myeloma cells. In contrast, even without the targeting moiety, when encapsulated in the Liposome at molar ratios of 1:1 (Lip:MEL) using the methods described herein, there was a significant decrease in the $IC_{50}$ value compared to free (unencapsulated) MEL. This level of sensitization was even greater (almost 2 fold) when the full scL-Mel complex was used. This level of sensitization of multiple myeloma cells after encapsulation in liposomes via the method of this invention is unexpected.

Example 21

Figure 35:
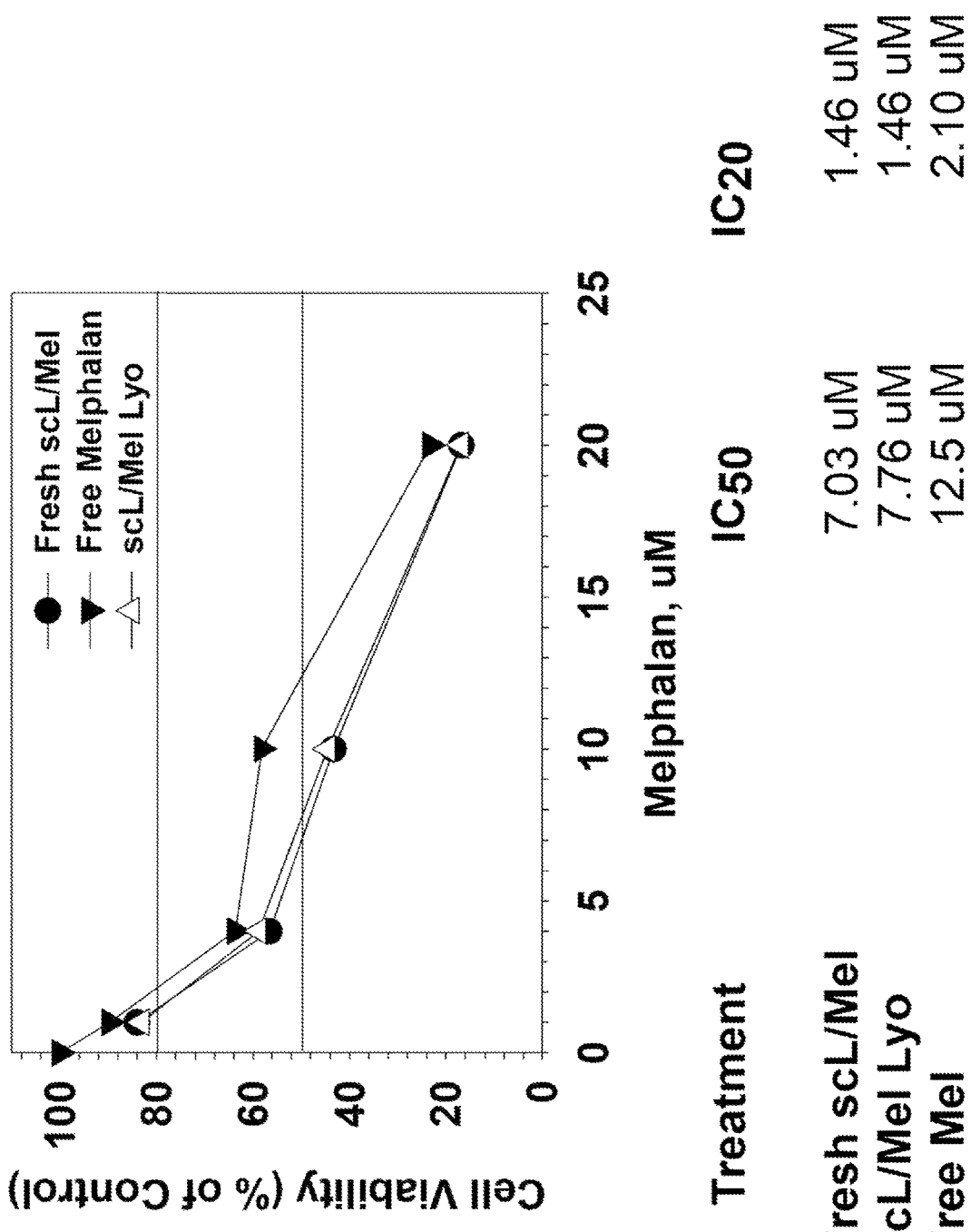
FIG. 35 shows comparison of unencapsulated MEL, with fresh and lyophilized scL-MEL complex.

Maintenance of Biological Activity of scL-MEL After Lyophilization and Reconstitution The scL-MEL complex containing sucrose (final concentration=10%) was prepared as described above using an anti-transferrin receptor single-chain antibody fragment (TfRscFv) as the targeting moiety, a Lip:MEL molar ratio of 1:1 (size=21 nm) (liposome concentration=2 mM) and an TfRscFv to Liposome ratio if 1:30 (w:w). This complex was subsequently lyophilized and the samples stored in a desiccator at 2-8° C. After one week of storage the lyophilized scL-Mel complex was reconstituted with endotoxin free water and used to transfect KMS-11 cells as described above. The size of the reconstituted scL/MEL was 56 nm (number average), within the preferred size range of the complex prepared by the method of this invention when freshly prepared. Thus, lyophilization did not significantly alter the size of the complex. The cell killing ability of the lyophilized/reconstituted scL-MEL was compared with freshly prepared scL-MEL and free (unencapsulated) MEL. The results are shown in FIG. 35. Both the $IC_{50}$ and $IC_{20}$ values for the freshly prepared and lyophilized scL-MEL nanocomplex are virtually identical. Thus, this lyophilized complex is also able to maintain at least 80% of its biological activity.

Example 22

Combination Therapy with scL-MEL and Tumor Suppressor Gene p53

Restoration or activation of the tumor suppressor p53 pathway has been shown to induce apoptosis (programmed cell death), in multiple myeloma cells (Ludwig H, Beksac M, Blade J, Boccadoro M, Cavenagh J, Cavo M, et al. Current MM treatment strategies with novel agents: a European perspective. Oncologist 2010; 15(1):6-25; Hurt E M, Thomas S B, Peng B, Farrar W L. Reversal of p53 epigenetic silencing in multiple myeloma permits apoptosis by a p53 activator. Cancer Biology & Therapy 2006; 5:1154-60). Furthermore, studies investigating the molecular causes of multiple myeloma disease have shown that myeloma cells often have healthy (i.e., unmutated) p53 genes but very little p53 protein. Restoration of p53 levels slows the growth of multiple myeloma cells and causes their death. Thus p53 gene therapy is a logical treatment strategy for multiple myeloma.

Tumor-Targeting scL-p53 Nanocomplex for Gene Therapy

As described in U.S. Pat. No. 7,780,822, the disclosure of which is incorporated by reference herein in its entirety, a delivery system carrying a plasmid DNA encoding the wtp53 gene and targeted via TfRscFv (scL-p53) has been successfully developed. Systemic administration of scL-p53 results in high levels of wtp53 expression in numerous different tumor types. scL-p53 has also been developed for use in combination with chemotherapy/radiation to increase the tumor response to these standard therapeutic modalities by inducing apoptosis.

The use of the scL-p53 nanocomplex, shown to efficiently target and efficiently deliver wtp53 to both primary and metastatic tumors, should be an effective means to increase the levels of p53 protein in multiple myeloma cells.

scL-MEL and scL-p53 Combination Therapy

Described herein is the use of the combination of scL-MEL and scL-p53. The development of scL-MEL for use as a monotherapy will be of benefit to patients in that we have shown the unexpectedly high increase in multiple myeloma cell death after treatment with scL-MEL as compared the unencapsulated MEL, the form that is currently used for treatment. However, as increasing expression of p53 in multiple myeloma cells also has therapeutic potential, the combinatorial approach will have an even greater therapeutic potential.

Experimental Approach

The experiments are designed to demonstrate development of a new, more effective treatment regimen for multiple myeloma with use of scL-MEL, when used in combination with scL-p53.

In Vitro Results

Figure 36:
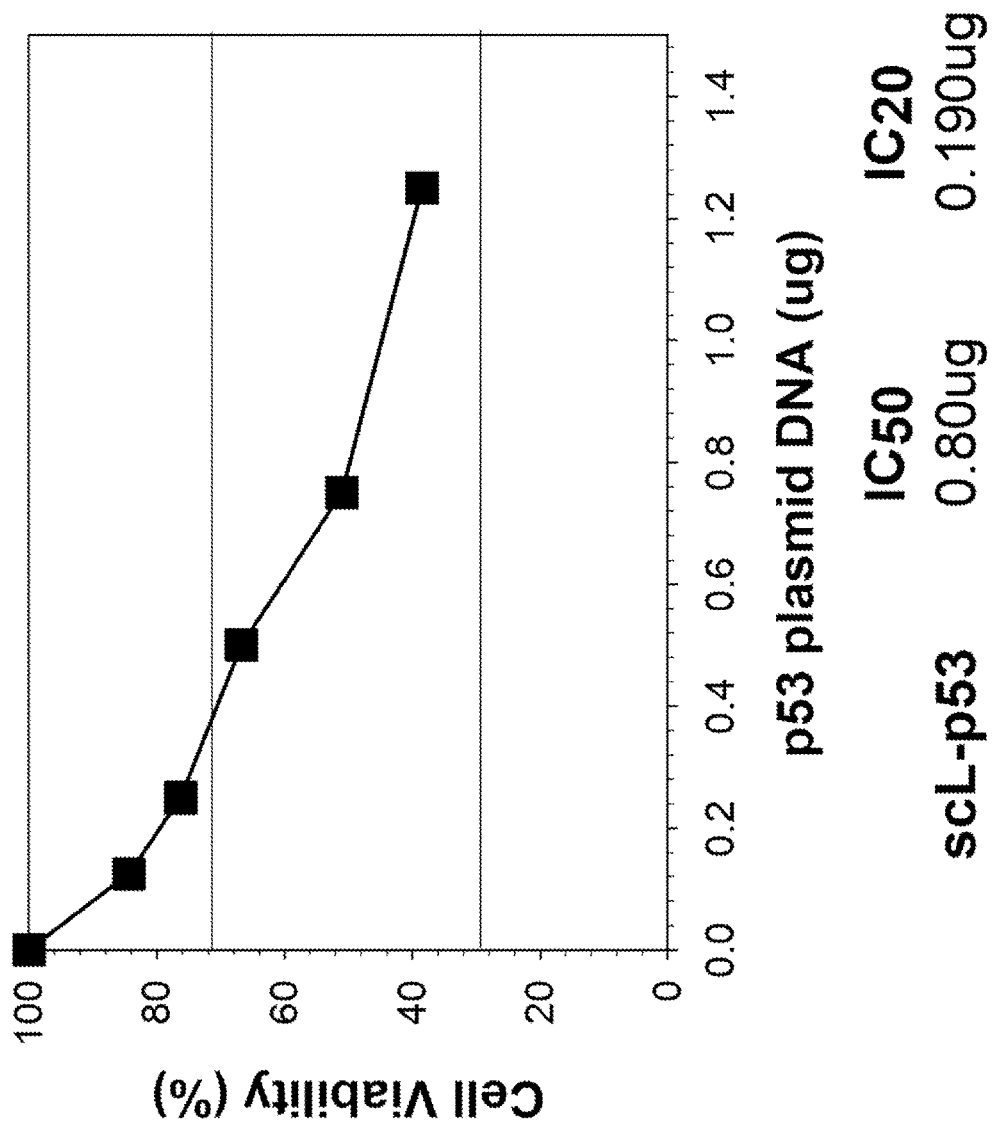
FIG. 36 shows the effect of targeted scL-p53 therapy on KMS-11 cells.

To test the hypothesis that treatment with scL-p53 could result in multiple myeloma cell death a preliminary cell viability assay was performed as described above. Human multiple myeloma cell line KMS-11, described above, was transfected with scL-p53 alone. scL-p53 was prepared by simple mixing of the components in a defined order as described in U.S. Pat. No. 7,780,822. The complex was prepared with increasing doses of a plasmid encoding the normal human wtp53 gene. Plasmid DNA doses ranged from 0 to 1.3 ug DNA. The KMS-11 cells were transfected using the identical procedure described above. The percent of viable cells was determined 24 h post-transfection and the $IC_{50}$ and $IC_{20}$ values determined. Transfection with scL-p53 resulted in a dose-dependent level of cell death indicating that increasing the expression of wtp53 in multiple myeloma cells by itself can result in significant level of cell death (FIG. 36). This is unexpected since the reports in the art regarding modulation of p53 expression in multiple myeloma have all employed either additional activating agents or indirectly, not directly, affected p53 by blocking expression of other proteins.

Figure 37:
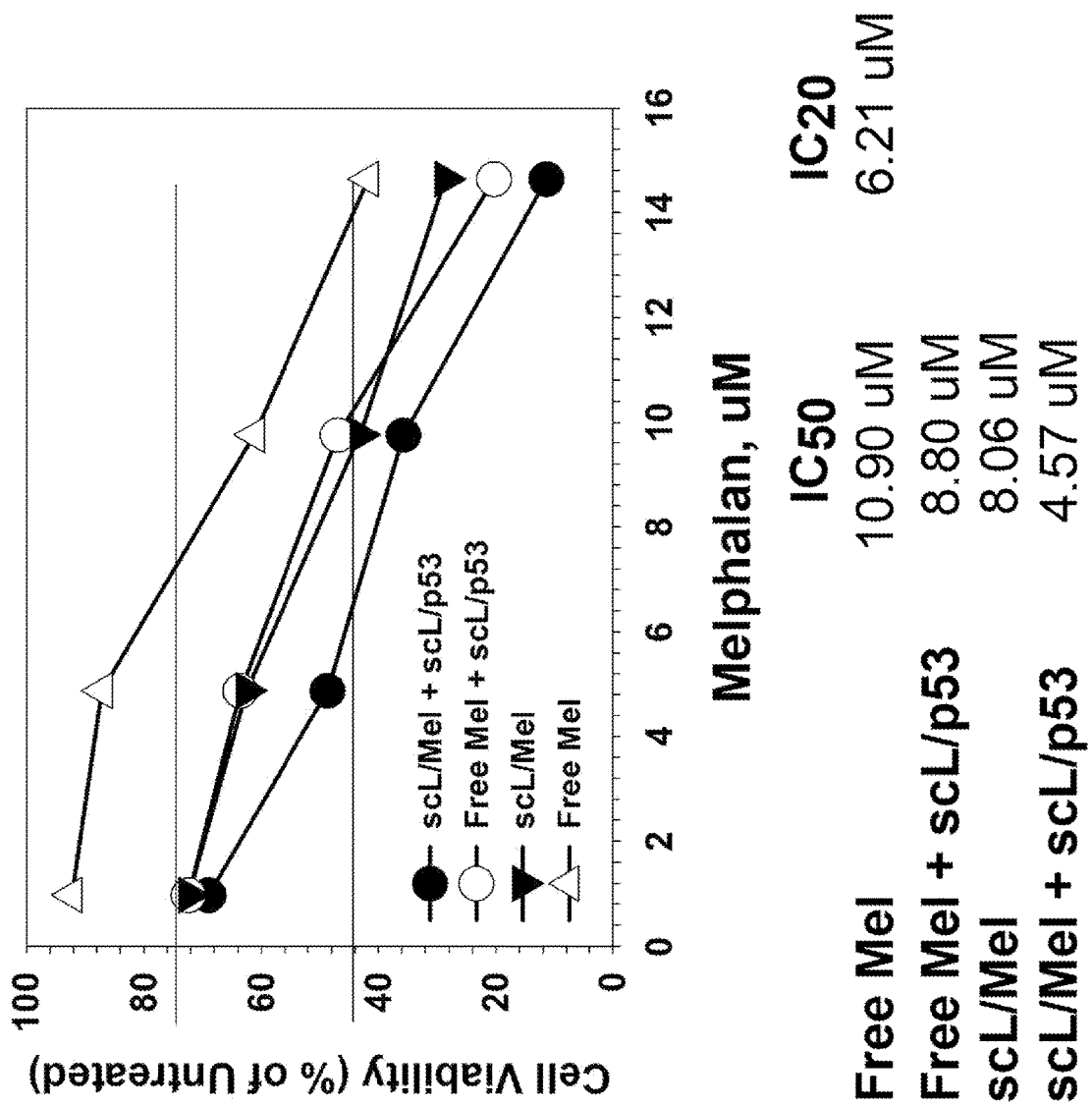
FIG. 37 shows the effect of free (unencapsulated) MEL alone, scL-MEL alone, or the combination of free (unencapsulated) or scL encapsulated MEL plus scL-p53 on KMS-11 cells.

The combination of scL-MEL and scL-p53, both of which were shown to increase the level of cell death on their own were transfected simultaneously to assess the response of KMS-11 cells to this combination therapy. KMS-11 cells were transfected using the procedure described above. scL/MEL was prepared as described above using an anti-transferrin receptor single-chain antibody fragment (TfRscFv) as the targeting moiety, a Lip:MEL molar ratio of 1:1 (liposome concentration=2 mM) and an TfRscFv to Liposome ratio if 1:30 (w:w). Cells ($4 \times 10^5$ per tube) were transfected with different scL/MEL complexes containing increasing doses of MEL. The scL-p53 was prepared as previously described (U.S. Pat. No. 7,780,822). The DNA dose used for all transfections was 0.2 ug/$4 \times 10^5$ cells. This dose was based upon the data from FIG. 36 wherein the $IC_{20}$ was found to be a dose of approximately 0.2 ug. The $IC_{20}$ was used to allow detection of an additive or synergistic effect of the two treatments. The KMS-11 cells were transfect with Free (unencapsulated) MEL alone, scL-MEL alone, or the combination of Free (unencapsulated) or scL encapsulated MEL plus scL-p53 (FIG. 37).

When compared to free MEL alone, transfection with the scL-Mel complex resulted in a significant level of chemosensitization to the drug. Moreover, when used in combination with either free or scL complexed MEL the addition of scL-p53 was able to significantly improve the response of the KMS-11 cells to this chemotherapeutic agent, with the combination of scL-MEL and scL-p53 being the most effective. Compared to the $IC_{50}$ of unencapsulated MEL, the standard form used as a therapeutic ($IC_{50}$=10.9) the $IC_{50}$ of the scL-MEL plus scL-p53 was 4.57, a greater that 2 fold increase in cell death.

Although these studies have been performed in vitro, it is fully expected that similar results (increased multiple myeloma cell death) will also occur when scL-Mel and scL-p53 are administered systemically in combination to human patients. The dose of scL-p53 is expected to be between 2.4 and 3.6 mg/infusion with twice weekly infusions for 5 weeks. The scL-MEL will be administered as a single intravenous infusion of a dose of between 6 and 16 mg/m$^2$ at two week intervals for four doses.

The unexpected level of enhancement of the combination observed here indicates the potential of this combination approach as a new therapeutic modality for the treatment of multiple myeloma in human patients.

Example 23

Preparation of Cationic Liposomes Comprising Atropine

Materials:
DOTAP (1,2-dioleoyl-3-trimethylammonium propane, chloride salt)
  Obtained from Avanti Polar Lipids, Inc. Cat. #890890E, MW 698.55
  Concentration: 25 mg/mL ethanol solution
  Dilute lipid to 20 mg/ml with absolute ethanol before use
DOPE (1,2-dioleoyl-sn-glycero-3-phosphoethanolamine)
  Obtained from Avanti Polar Lipids, Inc. Cat. #850725E, MW 744.04
  Concentration: 25 mg/mL ethanol solution.
  Dilute lipid to 20 mg/ml with absolute ethanol before use
Atropine, powder (M Wt=289.37)
  Obtained from Sigma
  Dissolve in absolute ethanol to a concentration of 100 mM.
Ultra-pure, endotoxin free LAL Reagent Water (e.g. Bio-Whittaker, Cat. #W50-500, endotoxin <0.005 EU/ml)
Injector: Hamilton Gastight Syringe, 1 ml (Hamilton #81230) with a 22 gauge needle, part #81365)

Procedure:
1. Fresh Atropine solution is prepared each time by dissolving Atropine in absolute ethanol to a concentration of 100 mM by vortexing at high speed until dissolved (must be clear). Hold at room temperature until used to mix with lipids (Step 3 below).
2. Place lipid solutions at 37° C. for 10-15 min, following which place the lipid solutions in a 65° C. water bath with occasional shaking for 5 min.
3. To prepare the Lip-Atropine: Place a brown glass bottle with stir bar on a hot plate set to 50° C. to 60° C. While stirring at high speed without splashing, add the lipids and Atropine to the bottle in the following order (important):

| For 1:1 (Lip:Atropine) molar ratio |
| --- |
| DOTAP  175 µl (of 20 mg/ml) = 5 µmol or 3.5 mg |
| DOPE   187.5 µl (of 20 mg/ml) = 5 µmol or 3.75 mg |
| Add Atropine soln., 100 µl (of 100mM) = 10 µmol, |
| Continuously stir for 3 min. after all 3 have been added |

4. In the meantime, warm 4,569 uL LAL water to 65° C. in water bath in brown glass bottle with stir bar. Immediately prior to addition of the Lipid-Atropine solution, move the bottle to a hot plate (50°-60° C.). Stir water at high speed with no splashing for a few sec to remove bubbles from the stir bar.
5. Keep the water on the hot plate. Continue stirring the water at high speed (without splashing) during lipid addition. After mixing lipids and Atropine as above (Step 2), immediately and as rapidly as possible, using the Hamilton syringe for injection, inject the mixture into the hot water on the hot plate (50°-60° C.) directly into the center of the vortex. Continue stirring on high speed (without splashing) for 1 min after the addition of the lipid mixture while loosely covered.
6. Move the glass bottle to a RT stir plate, and, continue to stir slowly until the loosely covered solution cools down to 20-25° C. (room temperature)
7. Adjust the volume to 5 ml with room temperature LAL water.
8. Filter the solution using a 0.22 µm pore Milex GV filter.
9. Measure particle size and zeta potential if desired.

Results of these preparation methods demonstrate liposomes having a particle size of about 20-100 nm and a Zeta Potential of about 10 to 50 mV.

Example 24

Preparation of Targeted Cationic Liposomes Containing Atropine Without Chemical Conjugation (By Simple Mixing)

Using the Atropine-comprising cationic liposomes prepared according to the procedure described above in Example 23, the ligand targeted Atropine cationic liposome complex as described herein is prepared by simple mixing of the components and without chemical conjugation. The preparation of the complexes was in accordance with the following general procedure.

To the liposome-water (or buffer) the appropriate amount of targeting moiety is added to give the desired ratio and mixed by gentle inversion 5-10 seconds. The targeting moiety can be a ligand including but not limited to transferrin or folate, or other proteins. It can also be an antibody or an antibody fragment that targets a cell surface receptor including, but not limited to the transferrin or HER-2 receptor (e.g., TfRscFv). This mixture is kept at room temperature for 10-15 minutes (again inverted gently for 5-10 seconds after approximately 5 minutes). To yield the desired final volume the targeting moiety-Lip-Atropine admixture is mixed with any volume (including none) of water (suitably deionized water) or a buffer of any pH including, but not limited to, Tris buffers, HEPES buffers or Phosphate Buffered Saline, required to give a desired volume and inverted gently for 5-10 seconds to mix. This mixture is kept at room temperature for 10-15 minutes (again inverted gently for 5-10 seconds after approximately 5 minutes).

For use in vivo dextrose or sucrose is added last to a final concentration of about 1-50% (V:V) dextrose or sucrose, suitably 5% dextrose or 10% sucrose, and mixed by gentle inversion for 5-10 seconds. This mixture is kept at room temperature for 10-15 minutes (again inverted gently for 5-10 seconds after approximately 5 minutes).

The size (number average) of the final complex prepared by the method is between about 10 to 800 nm, suitably about 15 to 400 nm, most suitably about 20 to 200 nm with a zeta potential of between about 1 and 100 mV, more suitably 5 to 60 mV and most suitably 10 to 50 mV as determined by dynamic light scattering using a Malvern Zetasizer ZS. This size is small enough to efficiently pass through the tumor capillary bed, or cross the blood brain barrier.

Example 25

Preparation of Cationic Liposomes Comprising Irinotecan Hydrochloride

Materials
DOTAP (1,2-dioleoyl-3-trimethylammonium propane, chloride salt)
  Obtained from Avanti Polar Lipids, Inc. Cat. #890890E, MW 698.55
  Concentration: 25 mg/mL ethanol solution
  Dilute lipid to 20 mg/ml with absolute ethanol before use
DOPE (1,2-dioleoyl-sn-glycero-3-phosphoethanolamine)
  Obtained from Avanti Polar Lipids, Inc. Cat. #850725E, MW 744.04
  Concentration: 25 mg/mL ethanol solution.
  Dilute lipid to 20 mg/ml with absolute ethanol before use
Irinotecan HCl (IH) analytical sample (slightly yellow powder)
  Obtained from ScinoPharm Taiwan, Ltd.
    Dissolve in DMSO to a concentration of 50 mg/ml
Ultra-pure, endotoxin free LAL Reagent Water (we use BioWhittaker,
  Cat. #W50-500; endotoxin <0.005 EU/mL)
Injector: Hamilton Gastight Syringe, 1ml (Hamilton #81230) with a 22 gauge needle, part #81365)

Procedure
1. Warm lipids and IH solutions to 37° C. for 10-15 min.
2. Using a stir bar and hot plate, mix together for 5 min in a foil covered brown glass bottle without splashing the following in this order (important):

| | |
|---|---|
| DOTAP | 175 µl (of 20 mg/ml) = 5 µmol |
| DOPE | 187.5 µl (of 20 mg/ml) = 5 µmol |
| IH | 135.5 µl (of 50 mg/ml) = 10 µmol |

Before mixing, warm up the hot plate to about 50° C. Keep plate warm (about 50° C.) during the 5 min mixing.
3. In the meantime, warm ~4.35 ml water to 65° C. in foil covered brown glass bottle with stir bar.
4. After mixing for 5 min as above (Step 2), warm the mixture of DOTAP, DOPE, and IH to 50-60° C. in water bath established at 65° C. (should take less than 5 min).
5. Place the water form Step 3 on a warm (about 50° C.) plate. Stir water for a few sec to remove bubbles from the stir bar.
6. Using Hamilton syringe quickly inject the warm mixture of lipids and IH into the water, stirring on high speed (without splashing) for 2 min loosely covered.
7. Turn off the heat and continue to stir until the loosely covered solution cools down to 20-25° C. (room temperature)
8. Adjust the volume to 5 ml with room temperature LAL water.
9. Filter the solution using a 0.22 µm pore Milex GV filter.
10. Measure particle size and zeta potential.

Results of these preparation methods demonstrate liposomes having a particle size of about 20-100 nm and a Zeta Potential of about 10 to 50 mV.

Example 26

Preparation of Targeted Cationic Liposomes Containing Irinotecan Hydrochloride (IH) Without Chemical Conjugation (By Simple Mixing)

Using the Irinotecan-comprising cationic liposomes prepared according to the procedure described above in Example 25, the ligand targeted IH cationic liposome complex as described herein is prepared by simple mixing of the components and without chemical conjugation. The preparation of the complexes was in accordance with the following general procedure.

To the liposome-water (or buffer) the appropriate amount of targeting moiety is added to give the desired ratio and mixed by gentle inversion 5-10 seconds. The targeting moiety can be a ligand including but not limited to transferrin or folate, or other proteins. It can also be an antibody or an antibody fragment that targets a cell surface receptor including, but not limited to the transferrin or HER-2 receptor (e.g., TfRscFv). This mixture is kept at room temperature for 10-15 minutes (again inverted gently for 5-10 seconds after approximately 5 minutes). To yield the desired final volume the targeting moiety-Lip-Irinotecan admixture is mixed with any volume (including none) of water (suitably deionized water) or a buffer of any pH including, but not limited to, Tris buffers, HEPES buffers or Phosphate Buffered Saline, required to give a desired volume and inverted gently for 5-10 seconds to mix. This mixture is kept at room temperature for 10-15 minutes (again inverted gently for 5-10 seconds after approximately 5 minutes).

For use in vivo dextrose or sucrose is added last to a final concentration of about 1-50% (V:V) dextrose or sucrose, suitably 5% dextrose or 10% sucrose, and mixed by gentle inversion for 5-10 seconds. This mixture is kept at room temperature for 10-15 minutes (again inverted gently for 5-10 seconds after approximately 5 minutes).

The size (number average) of the final complex prepared by the method is between about 10 to 800 nm, suitably about 15 to 400 nm, most suitably about 20 to 200 nm with a zeta potential of between about 1 and 100 mV, more suitably 5 to 60 mV and most suitably 10 to 50 mV as determined by dynamic light scattering using a Malvern Zetasizer ZS. This size is small enough to efficiently pass through the tumor capillary bed, or cross the blood brain barrier.

Example 27

Enhanced Sensitization of Tumor Cells to Irinotecan Hydrochloride (IH) when Delivered by the scL Nanocomplex Although IH has been approved by the FDA for use in treatment of human colorectal cancers, as well as gastric and non-small cell lung cancers, the uptake of the drug by normal, non-tumor cells results in toxic side effects ranging from severe diarrhea (which can require hospitalization) to immunosuppression. A means to enhance efficacy while reducing these side effects would have significant clinical impact. We have previously shown that encapsulation of antisense oligonucleotides, siRNA and even small molecules by our tumor-targeting scL nanocomplex results in increased sensitization of various types of tumor cells to these therapeutic agents when compared to the free, unencapsulated agent. A more specific tumor-targeted delivery of IH will reduce the side effects that can occur from non-specific delivery to normal cells, and will also enable a reduction in the amount of drug required to result in effective killing of cancer cells. We performed experiments which unexpectedly demonstrated that this approach could be applied to IH.

A. In Vitro Studies

To determine whether the effect of the chemotherapeutic drug IH to tumor cells is enhanced when delivered by this tumor-targeting nanocapsule we compared the $IC_{50}$ values (the concentration yielding 50% growth inhibition) of free IH to scL-IH in a number of human tumor cell lines. For these studies, $2-2.5\times10^3$ cells/well of human colon cancer cell line HT-29, human pancreatic cancer cell line PANC-1 or human hepatocellular carcinoma cell line Hep G2 cells the appropriate growth medium were plated in a 96-well plate. After 24 hours, the media was replaced with serum-free medium, overlaid with 100 μL of increasing concentrations of either scL-IH nanocomplex, prepared as described above in Example 26, unliganded nanocomplex (L-IH), free IH or LipA only in serum-free medium. The cells were, incubated for 5 hours and then supplemented with FBS. After incubation for an additional 19 hours at 37° C. in a humidified atmosphere containing 5% $CO_2$, the wells were washed with IMEM without phenol red and a cell-viability XTT-based assay was performed. Formazan absorbance, which correlates to cell viability, was measured at 450 nm using a microplate reader. The $IC_{50}$ was interpolated from the graph of the log of drug concentration versus the fraction of surviving cells.

Colon cancer is one of the clinical indications for use of IH. At the low dose levels used, the free IH shows no significant effect on HT-29 human colon cancer cells ($IC_{50}$ value of >10 uM). In contrast, delivery of IH via the scL nanocomplex resulted in an significant increase in the level of cell kill with an $IC_{50}$ value of 1.5 uM. This is an unpectedly high increase in sensitivity of at least 10 fold over unencapsulated (free) IH. While the liposome-IH minus the targeting moiety displays a small level of improvement over free IH, it is significantly less effective than that of the scL-IH complex containing the TfRscFv targeting molecule. This is due to the efficient uptake of the complex into the cells as a result of the binding of the TfRscFv to the Tf receptor on the cells triggering receptor mediated endocytosis of the complex and trafficking of the scL encapsulated IH efficiently into the cells. Moreover, as with Free IH the liposome alone had no effect on cell kill indicating that the toxicity observed with scL-IH is not due to non-specific cytotoxicity, but is in fact due to the enhanced uptake of IH into the cells.

Similar results were observed when this approach was tested in two other human tumor cell lines, Hep G2 and PANC-1. IN both cases there is no effect of Free IH on the cells at the low doses tested. In neither case is an $IC_{50}$ value achieved when the cells are treated with Free IH. However, significant cell kill is also unpectedly observed when the same doses of IH are administered as part of the scL nanocomplex. Here also, as was observed in the HT-29 cells, in addition to no effect of the liposomes alone, a slight effect was observed with unliganded Liposome-IH, albeit significantly less than that with the targeted scL nanocomplex.

In order to demonstrate that the cell kill observed was tumor cell specific, we also performed an in vitro experiment in which non-cancerous lung fibroblast cells (IMR-90) were also treated with the scL-IH and the controls described above. The results show no sensitization by the scL-IH in these normal cells. These results demonstrate the tumor cell specificity of the scL nanocomplex. Therefore, we can successfully incorporate chemotherapeutic agent IH into the scL nanocomplex leading to enhanced and tumor cell specific cells killing by doses at which free IH is ineffective.

B. In Vivo Studies

The studies described above demonstrated that inclusion of IH within the scL nanocomplex could significantly enhance its tumor cell killing effect in various human tumor cell types compared to free IH in vitro. However, in order to assess the translational potential of this nanotechnology, it is necessary to demonstrate that scL-IH has similar effects in vivo.

In our initial in vivo experiment, we assessed the anti-tumor efficacy of various molar ratios of liposome to IH. Tumors of human colon tumor cell line HT-29 were induced in female athymic nude mice (5-10 animals/group) by the subcutaneous injection of $3.12\times10^5$ cells/site/mouse suspended in Matrigel® collagen basement solution. When the tumors reached ~100 mm³ treatment was initiated. Groups of mice were intravenously injected with the scL-IH complex, prepared as described above in Example 26, at molar ratios of Liposome to IH of 0.5:1, 1:1 and 2:1, with an IH concentration of 10 mg/kg. Groups of animals were also treated with Free IH, scL without IH, the nanocomplex without the targeting moiety (Lip-IH), as well as a group of untreated mice. The mice were IV injected twice weekly to a total of 15 injections. The results demonstrated that free IH has minimal effect on tumor growth compared to untreated tumors. The same minimal level of tumor response is evident when the scL-IH nanocomplex was prepared at liposome to IH molar ratios of 0.5:1 and 2:1. In contrast, there was almost complete inhibition of tumor growth when the mice were treated with the scL-IH nanocomplex prepared at a molar ratio of 1:1. Furthermore, the unliganded L-IH nanocomplex had virtually no anti-tumor effect, demonstrating the importance of the tumor-targeting moiety. Thus, in the remainder of the studies the optimal ratio of 1:1 (Liposome:IH) was used in preparation of the scL-IH nanocomplex.

To be utilized as a clinical agent, the scL-IH nanocomplex must be available in a stable form with a reasonable shelf-life. Thus, development of a lyophilized form of the scL-IH is an important step leading to the commercialization of our scL nanocomplex therapeutic agent. We have previously shown that we could produce a lyophilized form of the scL nanocomplex carrying plasmid DNA, siRNA and even contrast agent Magnevist. Thus we also compared the anti-tumor efficacy of the freshly prepared and a lyophilized form of scL-IH in three tumor models, mice bearing either HT-29 colon, PANC-1 pancreatic, or Hep G2 hepatocellular carcinoma xenograft tumors.

In the HT-29 animal experiment, the tumors were induced by injection of $5 \times 10^5$ cells in Matrigel® and the animals treated as described above with scL-IH at an IH concentration of 10 mg/kg and prepared at a Liposome:IH ratio of 1:1. Here also the mice received a total of 15 intravenous injections. The results are similar to that described above with significant tumor growth inhibition by the scL-IH, with only minimal effect from free IH and the nanocomplex minus the targeting moiety. More significantly, the lyophilized/reconstituted form of scL-IH yielded an identical anti-tumor response as the freshly prepared scL-IH.

Similar results were observed in mice bearing PANC-1 xenograft tumors. In this experiment the subcutaneous tumors were induced by inoculation of 200 ul of tissue obtained from serially passaged PANC-1 xenograft tumors in Matrigel®. Here each animal received a total of eleven intravenous injections of the various solutions, also at an IH concentration of 10 mg/kg and using the Liposome:IH molar ratio of 1:1.

As with the other two tumor models, the use of a lyophilized form of the scL-IH nanocomplex in the Hep G2 xenograft tumor model resulted in an identical pattern of anti-tumor efficacy as was observed when the mice were treated with the freshly prepared scL-IH nanocomplex. In this experiment, the tumors were induced by the subcutaneous injection of $5 \times 10^6$ Hep G2 cells in Matrigel®. As above, the animals were intravenously injected with the solutions at an IH concentration of 10 mg/kg and using the Liposome:IH molar ratio of 1:1. The mice received a total of twelve injections. Even over the short term of this study, there is significantly greater anti-tumor efficacy of the scL delivered IH in this rapidly growing tumor model when compared to the Free IH, in addition to the identical pattern between freshly prepared and lyophilized/reconstituted scL-IH.

Therefore, the above experiments show, through the significant anti-tumor effect observed in three separate mouse models of human cancer, the unexpected high increase in efficacy of the scL-IH compared to the currently used free IH. Moreover, the instant inventors have successfully produced a usable Lyophilized formulation of scL-IH that retains it biological activity after lyophilization/reconstitution, enhancing the translational potential of this therapeutic complex.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. A method of treating a brain cancer in a patient, comprising:
   administering via intravenous administration to the patient a targeted temozolomide cationic liposome complex, wherein the targeted temozolomide cationic liposome complex comprises:
   (a) a cationic liposome comprising 1,2-dioleoyl-3-trimethylammonium propane (DOTAP) and 1,2-dioleoyl-sn-glycero-3-phosphoethanolamine (DOPE);
   (b) temozolomide; and
   (c) an anti-transferrin receptor single chain Fv (TfRscFv) directly complexed with, but not chemically conjugated to, the cationic liposome;
   delivering the targeted temozolomide cationic liposome complex across the blood-brain barrier of the patient;
   delivering the temozolomide to the brain cancer; and
   inducing growth inhibition and/or regression of the brain cancer.

2. The method of claim 1, wherein the temozolomide is administered to the patient at a dose of about 10 mg/m$^2$ to about 500 mg/m$^2$.

3. The method of claim 2, wherein the temozolomide is administered to the patient at a dose of about 100 mg/m$^2$ to about 250 mg/m$^2$.

4. The method of claim 1, wherein the molar ratio of lipid:temozolomide in the cationic liposome:temozolomide is about 0.1:1 to about 5:1.

5. The method of claim 4, wherein the molar ratio of lipid:temozolomide in the cationic liposome:temozolomide is about 0.5:1 to about 2:1.

6. The method of claim 5, wherein the molar ratio of lipid:temozolomide in the cationic liposome:temozolomide is about 1:1.

7. The method of claim 2, wherein the weight ratio of TfRscFv:lipid in the cationic liposome is about 0.01:1 to about 0.5:10.

8. The method of claim 1, wherein the weight ratio of TfRscFv:lipid in the cationic liposome is about 0.3:10 to about 0.4:10.

9. The method of claim 8, wherein the weight ratio of TfRscFv:lipid in the cationic liposome is about 0.33:10.

10. The method of claim 8, wherein the brain cancer is a glioma, astrocytoma or a glioblastoma.

11. The method of claim 8, further comprising administering an additional different therapy to the patient in combination with the targeted temozolomide cationic liposome complex.

12. The method of claim 11, wherein the additional different therapy comprises administration of a chemotherapeutic agent, a small molecule, radiation therapy or a nucleic acid-based therapy.

13. The method of claim 12, wherein the nucleic acid-based therapy comprises administration of a targeted cationic liposome complex comprising an antisense oligonucleotide, an siRNA, an miRNA or an shRNA, and wherein the targeted cationic liposome complex comprises an anti-transferrin receptor single chain Fv (TfRscFv) directly complexed with, but not chemically conjugated to, the cationic liposome.

14. The method of claim 13, wherein the nucleic acid-based therapy comprises administration of a targeted cationic liposome complex comprising a plasmid DNA expressing wild-type p53, and wherein the targeted cationic liposome complex comprises an anti-transferrin receptor single chain Fv (TfRscFv) directly complexed with, but not chemically conjugated to, the cationic liposome.

15. The method of claim 1, wherein the intravenous administration is from a slow release implant, an osmotic pump or a mechanical pump.

16. A method of treating a brain cancer in a patient, comprising:
    (a) preparing a targeted temozolomide cationic liposome complex, comprising
        i. preparing a lipid solution comprising 1,2-dioleoyl-3-trimethylammonium propane (DOTAP) and 1,2-dioleoyl-sn-glycero-3-phosphoethanolamine (DOPE) in ethanol;
        ii. preparing a solution of temozolomide;
        iii. mixing the lipid solution with the solution of temozolomide;
        iv. injecting the mixture of lipid and temozolomide into an aqueous solution, thereby forming a temozolomide cationic liposome;
        v. mixing the temozolomide cationic liposome with an anti-transferrin receptor single chain Fv (TfRscFv) to form the targeted temozolomide cationic liposome complex, wherein the TfRscFv is directly complexed with, but not chemically conjugated to, the cationic liposome;
    (b) administering via intravenous administration to the patient the targeted temozolomide cationic liposome complex;
    (c) delivering the targeted temozolomide cationic liposome complex across the blood-brain barrier of the patient;
    (d) delivering the temozolomide to the brain cancer; and
    (e) inducing growth inhibition and/or regression of the brain cancer.

17. The method of claim 16, wherein temozolomide is administered to the patient at a dose of about 10 mg/m$^2$ to about 500 mg/m$^2$.

18. The method of claim 17, wherein temozolomide is administered to the patient at a dose of about 50 mg/m$^2$ to about 250 mg/m$^2$.

19. The method of claim 16, wherein the molar ratio of lipid:temozolomide is about 0.1:1 to about 5:1.

20. The method of claim 19, wherein the molar ratio of lipid:temozolomide is about 0.5:1 to about 2:1.

21. The method of claim 20, wherein the molar ratio of lipid:temozolomide is about 1:1.

22. The method of claim 16, wherein the weight ratio of TfRscFv:lipid is about 0.01:1 to about 0.5:10.

23. The method of claim 22, wherein the weight ratio of TfRscFv:lipid is about 0.3:10 to about 0.4:10.

24. The method of claim 23, wherein the weight ratio of TfRscFv:lipid in the cationic liposome is about 0.33:10.

25. The method of claim 16, wherein the brain cancer is a glioma, astrocytoma or a glioblastoma.

26. The method of claim 16, further comprising administering an additional different therapy to the patient in combination with the targeted temozolomide cationic liposome complex.

27. The method of claim 26, wherein the additional different therapy comprises administration of a chemotherapeutic agent, a small molecule, radiation therapy or a nucleic acid-based therapy.

28. The method of claim 27, wherein the nucleic acid-based therapy comprises administration of a targeted cationic liposome complex comprising an antisense oligonucleotide, an siRNA, an miRNA or an shRNA, and wherein the targeted cationic liposome complex comprises an anti-transferrin receptor single chain Fv (TfRscFv) directly complexed with, but not chemically conjugated to, the cationic liposome.

29. The method of claim 26, wherein the nucleic acid-based therapy comprises administration of a targeted cationic liposome complex comprising a plasmid DNA expressing wild-type p53, and wherein the targeted cationic liposome complex comprises an anti-transferrin receptor single chain Fv (TfRscFv) directly complexed with, but not chemically conjugated to, the cationic liposome.

30. The method of claim 16, wherein the intravenous administration is from a slow release implant, an osmotic pump or a mechanical pump.

\* \* \* \* \*